US010758557B2

(12) United States Patent
Sommadossi et al.

(10) Patent No.: US 10,758,557 B2
(45) Date of Patent: Sep. 1, 2020

(54) METHODS AND COMPOSITIONS FOR TREATING HEPATITIS C VIRUS

(71) Applicants: Idenix Pharmaceuticals LLC, Cambridge, MA (US); Universita degli Studi di Cagliari, Cagliari (IT)

(72) Inventors: Jean-Pierre Sommadossi, Boston, MA (US); Paolo La Colla, Sardinia (IT)

(73) Assignees: Idenix Pharmaceuticals LLC, Cambridge, MA (US); Universita degli Studi di Cagliari, Cagliari (IT)

(*) Notice: Subject to any disclaimer, the term of this patent is extended or adjusted under 35 U.S.C. 154(b) by 0 days.

(21) Appl. No.: 16/440,659

(22) Filed: Jun. 13, 2019

(65) Prior Publication Data

US 2019/0290670 A1 Sep. 26, 2019

Related U.S. Application Data

(63) Continuation of application No. 13/730,669, filed on Dec. 28, 2012, now Pat. No. 10,363,265, which is a continuation of application No. 13/623,674, filed on Sep. 20, 2012, now abandoned, which is a continuation of application No. 12/504,601, filed on Jul. 16, 2009, now Pat. No. 8,299,038, which is a continuation of application No. 10/602,691, filed on Jun. 20, 2003, now Pat. No. 7,608,597, which is a continuation of application No. 09/864,078, filed on May 23, 2001, now Pat. No. 6,914,054.

(60) Provisional application No. 60/206,585, filed on May 23, 2000.

(51) Int. Cl.
| | |
|---|---|
| A61K 31/7076 | (2006.01) |
| A61K 31/708 | (2006.01) |
| C07H 19/04 | (2006.01) |
| C07H 19/06 | (2006.01) |
| C07H 19/10 | (2006.01) |
| C07H 19/16 | (2006.01) |
| C07H 19/20 | (2006.01) |
| A61K 31/7068 | (2006.01) |
| A61K 31/7072 | (2006.01) |
| A61K 45/06 | (2006.01) |
| A61K 31/7056 | (2006.01) |
| A61K 38/21 | (2006.01) |
| G03C 1/005 | (2006.01) |

(52) U.S. Cl.
CPC ........ *A61K 31/708* (2013.01); *A61K 31/7056* (2013.01); *A61K 31/7068* (2013.01); *A61K 31/7072* (2013.01); *A61K 31/7076* (2013.01); *A61K 38/21* (2013.01); *A61K 45/06* (2013.01); *C07H 19/04* (2013.01); *C07H 19/06* (2013.01); *C07H 19/10* (2013.01); *C07H 19/16* (2013.01); *C07H 19/20* (2013.01); *G03C 1/0051* (2013.01)

(58) Field of Classification Search
None
See application file for complete search history.

(56) References Cited

U.S. PATENT DOCUMENTS

| | | |
|---|---|---|
| 3,074,929 A | 1/1963 | Hitchings et al. |
| 3,116,282 A | 12/1963 | Hunter |
| 3,480,613 A | 11/1969 | Walton et al. |
| 3,798,209 A | 3/1974 | Wilkowski et al. |
| 3,891,623 A | 6/1975 | Vorbruggen et al. |
| 4,022,889 A | 5/1977 | Bannister et al. |
| 4,058,602 A | 11/1977 | Beisler et al. |
| RE29,835 E | 11/1978 | Witkowski et al. |
| 4,209,613 A | 6/1980 | Vorbruggen |
| 4,239,753 A | 12/1980 | Skulnick et al. |
| 4,294,766 A | 10/1981 | Schmidt et al. |
| 4,522,811 A | 6/1985 | Eppstein et al. |
| 4,605,659 A | 8/1986 | Verheyden et al. |
| 4,689,404 A | 8/1987 | Kawada et al. |
| 4,754,026 A | 6/1988 | Kawada et al. |
| 4,814,477 A | 3/1989 | Wijnberg et al. |
| 4,880,784 A | 11/1989 | Robins et al. |
| 4,952,740 A | 8/1990 | Juge et al. |
| 4,957,924 A | 9/1990 | Beauchamp |
| 5,034,394 A | 7/1991 | Daluge |
| 5,118,672 A | 6/1992 | Schinazi et al. |
| 5,122,517 A | 6/1992 | Vince et al. |
| 5,149,794 A | 9/1992 | Yatvin et al. |
| 5,157,027 A | 10/1992 | Biller et al. |
| 5,194,654 A | 3/1993 | Hostetler et al. |
| 5,200,514 A | 4/1993 | Chu |
| 5,223,263 A | 6/1993 | Hostetler et al. |
| 5,246,924 A | 9/1993 | Fox et al. |
| 5,256,641 A | 10/1993 | Yatvin et al. |
| 5,256,797 A | 10/1993 | Chou et al. |
| 5,322,955 A | 6/1994 | Matsumoto et al. |
| 5,371,210 A | 12/1994 | Chou et al. |

(Continued)

FOREIGN PATENT DOCUMENTS

| | | |
|---|---|---|
| CA | 2252144 | 4/2000 |
| DE | 1919307 | 1/1971 |

(Continued)

OTHER PUBLICATIONS

U.S. Appl. No. 60/392,350, filed Jun. 28, 2002, Sommadossi.

(Continued)

*Primary Examiner* — Traviss C McIntosh, III

(74) *Attorney, Agent, or Firm* — Jones Day

(57) ABSTRACT

A method and composition for treating a host infected with hepatitis C comprising administering an effective hepatitis C treatment amount of a described 1', 2' or 3'-modified nucleoside or a pharmaceutically acceptable salt or prodrug thereof, is provided.

19 Claims, 4 Drawing Sheets

(56) References Cited

U.S. PATENT DOCUMENTS

| | | |
|---|---|---|
| 5,372,808 A | 12/1994 | Blatt et al. |
| 5,391,769 A | 2/1995 | Matsumoto et al. |
| 5,401,861 A | 3/1995 | Chou et al. |
| 5,411,947 A | 5/1995 | Hostetler et al. |
| 5,455,339 A | 10/1995 | Chu et al. |
| 5,463,092 A | 10/1995 | Hostetler et al. |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |
| 5,567,688 A | 10/1996 | Chu et al. |
| 5,587,362 A | 12/1996 | Chu et al. |
| 5,606,048 A | 2/1997 | Chou et al. |
| 5,676,942 A | 10/1997 | Testa et al. |
| 5,696,277 A | 12/1997 | Hostetler et al. |
| 5,738,845 A | 4/1998 | Imakawa |
| 5,744,600 A | 4/1998 | Mansuri et al. |
| 5,750,676 A | 5/1998 | Vorbruggen et al. |
| 5,763,418 A | 6/1998 | Matsuda et al. |
| 5,780,617 A | 7/1998 | Van den Bosch et al. |
| 5,789,608 A | 8/1998 | Glazier |
| 5,821,357 A | 10/1998 | Chou et al. |
| 5,830,455 A | 11/1998 | Valtuena et al. |
| 5,849,696 A | 12/1998 | Chretien et al. |
| 5,908,621 A | 6/1999 | Glue et al. |
| 5,928,636 A | 7/1999 | Alber et al. |
| 5,942,223 A | 8/1999 | Bazer et al. |
| 5,977,061 A | 11/1999 | De Clerq |
| 5,977,325 A | 11/1999 | McCarthy et al. |
| 5,980,884 A | 11/1999 | Blatt et al. |
| 6,002,029 A | 12/1999 | Hostetler et al. |
| 6,063,628 A | 5/2000 | Loeb et al. |
| 6,071,922 A | 6/2000 | Schinazi et al. |
| 6,140,310 A | 10/2000 | Glazier |
| 6,153,594 A | 11/2000 | Borretzen et al. |
| 6,156,501 A | 12/2000 | McGall et al. |
| 6,172,046 B1 | 1/2001 | Albrecht |
| 6,174,868 B1 | 1/2001 | Anderson et al. |
| 6,248,878 B1 | 6/2001 | Matulic-Adamic et al. |
| 6,252,060 B1 | 6/2001 | Hostetler |
| 6,271,212 B1 | 8/2001 | Chu et al. |
| 6,277,830 B1 | 8/2001 | Ganguly et al. |
| 6,284,458 B1 | 9/2001 | Anderson et al. |
| 6,312,662 B1 | 11/2001 | Erion et al. |
| 6,340,690 B1 | 1/2002 | Bachand et al. |
| 6,348,587 B1 | 2/2002 | Schinazi et al. |
| 6,369,040 B1 | 4/2002 | Acevedo et al. |
| 6,391,542 B1 | 5/2002 | Anderson et al. |
| 6,395,716 B1 | 5/2002 | Gosselin et al. |
| 6,423,489 B1 | 7/2002 | Anderson et al. |
| 6,433,159 B1 | 8/2002 | Anderson |
| 6,436,437 B1 | 8/2002 | Yatvin et al. |
| 6,444,652 B1 | 9/2002 | Gosselin et al. |
| 6,448,392 B1 | 9/2002 | Hostetler et al. |
| 6,455,508 B1 | 9/2002 | Ramasamy et al. |
| 6,455,513 B1 | 9/2002 | McGuigan et al. |
| 6,458,772 B1 | 10/2002 | Zhou et al. |
| 6,458,773 B1 | 10/2002 | Gosselin et al. |
| 6,472,373 B1 | 10/2002 | Albrecht |
| 6,495,677 B1 | 12/2002 | Ramasamy et al. |
| 6,566,344 B1 | 5/2003 | Gosselin et al. |
| 6,566,365 B1 | 5/2003 | Storer |
| 6,569,837 B1 | 5/2003 | Gosselin et al. |
| 6,573,248 B2 | 6/2003 | Ramasamy et al. |
| 6,596,700 B2 | 7/2003 | Sommadossi et al. |
| 6,599,887 B2 | 7/2003 | Hostetler et al. |
| 6,605,614 B2 | 8/2003 | Bachand et al. |
| 6,642,206 B2 | 11/2003 | Ramasamy et al. |
| 6,660,721 B2 | 12/2003 | Devos et al. |
| 6,752,981 B1 | 6/2004 | Erion et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,833,361 B2 | 12/2004 | Hong et al. |
| 6,846,810 B2 | 1/2005 | Martin et al. |
| 6,875,751 B2 | 4/2005 | Imbach et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,927,291 B2 | 8/2005 | Jin et al. |
| 6,946,115 B2 | 9/2005 | Erion et al. |
| 6,946,450 B2 | 9/2005 | Gosselin et al. |
| 6,949,522 B2 | 9/2005 | Otto et al. |
| 6,965,033 B2 | 11/2005 | Jiang et al. |
| 7,018,989 B2 | 3/2006 | McGuigan et al. |
| 7,019,135 B2 | 3/2006 | McGuigan et al. |
| 7,056,895 B2 | 6/2006 | Ramasamy et al. |
| 7,094,770 B2 | 8/2006 | Watanabe et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,138,376 B2 | 11/2006 | Gosselin et al. |
| 7,144,868 B2 | 12/2006 | Roberts et al. |
| 7,148,206 B2 | 12/2006 | Sommadossi et al. |
| 7,151,089 B2 | 12/2006 | Roberts et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldmp et al. |
| 7,285,658 B2 | 10/2007 | Cook et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,429,572 B2 | 9/2008 | Clark |
| 7,452,901 B2 | 11/2008 | Boojamra et al. |
| 7,456,155 B2 | 11/2008 | Sommadossi et al. |
| 7,534,767 B2 | 5/2009 | Butora et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,645,747 B2 | 1/2010 | Boojamra et al. |
| 7,662,798 B2 | 2/2010 | LaColla et al. |
| 7,754,699 B2 | 7/2010 | Chun et al. |
| 7,772,208 B2 | 8/2010 | Schinazi et al. |
| 7,781,576 B2 | 8/2010 | Mayes et al. |
| 7,807,653 B2 | 10/2010 | Cook et al. |
| 7,820,631 B2 | 10/2010 | McGuigan et al. |
| 7,824,851 B2 | 11/2010 | Sommadossi et al. |
| 7,842,672 B2 | 11/2010 | Boojamra et al. |
| 7,871,991 B2 | 1/2011 | Boojamra et al. |
| 7,879,815 B2 | 2/2011 | MacCoss et al. |
| 7,902,202 B2 | 3/2011 | Sommadossi et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,022,083 B2 | 9/2011 | Boojamra et al. |
| 8,119,779 B2 | 2/2012 | McGuigan et al. |
| 8,148,349 B2 | 4/2012 | Meppen et al. |
| 8,173,621 B2 | 5/2012 | Du et al. |
| 8,183,216 B2 | 5/2012 | DiFrancesco et al. |
| 8,299,038 B2 | 10/2012 | Sommadossi et al. |

(56) References Cited

U.S. PATENT DOCUMENTS

| | | |
|---|---|---|
| 8,318,682 B2 | 11/2012 | Butler et al. |
| 8,318,701 B2 | 11/2012 | Boojamra et al. |
| 8,324,179 B2 | 12/2012 | Chen et al. |
| 8,329,926 B2 | 12/2012 | Boojamra et al. |
| 8,334,270 B2 | 12/2012 | Sofia et al. |
| 8,343,937 B2 | 1/2013 | Sommadossi et al. |
| 8,415,308 B2 | 4/2013 | Cho et al. |
| 8,415,322 B2 | 4/2013 | Clark |
| 8,455,451 B2 | 6/2013 | Cho et al. |
| 8,481,713 B2 | 7/2013 | Wang et al. |
| 8,507,460 B2 | 8/2013 | Surleraux et al. |
| 8,551,973 B2 | 10/2013 | Bao et al. |
| 8,563,530 B2 | 10/2013 | Chang et al. |
| 8,569,478 B2 | 10/2013 | Du et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,716,263 B2 | 5/2014 | Chun et al. |
| 8,735,372 B2 | 5/2014 | Du et al. |
| 8,759,510 B2 | 6/2014 | Du et al. |
| 8,765,710 B2 | 7/2014 | Sofia et al. |
| 8,765,935 B2 | 7/2014 | Wagner |
| 8,816,074 B2 | 8/2014 | Chu et al. |
| 8,841,275 B2 | 9/2014 | Du et al. |
| 8,859,756 B2 | 10/2014 | Ross et al. |
| 8,877,733 B2 | 11/2014 | Cho et al. |
| 8,889,159 B2 | 11/2014 | Cleary et al. |
| 8,906,880 B2 | 12/2014 | Du et al. |
| 8,946,244 B2 | 2/2015 | Chu et al. |
| 2002/0019363 A1 | 2/2002 | Ismaili et al. |
| 2002/0035085 A1 | 3/2002 | Somadossi et al. |
| 2002/0052345 A1 | 5/2002 | Erion et al. |
| 2002/0055473 A1 | 5/2002 | Ganguly et al. |
| 2002/0055483 A1 | 5/2002 | Watanabe et al. |
| 2002/0095033 A1 | 7/2002 | Ramasamy et al. |
| 2002/0099072 A1 | 7/2002 | Bachand et al. |
| 2002/0120129 A1 | 8/2002 | Beigelman et al. |
| 2002/0127203 A1 | 9/2002 | Albrecht |
| 2002/0147160 A1 | 10/2002 | Bhat et al. |
| 2002/0156030 A1 | 10/2002 | Ramasamy et al. |
| 2002/0173490 A1 | 11/2002 | Jiang et al. |
| 2002/0198171 A1 | 12/2002 | Schinazi et al. |
| 2003/0008841 A1 | 1/2003 | Devos et al. |
| 2003/0028013 A1 | 2/2003 | Wang et al. |
| 2003/0039630 A1 | 2/2003 | Albrecht |
| 2003/0050229 A1 | 3/2003 | Sommadossi et al. |
| 2003/0053986 A1 | 3/2003 | Zahm |
| 2003/0055013 A1 | 3/2003 | Brass |
| 2003/0060400 A1 | 3/2003 | LaColla et al. |
| 2003/0083306 A1 | 5/2003 | Imbach et al. |
| 2003/0083307 A1 | 5/2003 | Devos et al. |
| 2003/0087873 A1 | 5/2003 | Stuyver et al. |
| 2003/0124512 A1 | 7/2003 | Styuver |
| 2003/0220290 A1 | 11/2003 | Gosselin et al. |
| 2003/0225028 A1 | 12/2003 | Gosselin et al. |
| 2003/0225029 A1 | 12/2003 | Stuyver et al. |
| 2003/0225037 A1 | 12/2003 | Storer et al. |
| 2003/0236216 A1 | 12/2003 | Devos et al. |
| 2004/0002476 A1 | 1/2004 | Stuyver et al. |
| 2004/0002596 A1 | 1/2004 | Hong et al. |
| 2004/0006002 A1 | 1/2004 | Sommadossi et al. |
| 2004/0014108 A1 | 1/2004 | Eldrup et al. |
| 2004/0023921 A1 | 2/2004 | Hong et al. |
| 2004/0059104 A1 | 3/2004 | Cook et al. |
| 2004/0063622 A1 | 4/2004 | Sommadossi et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Bhat et al. |
| 2004/0110718 A1 | 6/2004 | Devos et al. |
| 2004/0121980 A1 | 6/2004 | Martin et al. |
| 2004/0147464 A1 | 7/2004 | Roberts et al. |
| 2004/0229839 A1 | 11/2004 | Babu et al. |
| 2004/0229840 A1 | 11/2004 | Bhat et al. |
| 2004/0248844 A1 | 12/2004 | Ismaili et al. |
| 2004/0259934 A1 | 12/2004 | Olsen et al. |
| 2004/0266722 A1 | 12/2004 | Devos et al. |
| 2004/0266723 A1 | 12/2004 | Otto et al. |
| 2004/0266996 A1 | 12/2004 | Rabi |
| 2005/0009737 A1 | 1/2005 | Clark et al. |
| 2005/0020825 A1 | 1/2005 | Storer et al. |
| 2005/0031588 A1 | 2/2005 | Sommadossi et al. |
| 2005/0038240 A1 | 2/2005 | Connolly et al. |
| 2005/0090463 A1 | 4/2005 | Roberts et al. |
| 2005/0101550 A1 | 5/2005 | Roberts et al. |
| 2005/0107312 A1 | 5/2005 | Keicher et al. |
| 2005/0113330 A1 | 5/2005 | Imbach et al. |
| 2005/0119200 A1 | 6/2005 | Roberts et al. |
| 2005/0124532 A1 | 6/2005 | Sommadossi et al. |
| 2005/0137141 A1 | 6/2005 | Hilfinger et al. |
| 2005/0137161 A1 | 6/2005 | Sommadossi et al. |
| 2005/0215511 A1 | 9/2005 | Roberts et al. |
| 2006/0040890 A1 | 2/2006 | Martin et al. |
| 2006/0040944 A1 | 2/2006 | Gosselin et al. |
| 2006/0111311 A1 | 5/2006 | Keicher et al. |
| 2006/0166865 A1 | 7/2006 | Sommadossi et al. |
| 2006/0194835 A1 | 8/2006 | Dugourd et al. |
| 2006/0199783 A1 | 9/2006 | Wang et al. |
| 2006/0234962 A1 | 10/2006 | Olsen et al. |
| 2006/0241064 A1 | 10/2006 | Roberts et al. |
| 2006/0264389 A1 | 11/2006 | Bhat et al. |
| 2007/0004669 A1 | 1/2007 | Carroll et al. |
| 2007/0015905 A1 | 1/2007 | LaColla et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0203334 A1 | 8/2007 | Mayes et al. |
| 2007/0265222 A1 | 11/2007 | MacCoss et al. |
| 2007/0275883 A1 | 11/2007 | Sommadossi et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0280842 A1 | 11/2008 | MacCoss et al. |
| 2009/0004135 A1 | 1/2009 | Clark |
| 2009/036666 A1 | 2/2009 | Clark |
| 2009/0118223 A1 | 5/2009 | Erion et al. |
| 2010/0279969 A1 | 11/2010 | Schinazi et al. |
| 2010/0279974 A1 | 11/2010 | Pierra et al. |
| 2010/0316594 A1 | 12/2010 | Sommadossi et al. |
| 2011/0269707 A1 | 11/2011 | Stuyver et al. |
| 2011/0306541 A1 | 12/2011 | Delaney, IV et al. |
| 2011/0306573 A1 | 12/2011 | Avolio et al. |
| 2012/0010164 A1 | 1/2012 | Summa et al. |
| 2012/0107274 A1 | 5/2012 | Clarke et al. |
| 2012/0245335 A1 | 9/2012 | Clark |
| 2012/0251487 A1 | 10/2012 | Surleraux |
| 2013/0017171 A1 | 1/2013 | Sommadossi et al. |
| 2013/0064794 A1 | 3/2013 | Surlereaux et al. |
| 2013/0149283 A1 | 6/2013 | Sommadossi et al. |
| 2013/0273005 A1 | 10/2013 | Delaney et al. |
| 2013/0281686 A1 | 10/2013 | Cho et al. |
| 2013/0315862 A1 | 11/2013 | Sommadossi et al. |
| 2013/0315866 A1 | 11/2013 | Parsy et al. |
| 2013/0315867 A1 | 11/2013 | Parsy et al. |
| 2013/0315868 A1 | 11/2013 | Mayes et al. |

(56) References Cited

U.S. PATENT DOCUMENTS

| | | |
|---|---|---|
| 2013/0330297 A1 | 12/2013 | Storer et al. |
| 2014/0038916 A1 | 2/2014 | Chang et al. |
| 2014/0086873 A1 | 3/2014 | Mayes et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0140955 A1 | 5/2014 | McGuigan et al. |
| 2014/0154211 A1 | 6/2014 | Girijavallabhan et al. |
| 2014/0161770 A1 | 6/2014 | Girijavallabhan et al. |
| 2014/0178338 A1 | 6/2014 | Mayes et al. |
| 2014/0205566 A1 | 7/2014 | Liao et al. |
| 2014/0206640 A1 | 7/2014 | Girijavallabhan et al. |
| 2014/0212382 A1 | 7/2014 | Schinazi et al. |
| 2014/0248241 A1 | 9/2014 | Stewart et al. |
| 2014/0248242 A1 | 9/2014 | Dousson et al. |
| 2014/0271547 A1 | 9/2014 | Dukhan et al. |
| 2014/0294769 A1 | 10/2014 | Mayes et al. |
| 2014/0364446 A1 | 12/2014 | Dukhan et al. |
| 2015/0037282 A1 | 2/2015 | Mayes et al. |

FOREIGN PATENT DOCUMENTS

| | | |
|---|---|---|
| DE | 2122991 | 11/1972 |
| DE | 2508312 | 9/1976 |
| DE | 140254 | 2/1980 |
| DE | 3512781 | 10/1985 |
| DE | 4224737 | 2/1994 |
| DE | 102005012681 | 9/2006 |
| EP | 0 288 847 | 4/1988 |
| EP | 0 180 276 | 12/1988 |
| EP | 0 352 248 | 1/1990 |
| EP | 0 494 119 | 1/1992 |
| EP | 0 526 655 | 2/1993 |
| EP | 0 553 358 | 8/1993 |
| EP | 0 587 364 | 3/1994 |
| EP | 0 742 287 | 11/1996 |
| EP | 0 747 389 | 12/1996 |
| EP | 0 350 287 | 9/2000 |
| EP | 0 650 371 | 11/2000 |
| FR | 1521076 | 4/1968 |
| FR | 1581628 | 9/1969 |
| FR | 2662165 | 11/1991 |
| GB | 0924246 | 4/1963 |
| GB | 0984877 | 3/1965 |
| GB | 1163102 | 9/1969 |
| GB | 1163103 | 9/1969 |
| GB | 1187824 | 4/1970 |
| GB | 1209654 | 10/1970 |
| GB | 1542442 | 3/1979 |
| JP | 46021872 | 6/1971 |
| JP | 48048495 | 9/1971 |
| JP | 61212592 | 9/1986 |
| JP | 61263995 | 11/1986 |
| JP | 61263996 | 11/1986 |
| JP | 63215694 | 9/1988 |
| JP | 2091022 | 3/1990 |
| JP | 06135988 | 5/1994 |
| JP | 06211890 | 8/1994 |
| JP | 06228186 | 8/1994 |
| JP | 06293645 | 10/1994 |
| JP | 09059292 | 3/1997 |
| WO | WO 89/002733 | 4/1989 |
| WO | WO 90/000555 | 1/1990 |
| WO | WO 91/016920 | 11/1991 |
| WO | WO 91/018914 | 12/1991 |
| WO | WO 91/019721 | 12/1991 |
| WO | WO 92/015308 | 9/1992 |
| WO | WO 92/018517 | 10/1992 |
| WO | WO 93/000910 | 1/1993 |
| WO | WO 94/001117 | 1/1994 |
| WO | WO 94/026273 | 11/1994 |
| WO | WO 96/015132 | 5/1996 |
| WO | WO 97/12033 | 4/1997 |
| WO | WO 98/016184 | 4/1998 |
| WO | WO 98/30223 | 7/1998 |
| WO | WO 99/015194 | 4/1999 |
| WO | WO 99/023104 | 5/1999 |
| WO | WO 99/043691 | 9/1999 |
| WO | WO 99/045016 | 9/1999 |
| WO | WO 99/052514 | 10/1999 |
| WO | WO 99/059621 | 11/1999 |
| WO | WO 99/064016 | 12/1999 |
| WO | WO 00/009531 | 2/2000 |
| WO | WO 00/025799 | 5/2000 |
| WO | WO 00/037110 | 6/2000 |
| WO | WO 00/052015 | 9/2000 |
| WO | WO 01/018013 | 3/2001 |
| WO | WO 01/032153 | 5/2001 |
| WO | WO 01/047935 | 7/2001 |
| WO | WO 01/049700 | 7/2001 |
| WO | WO 01/060315 | 8/2001 |
| WO | WO 01/068663 | 9/2001 |
| WO | WO 01/079246 | 10/2001 |
| WO | WO 01/081359 | 11/2001 |
| WO | WO 01/090121 | 11/2001 |
| WO | WO 01/091737 | 12/2001 |
| WO | WO 01/092282 | 12/2001 |
| WO | WO 01/096353 | 12/2001 |
| WO | WO 02/003997 | 1/2002 |
| WO | WO 02/18369 | 3/2002 |
| WO | WO 02/018404 | 3/2002 |
| WO | WO 02/032414 | 4/2002 |
| WO | WO 02/032920 | 4/2002 |
| WO | WO 02/048165 | 6/2002 |
| WO | WO 02/057287 | 7/2002 |
| WO | WO 02/057425 | 7/2002 |
| WO | WO 02/070533 | 9/2002 |
| WO | WO 02/094289 | 11/2002 |
| WO | WO 02/100415 | 12/2002 |
| WO | WO 03/024461 | 3/2003 |
| WO | WO 03/026589 | 4/2003 |
| WO | WO 03/026675 | 4/2003 |
| WO | WO 03/039523 | 5/2003 |
| WO | WO 03/051899 | 6/2003 |
| WO | WO 03/061385 | 7/2003 |
| WO | WO 03/061576 | 7/2003 |
| WO | WO 03/062255 | 7/2003 |
| WO | WO 03/062256 | 7/2003 |
| WO | WO 03/062257 | 7/2003 |
| WO | WO 03/063771 | 8/2003 |
| WO | WO 03/068162 | 8/2003 |
| WO | WO 03/068164 | 8/2003 |
| WO | WO 03/068244 | 8/2003 |
| WO | WO 03/072757 | 9/2003 |
| WO | WO 03/093290 | 11/2003 |
| WO | WO 03/099840 | 12/2003 |
| WO | WO 03/100017 | 12/2003 |
| WO | WO 03/105770 | 12/2003 |
| WO | WO 03/106577 | 12/2003 |
| WO | WO 04/000858 | 12/2003 |
| WO | WO 04/002422 | 1/2004 |
| WO | WO 04/002999 | 1/2004 |
| WO | WO 04/003000 | 1/2004 |
| WO | WO 04/003138 | 1/2004 |
| WO | WO 04/007512 | 1/2004 |
| WO | WO 04/009020 | 1/2004 |
| WO | WO 04/023921 | 3/2004 |
| WO | WO 04/028481 | 4/2004 |
| WO | WO 04/041203 | 5/2004 |
| WO | WO 04/043977 | 5/2004 |
| WO | WO 04/043978 | 5/2004 |
| WO | WO 04/044132 | 5/2004 |
| WO | WO 04/046159 | 6/2004 |
| WO | WO 04/046331 | 6/2004 |
| WO | WO 04/052899 | 6/2004 |
| WO | WO 04/058792 | 7/2004 |
| WO | WO 04/065398 | 8/2004 |
| WO | WO 04/072090 | 8/2004 |
| WO | WO 04/080466 | 9/2004 |
| WO | WO 04/084796 | 10/2004 |

(56) References Cited

FOREIGN PATENT DOCUMENTS

| WO | WO 04/096149 | 11/2004 |
|---|---|---|
| WO | WO 04/106356 | 12/2004 |
| WO | WO 05/003147 | 1/2005 |
| WO | WO 05/012327 | 2/2005 |
| WO | WO 05/020884 | 3/2005 |
| WO | WO 05/020885 | 3/2005 |
| WO | WO 05/021568 | 3/2005 |
| WO | WO 05/030258 | 4/2005 |
| WO | WO 05/042556 | 5/2005 |
| WO | WO 05/123087 | 12/2005 |
| WO | WO 06/002231 | 1/2006 |
| WO | WO 06/012078 | 2/2006 |
| WO | WO 06/012440 | 2/2006 |
| WO | WO 06/016930 | 2/2006 |
| WO | WO 06/037028 | 4/2006 |
| WO | WO 06/037227 | 4/2006 |
| WO | WO 06/063717 | 6/2006 |
| WO | WO 06/065335 | 6/2006 |
| WO | WO 06/097323 | 9/2006 |
| WO | WO 06/100087 | 9/2006 |
| WO | WO 06/121820 | 11/2006 |
| WO | WO 06/130532 | 12/2006 |
| WO | WO 07/011777 | 1/2007 |
| WO | WO 07/025304 | 1/2007 |
| WO | WO 14/059901 | 4/2014 |
| WO | WO 14/059902 | 4/2014 |
| WO | WO 14/204831 | 12/2014 |

OTHER PUBLICATIONS

U.S. Appl. No. 60/446,194, filed Apr. 28, 2003, Sommadossi.
U.S. Appl. No. 60/470,949, filed May 14, 2003, Sommadossi.
U.S. Appl. No. 60/474,368, filed May 30, 2003, Clark.
U.S. Appl. No. 10/608,907, filed Jun. 27, 2003, Sommadossi.
U.S. Appl. No. 11/854,218, field Sep. 12, 2007, Clark.
U.S. Appl. No. 12/131,868, filed Jun. 2, 2008, Sommadossi.
U.S. Appl. No. 12/878,262, filed Sep. 9, 2010, Clark.
16th International Conference on Antiviral Research (Apr. 27, 2003), Savannah, Ga., pp. A75-A77.
2nd Declaration of Christoph Seeger, Ph.D. dated Nov. 28, 2012.
2nd Declaration of Victor E. Marquez, Ph.D. dated Nov. 28, 2012.
Afdhal, et al., "Enhanced Antiviral Efficacy for Valopicitabine Plus PEG-Interferon in Hepatitis C Patients with HCV Genotype-1 Infection," J. Hepatol., 42:39-40 (2005).
Alt, et al., "Specific Inhibition of Hepatitis C Viral Gene Expression by Antisense Phosphorothioate Oligodeoxynucleotides," Hepatology, 22:707-717 (1995).
Alt, et al., "Core Specific Antisense Phosphorothioate Oligodeoxynucleotides as Potent and Specific Inhibitors of Hepatitis C Viral Translation," Arch. Virol., 142:589-599 (1997).
Aparicio, et al., "Synthesis of Saccarinic Acid Derivatives," Carbohydrate Res., 129:99-109 (1984).
Apath.com webpage at http://www.apath.com/Blazing_Blight_7.htm.
Awad, Laila Fathy, et al., A Synthesis of Methyl 3-O-(β-D-Mannopyranosyl)-α-Dmannopyranoside from Sulfonate Intermediates, Bull. Chem. Soc. Jpn., vol. 59, pp. 1587-1592 (1986).
Awano, et al., "Synthesis and Antiviral Activity of 5-Substituted (2' S)-2'-Deoxy-2'-C-Methylcytidines and -Uridines," Arch. Pharm. 329:66-72 (1996).
Baginski, et al., "Mechanism of Action of a Pestivirus Antiviral Compound," Proc. Natl. Acad. Sci. U.S.A., 97:7981-7986 (2000).
Bartenschlager and Lohmann, Antiviral Res. 52: 1-17 (2001).
Battaglia, et al., "Combination Therapy with Interferon and Ribavirin in the Treatment of Chronic Hepatitis C Infection," Ann. Pharmacother, 34:487-494 (2000).
Beard et al., Hepatology 30: 316-24 (1999).
Beauchamp, L.M., et al., Amino Acid Ester Prodrugs of Acyclovir, Antiviral Chemistry & Chemotherapy, vol. 3, No. 3, pp. 157-164 (1992).
Behrens et al., EMBO J. 15: 12-22 (1996).

Beigelman et al., "Epimerization During the Acetolysis of 3-O-Acetyl-5-O-Benzoy 1-1,2-O-Isopropylidene-3-C-Methyl-α-D-Ribofuranose. Synthesis of 3'-C-Methylnucleosides with the β-D-ribo- and α-D-arabino Configurations," Carbohydrate Res., 181:77-88 (1988).
Beigelman, et al., "A General Method for Synthesis of 3'-Alkylnucleosides," Nucleic Acids Symp. Ser., 9:115-118 (1981).
Beigelman, et al., "Functionally Complete Analogs of Nucleosides. The Use of D-Glucose for the Synthesis of 2-C-Methyl-D-Ribose Derivatives and Related Nucleosides," Bioorg. Khim., 12:1359-1365 (1986).
Beigelman, et al., "New Synthesis of 2'-C-Methylnucleosides Starting from D-Glucose and D-Ribose," Carbohydrate Res., 166:219-232 (1987).
Berenguer, et al., "Hepatitis B and C Viruses: Molecular Identification and Targeted Antiviral Therapies," Proc. Asso. Am. Physicians, 110:98-112 (1998).
Berenguer, et al., "Hepatitis C Virus in the Transplant Setting," Antivir. Ther., 3:125-136 (1998).
Berman, et al., "Synergistic Cytotoxic Effect of Azidothymidine and Recombinant Interferon Alpha on Normal Human Bone Marrow Progenitor Cells," Blood, 74:1281-1286 (1989).
Bhopale, et al., "Emerging Drugs for Chronic Hepatitis C," Hepatol. Res. 32:146-153 (2005).
Bianco, et al., "Synthesis of a New Carbocyclic Nucleoside Analog," Tetrahedron Lett., 38:6433-6436 (1997).
Billich, et al., "Nucleoside Phosphotransferase from Malt Sprouts," Biol. Chem. Hoppe-Seyler, 367:267-278 (1986).
Bio, et al., "Practical Synthesis of a Potent Hepatitis C Virus RNA Replication Inhibitor," J. Org. Chem., 69:6257-6266 (2004).
Blight et al., Science 290: 1972-74 (2000).
Bloch, A., et al., "The Role of the 5'-Hydroxyl Group of Adenosine in Determining Substrate Specificity for Adenosine Deaminase," J. Med. Chem., 10:908-12 (1967).
Bourne, Nigel, et al., Screening for Hepatitis C Virus Antiviral SctivityWith a Cell-based Secreted Alkaline Phosphatase Reporter Replicon System, Antiviral Research, vol. 67, pp. 76-82 (2005).
Briot, Anne, et al., Benzylsulfonyl: A Valuable Protecting and Deactivating Group in Phenol Chemistry, Tetrahedron Letters, vol. 44, pp. 965-967 (2003).
Browne, et al., "2',3'-Didehydro-3'-Deoxythymidine (d4T) in Patients with AIDS or AIDS-Related Complex: A Phase I Trial," J. Infect. Dis., 167:21-29 (1993).
Bryant, et al., "Antiviral L-Nucleosides Specific for Hepatitis B Virus Infection," Antimicrob. Agents Chemother., 45:229-235 (2001).
Buckwold, et al., "Bovine viral diarrhea virus as a surrogate model of hepatitis C virus for the evaluation of antiviral agents." Antiviral Research, 60: 1-15 (2003).
*Calif. Inst. of Technol. v. Enzo Life Sciences, Inc.*, Interference 105,496, Paper 120 (BPAI Sep. 22, 2010).
Cappellacci, et al., "Ribose-Modified Nucleosides as Ligands for Adenosine Receptors: Synthesis, Conformational Analysis, and Biological Evaluation of 1'-C-Methyl Adenosine Analogues," J. Med. Chem., 45:1196-1202 (2002).
Cappellacci, et al., "Synthesis, Biological Evaluation, and Molecular Modeling of Ribose-Modified Adenosine Analogues as Adenosine Receptor Agonists," J. Med. Chem., 48:1550-1562 (2005).
Carroll and LaFemina, Antiviral Research: Strategies in Antiviral Drug Discovery 153-166 (Robert L. LaFemina, Ph.D., ed., 2009).
Carroll, "Nucleoside Analog Inhibitors of Hepatitis C Virus Replication," Infectious Disord. Drug Targets 6:17-29 (2006).
Carroll, et al., "Inhibition of Hepatitis C Virus RNA Replication by 2'-Modified Nucleoside Analogs," J. Biol. Chem., 278 11979-11984 (2003).
Cavelier, et al., "Studies of Selective Boc Removal in the Presence of Silyl Ethers," Tetrahedron Lett., 37:5131-5134 (1996).
Chand, et al., "Synthesis of (2S,3S,4R,5R)-2-(4- Amino-5H-Pyrrolo[3,2-d]Pyrimidin-7-yl)-5-(Hydroxymethyl)-3-Methylpyrrolidine-3,4-Diol, An Analog of Potent HCV Inhibitor," Collection Symposium Series 7 (Chemistry of Nucleic Acid Components), pp. 329-332 (2005).

(56) References Cited

OTHER PUBLICATIONS

Chiacchio, et al., "Stereoselective Synthesis of 2'-Amino-2',3'-Dideoxynucleosides by Nitron 1,3-Dipolar Cycloaddition: A New Efficient Entry Toward d4T and its 2-Methyl Analogue," J. Org. Chem., 64:28-36 (1999).
Chiaramonte, et al., "Inhibition of CMP-Sialic Acid Transport into Golgi Vesicles by Nucleoside Monophates," Biochemistry, 40:14260-14267 (2001).
Choi, Yongseok, et al., A Conformationally Locked Analogue of the Anti-HIV Agent Stavudine. An Important Correlation between Pseudorotation and Maximum Amplitude, J. Med. Chem., vol. 46, pp. 3292-3299 (2003).
Chu et al., FEMS Microbiology Letters 202: 9-15 (2001).
Clark, et al., "Design, Synthesis, and Antiviral Activity of 2'-Deoxy-2'-Fluoro-2'-C-Methylcytidine, a Potent Inhibitor of Hepatitis C Vims Replication," J. Med. Chem., 48:5504-5508 (2005).
Clark, et al., "Synthesis and Antiviral Activity of 2'-Deoxy-2'-Fluoro-2'-C-Methyl purine Nucleosides as Inhibitors of Hepatitis C Virus RNA Replication.," Bioorg. Med. Chem. Lett., 16:1712-1715 (2006).
Clark, Jeremy L., et al., Synthesis of 2-Deoxy-2-Fluoro-2-C- Methyl-DRibofuranoses, Journal of Carbohydrate Chemistry, vol. 25, pp. 461-470 (2006).
Clarke, Baillière's Clin. Gastroenterol. 14: 293-305 (2000).
Codington et al., "Synthesis of 2'-Fluorothymidine, 2'-Fluorodeoxyuridine, and Other 2'-Halogeno-2'-Halogeno-2'-Deoxy Nucleosides," J. Org. Chem., 29:558 (1964).
Coelmont, et al., "Ribavirin Antagonizes the In Vitro Anti-Hepatitis C Virus Activity of 2'-C-Methylcytidine, The Active Component of Valopicitabine," Antimicrob. Agents Chemother., 50:3444-3446 (2006).
Cohen, Science 285: 26-30 (1999).
Colacino, "Mechanisms for the Anti-Hepatitis B Virus Activity and Mitochondrial Toxicity of Fialuridine (FIAU)," Antiviral Res., 29:125-139 (1996).
Commentary, Science 285: 9 (1999).
Condit, R.C., Principles of Virology (Chapter 2), in Knipe, D.M. et al., eds., Fields Virology, Fourth Edition, Philadelphia, Lippincott Williams & Wilkins (2001).
Condit, R.C., Principles of Virology (Chapter 2), in Knipe, D.M. et al., eds., Fields Virology, Fifth Edition, Philadelphia, Lippincott Williams & Wilkins (2007).
Cook, "Improving the Treatment of Hepatitis C Infection in the UK," Expert Opin. Pharmacother., 8:183-191 (2007).
Cornberg, et al., "Present and Future Therapy for Hepatitis C Virus," Expert Rev. Antiinfect Ther., 4:781-793 (2006).
Cox et al., Principles of Biochemistry, p. 330 (1993).
Cramer and Pfleiderer, Helvetica Chimica Acta 79: 2114-2136 (1996).
Cretton-Scott, et al., "Pharmacokinetics of β-L-2'-Deoxycytidine Prodrugs in Monkeys," Antiviral Res., 50:A44 (2001).
Cui, et al., "Cellular and Molecular Events Leading to Mitochondrial Toxicity of 1-(2-Deoxy-2-Fluoro-1-β-D-Arabinofuranosyl)-5-Iodouracil in Human Liver Cells," J. Clin. Invest., 95:555-563 (1995).
Czernecki, et al., "Synthesis of 2'-Deoxy-2'-Spirocyclopropyl Cytidine as Potential Inhibitor of Ribonucleotide Diphosphate Reductase," Can. J. Chem., 71:413-416 (1993).
Czernecki, et al., "Synthesis of Various 3'-Branched 2',3'-Unsaturated Pyrimidine Nucleosides as Potential Anti-HIV Agents," J. Org. Chem., 57:7325-7328 (1992).
Dalpiaz, et al., "Temperature Dependence of the Affinity Enhancement of Selective Adenosine A1 Receptor Agonism: A Thermodynamic Analysis," Eur. J. Pharmacol., 448:123-131 (2002).
Damha et al., Curr. Protocols in Nucleic Acid Chem.: 1.7.1-1.7.19 (2002).
Damha et al., J. Org. Chem., 71(3): 921-925 (2006).
Damha et al., Nucleosides, Nucleotides & Nucleic Acids 22: 1343-1346 (2003).
Daniels et al., "Tautomerism of Uracil and Thymine in Aqueous Solution: Spectroscopic Evidence," Proc. Nat. Acad. Sci. U.S.A., 69:2488-2491 (1972).

Davis, "Current Therapy for Chronic Hepatitis C," Gastroenterology 118:S104-S114 (2000).
Davis, "New Therapies: Oral Inhibitors and Immune Modulators," Clin. Liver Dis., 10:867-880 (2006).
Davisson, et al., "Synthesis of Nucleotide 5'-Diphosphates from 5'-O-Tosyl Nucleosides," J. Org. Chem., 52:1794-1801(1987).
De Clercq, J. Clin. Viology 22:73-89 (2001).
De Francesco and Rice, "New therapies on the horizon for hepatitis C: are we close?," Clin. Liver Dis., 7:211-242 (2003).
De Francesco, et al., "Approaching a New Era for Hepatitis C Virus Therapy: Inhibitors of the NS3-4A Serine Protease and the NS5B RNA-Dependent RNA Polymerase," Antiviral Res., 58:1-16 (2003).
Declaration and Curriculum Vitae of Jean-Pierre Sommadossi, Ph.D., Interference No. 103,906, Apr. 3, 1998.
Delombaert, et al., "N-Phosphonomethyl Dipeptides and Their Phosphonate Prodrugs, a New Generation of Neutral Endopeptidase (NEP, EC 3.4.24.11) Inhibitors," J. Med. Chem., 37:498-511 (1994).
Désiré and Prandi, Carbohydrate Research 317: 110-118 (1999).
Dhanak, D et al., Identification and Biological Characterization of Heterocyclic Inhibitors of the Hepatitis C Virus RNA-dependent RNA Polymerase, J. Biol. Chem. vol. 277, No. 41, pp. 38322-38327 (2002).
Di Bisceglie and Bacon, Sci. Am. 281: 80-85 (1999).
Di Bisceglie, Hepatology 35:224-31 (2002).
Diamond et al., J. Virol. 74: 4957-66 (2000).
Ding, et al., "Synthesis of 2'β-C-Methyl Toyocamycin and Sangivamycin Analogs As Potential HCV Inhibitors," Bioorg. Med. Chem. Lett., 15:725-727 (2005).
Ding, et al., "Synthesis of 9-(2-β-C-Methyl-β-D-Ribofuranosyl)-6-Substituted Purine Derivatives as Inhibitors of HCV RNA Replication," Bioorg. Med. Chem. Lett., 15:709-713 (2005).
Dornsife, et al., "In Vitro Potency of Inhibition by Antiviral Drugs of Hematopoietic Progenitor Colony Formation Correlates with Exposure at Hemotoxic Levels in Human Immunodeficiency Virus-Positive Human," Antimicrob. Agents Chemother., 40:514-519 (1996).
Dutartre, et al., "General Catalytic Deficiency of Hepatitis C Virus RNA Polymerase with an S282T Mutation and Mutually Exclusive Resistance towards 2'-Modified Nucleotide Analogues," Antimicrob. Agents Chemother., 50:4161-4169 (2006).
Dymock, et al., "Novel Approaches to the Treatment of Hepatitis C Virus Infection," Antiviral Chem. Chemother., 11:79-95 (2000).
Eldrup, et al., "Structure-Activity Relationship of Heterobase-Modified 2'-C-Methyl Ribonucleosides as Inhibitors of Hepatitis C Virus RNA Replication," J. Med. Chem. 47:5284-5297 (2004).
Eldrup, et al., "Structure-Activity Relationship of Purine Ribonucleosides for Inhibition of Hepatitis C Virus RNA-Dependent RNA Polymerase,", J. Med. Chem., 47:2283-2295 (2004).
European Patent Appln. No. 03761744 Office Action dated Apr. 16, 2012.
Faivre-Buet, et al., "Synthesis of 1'-Deoxypsicofuanosyl-Deoxynucleosides as Potential Anti-HIV Agents," Nucleosides Nucleotides, 11:1411-1424 (1992).
Farkas, et al., "Nucleic acid Components and Their Analogues. LXXIX. Synthesis of Methyl 1-Deoxy-D-Psicofuranosides Substituted at C(1) With Halo Atoms or a Mercapto Group," Collect. Czech. Chem. Commun., 31:1535-1543 (1996).
Farkas, et al., "Nucleic Acid Components and Their Analogues. XCIV. Synthesis of 6-Amino-9-(1-Deoxy-β-D-Psicofuranosyl)purine," Collect. Czech. Chem. Commun., 32:2663-2667 (1967).
Farquhar et al., "Biologically Reversible Phosphate-Protective Groups," J. Pharm. Sci., 72(3):324 (1983).
Farquhar, et al., "Synthesis and Biological Evaluation of 9-[5'-(2-Oxo-1,3,2-Oxazaphosphorinan-2-yl-)-β-D-Arabinosyl]Adenine and 9-[5'-(2-Oxo-1,3,2-Dioxazaphosphorinan-2-yl)-β-D-Arabinosyl]Adenine: Potential Neutral Precursors of 9-4[β-D-Arabinofuranosyl]Adenine 5'-Monophosphate," J. Med. Chem., 28:1358-1381 (1985).
Farquhar, et al., "Synthesis and Biological Evaluation of Neutral Derivatives of 3-Fluoro-2'-Deoxyuridine 5'-Phosphate," J. Med. Chem., 26:1153-1158 (1983).
Feast, et al., "Studies on the D-Glucosaccharinic Acids," Acta Chem. Scand., 19(5):1127-1134 (1965).

(56) References Cited

OTHER PUBLICATIONS

Fedorov, et al., "3'-C-Branched 2'-Deoxy-S-Methyluridines: Synthesis, Enzyme Inhibition, and Antiviral Properties," J. Med. Chem., 35:4567-4575 (1992).
Ferrari et al., J. Virol. 73: 1649-54 (1999).
Ferrari, et al., "Characterization of Soluble Hepatitis C Virus RNA-Dependent RNA Polymerase Expressed in Escherichia coli," J. Virol., 73:1649-1654 (1999).
Final Office Action dated Aug. 22, 2007 from U.S. Appl. No. 10/602,691.
Final Office Action dated Aug. 29, 2011 from U.S. Appl. No. 12/504,601.
Final Office Action dated Oct. 7, 2008 from U.S. Appl. No. 10/602,691.
Fischl, et al., "Zalcitabine Compared with Zidovudine in Patients with Advanced HIV-1 Infection Who Received Previous Zidovudine Therapy," Ann. Intern. Med., 18:762-769 (1993).
Fournier-Caruana et al., Biologicals 28: 33-40 (2000).
Fox, et al., "Thiolation of Nucleosides. II. Synthesis of 5-Methyl-2'-Deoxycytidine and Related Pyrimidine Nucleosides," J. Am. Chem. Soc., 81:178-187 (1959).
Franchetti, et al., "2'-C-Methyl Analogues of Selective Adenosine Receptor Agonists: Synthesis and Binding Studies," J. Med. Chem., 41:1708-1715 (1998).
Franchetti, et al., "Antitumor Activity of C-Methyl-β-D-Ribofuranosyladenine Nucleoside Ribonucleotide Reductase Inhibitors," J. Med. Chem., 48, 4983-4989 (2005).
Freed, et al., "Evidence for Acyloxymethyl Esters of Pyrimidine 5'-Deoxyribonucleotides as Extracellular Sources of Active 5'-Deoxyribonucleotides in Cultured Cells," Biochem. Pharmacol., 38:3193-3198 (1989).
Frese et al., Hepatology 35:694-703 (2002).
Frese et al., J. Gen. Virol. 82: 723-33 (2001).
Friebe et al., J. Virol.75: 12047-57 (2001).
Fujimori, et al., "A Convenient and Stereoselective Synthesis of 2'-Deoxy-β-L-Nucleosides," Nucleosides Nucleotides, 11:341-349 (1992).
Furman et al., Antiviral Res. 91: 120-132 (2011).
Furukawa, et al.,. "A Novel Method for Synthesis of Purine Nucleosides Using Friedel-Crafts Catalysts," Chem. Pharm. Bull., 16:1076-1080 (1968).
Galderisi, et al., "Antisense Oligonucleotides as Therapeutic Agents," J. Cell. Physiol., 181:251-257 (1999).
Gallo, et al., "2'-C-Methyluridine Phosphoramidite: A New Building Block for the Preparation of RNA Analogues Carrying the 2'-Hydroxyl Group," Tetrahedron, 57:5707-5713 (2001).
GenBank accession No. AJ242652 at http://www.ncbi.nlm.nih.gov/nuccore/5441834?sat=8&satkey=803423.
*Genentech, Inc.* v. *Chiron Corp.*, Interference 105,048, Paper 258 (BPAI Nov. 30, 2004) (non-precedential).
Gerotto, et al., "Effect of Retreatment with Interferon Alone or Interferon Plus Ribavirin on Hepatitis C Virus Quasispecies Diversification in Nonresponder Patients with Chronic Hepatitis C," J. Virol., 73:7241-7247 (1999).
Girardet, et al., "Synthesis and Cytotoxicity of 4-Amino-5-Oxopyrido[2,3-d]Pyrimidine Nucleosides," J. Med. Chem., 43:3704-3713 (2000).
*Goeddel* v. *Sugano* Interference 105,334, Paper 109, at 40-42 (BPAI Sep. 29, 2008), rev'd on other grounds, 617 F.3d 1350 (Fed. Cir. 2010).
Goldman, Bruce, Potential New Class of Drugs to Combat Hepatitis C Identified by Scientists, Stanford School of Medicine, http://med.stanford.edu/ism/2010/january/glenn.html (Jan. 20, 2010).
Grakoui et al., Hepatology 33: 489-95 (2001).
Greene and Wuts, Protective Groups in Organic Synthesis (3rd ed.): 76-81, 95-96, 102-106, 150, 173176 and 197-198 (1999).
Gretch, "Use and Interpretation of HCV Diagnostic Tests in the Clinical Setting," Clinics in Live Disease, 1:547-557 (1997).
Grouiller, et al., "Novel-p-Toluenesulfonylation and Thionocarbonylation of Unprotected Thymine Nucleosides," Synlett, 1993:221-222 (1993).

Grouiller, et al., "Structural Studies on a Psicofuranosyl Nucleoside, a Potential Antiviral Agent," J. Pharm. Belg., 47:381-383 (1992).
Grunnagel, et al., "Preparation of D-Tagatose," Justus Liebigs Annalen der Chemie, 721:234-235 (1969).
Gunic, et al., "Synthesis and Cytotoxity of 4'-C- and 5'-C-Substituted Toyocamycins," Bioorg. Med. Chem., 9:163-170 (2001).
Guo, J.-T., Bichko, V.V., Seeger, C., Effect of Alpha Interferon on the Hepatitis C Virus Replicon, J. Virol., vol. 75, pp. 8516-8523 (2001).
Haraguchi, et al., "Stereoselective Synthesis of 1'-C-Branched Uracil Nucleosides from Uridine," Nucleotides Nucleosides , 14:417-420 (1995).
Haraguchi, et al., Preparation and Reactions of 2'- and 3'-Vinyl Bromides of Uracil Nucleosides: Versatile Synthons for Anti-HIV Agents, Tetrahedron Lett., 32:3391-3394 (1991).
Harrison, Steadman D., et al., Therapeutic Synergism of Tiazofurin and Selected Antitumor Drugs against Sensitive and Resistant P388 Leukemia in Mice, Cancer Research, vol. 46, pp. 3396-3400 (1986).
Harry-O'Kuru, et al., "2'-C-alkylribonucleosides: Design, Synthesis and Conformation," Nucleosides Nucleotides, 6:1457-1460 (1997).
Harry-O'Kuru, et al., "A Short, Flexible Route Toward 2'-C-Branched Ribonucleosides," J. Org. Chem., 62:1754-1759 (1997).
Hassan, et al., "Nucleosides and Nucleotides 151: Conversion of (Z)-2'-(Cyanomethylene)-2'-Deoxyuridines into Their (E)-Isomers via Addition of Thiophenol to the Cyanomethylene Moiety Followed by Oxidative Syn-Elimination Reactions," J. Org. Chem., 61. 6261-6267 (1996).
Hassan, et al., "Nucleosides and Nucleotides 156: Chelation-Controlled and Nonchelation-Controlled Diastereofacial Selective Thiophenol Addition Reactions at the 2'-Position of 2'-[(Alkoxycarbonyl)Methylene]-2'-Deoxyuridines: Conversion of (Z)-2'[(Alkoxycarbonyl)Methylene]-2'-Deoxyuridines into Their (E)-Isomers," J. Org. Chem., 62:11-17 (1997).
Hattori, et al., "Nucleosides and Nucleotides 158. 1-(3-C-Ethynyl-β-D-Ribo-Pentofuranosyl)-Cytosine, 1-(3-C-Ethynyl-β-D-Ribo-Pentofuranosyl)Uracil, and Their Nucleobase Analogues as New Potential Multifunctional Antitumor Nucleosides with a Broad Spectrum of Activity," J. Med. Chem., 39:5005-5001 (1996).
Hattori, et al., "Nucleosides and Nucleotides 175. Structural Requirements of the Sugar Moiety for the Antitumor Activities of New Nucleoside Antimetabolites, 1-(3-C-Ethynyl-β-D-Ribo-Pentofuranosyl)Cytosine and -Uracil," J. Med. Chem., 41:2892-2902 (1998).
Hayakawa, et al., "Reaction of Organometallic Reagents with 2'- and 3'-Ketouridine Derivatives: Synthesis of Uracil Nucleosides Branched at the 2'- and 3'-Positions," Chem. Pharm. Bull., 35:2605-2608 (1987).
Hirooka et al., Bull. Chem. Soc. Jpn. 74(9): 1679-1694 (2001).
Hoard, et al., "Conversion of Mono- and Oligodeoxyribonucleotides to 5'-Triphosphates," J. Am. Chem. Soc., 87:1785-1788 (1965).
Hodge, et al., "Amadori Rearrangement Products," Meth. Carbohydrate Chem., 2:99-107 (1963).
Holy, "Nucleic Acid Components and Their Analogs. CLIII. Preparation of 2'-Deoxy-L-Ribonucleosides for the Pyrimidine Series," Collect. Czech. Chem. Commun., 37:4072-4087 (1972).
Hong et al., Virology 256: 36-44 (1999).
Hossain, et al., "Synthesis of 2'- and 3'-Spiro-Isoxazolidine Derivatives of Thymidine & Their Conversions to 2',3'-Dideoxy-2',3'-Didehydro-3'-C-Substituted Nucleosides by Radical Promoted Fragmentation," Tetrahedron, 49:10133-10156 (1993).
Hostetler, et al., "Greatly Enhanced Inhibition of Human Immunodeficiency Virus Type I Replication in CEM and HT4-6C Cells by 3'-Deoxythymidine Diphosphate Dimyristoylglycerol, a Lipid Prodrug of 3'-Deoxythymidin," Antimicrob. Agents Chemother., 36:2025-2029 (1992).
Hostetler, et al., "Synthesis and Antiretroviral Activity of Phospholipids Analogs of Azidothymidine and Other Antiviral Nucleosides," J. Biol. Chem., 265:6112-6117 (1990).
Hostetler, Karl Y., et al., Synthesis and Antiretroviral Activity of Phospholipid Analogs of Azidothymidine and Other Antiviral Nucleosides, The Journal of Biological Chemistry, vol. 265, No. 11, pp. 6112-6117 (1990).

(56) References Cited

OTHER PUBLICATIONS

Hrebabecky, et al., "Nucleic Acid Components and Their Analogs: CXLIX: Synthesis of Pyrimidine Nucleosides Derived from 1-Deoxy-D-Psicose," Collect. Czech. Chem. Commun., 37:2059-2064 (1974).
Hrebabecky, et al., "Synthesis of 7- and 9β-D-Psicofuranosylguanine and Their l'-Deoxy Derivatives," Collect. Czech. Chem. Commun., 39:2115-2123 (1974).
Hu, et al., "Viral, Host and Interferon-Related Factors Modulating the Effect of Interferon Therapy for Hepatitis C Virus Infection," J. Viral Hepatitis, 8:1-18 (2001).
*Hudziak* v. *Ring*, Interference 105,266, 2005 WL 3694322 (BPAI 2005).
Hunston, et al., "Synthesis and Biological Properties of Some Cyclic Phosphotriesters Derived from 2'-Deoxy-5-Fluorouridine," J. Med. Chem., 27:440-444 (1984).
Husson van Vilet, Biologicals 18: 25-27 (1990).
Iglesias, et al., "Complete and Regioselective Deacetylation of Peracetylated Uridines Using a Lipase," Biotech. Lett., 22:361-365 (2000).
Iimori, et al., "2'-C-, 3'-C-, and 5'-C-Methylsangivamycins: Conformational Lock with the Methyl Group," Tetrahedron Lett., 32, 7273-7276 (1991).
Iino et al., "Nucleosides and Nucleotides 139. Stereoselective Synthesis of (2'S)-2'-C-Alkyl-2'-Deoxyuridines," Nucleosides Nucleotides, 15:169-181 (1996).
Ikeda et al., J. Virol. 76: 2997-3006 (2002 (received Oct. 3, 2001, accepted for publication Dec. 20, 2001).
Ikegashira, et al., "Discovery of Conformationally Constrained Tetracylic Compounds as Potent Hepatitis C Virus NSSB RNA Polymerase Inhibitors," J. Med. Chem., 449:6950-6953 (2006).
Mai, K., et al., "Studies on Phosphorylation. IV. Selective Phosphorylation of the Primary Hydroxyl Group in Nucleosides," J. Org. Chem., 34:1547-1550 (1969).
Interference 105,871, Appearance record dated Jan. 7, 2014.
Interference 105,871, Clark Clean Copy of Claims dated Mar. 7, 2012.
Interference 105,871, Clark Corrected Reply 1 dated Oct. 11, 2012.
Interference 105,871, Clark Corrected Reply 6 dated Oct. 11, 2012.
Interference 105,871, Clark exhibit list 9 dated Jun. 10, 2013.
Interference 105,871, Clark exhibit list for priority record dated Dec. 4, 2013.
Interference 105,871, Clark filing of demonstrative exhibits dated Jan. 3, 2014.
Interference 105,871, Clark Final Exhibit List dated Nov. 28, 2012.
Interference 105,871, Clark final exhibit list-priority phase dated Nov. 7, 2013.
Interference 105,871, Clark List of Intended Motions dated Apr. 11, 2012.
Interference 105,871, Clark miscellaneous motion 10 dated Oct. 18, 2013.
Interference 105,871, Clark Miscellaneous Motion 7 dated Oct. 23, 2012.
Interference 105,871, Clark miscellaneous motion 8 dated Jun. 10, 2013.
Interference 105,871, Clark Notice 2 dated Aug. 14, 2012.
Interference 105,871, Clark Notice dated May 31, 2012.
Interference 105,871, Clark Notice of Change in Related Proceedings dated Jul. 6, 2012.
Interference 105,871, Clark notice of judicial review dated Mar. 31, 2014.
Interference 105,871, Clark notice of related proceedings 2 dated Apr. 11, 2013.
Interference 105,871, Clark Notice of Related Proceedings dated Mar. 7, 2012.
Interference 105,871, Clark notice of service of supplemental evidence 4 dated Jul. 10, 2013.
Interference 105,871, Clark notice of service of supplemental evidence 5 dated Jul. 12, 2013.
Interference 105,871, Clark notice of service of supplemental evidence 6 dated Jul. 17, 2013.
Interference 105,871, Clark notice regarding exhibit 2136 dated Jul. 22, 2013.
Interference 105,871, Clark Notice Regarding Filing Priority Statement dated Jun. 5, 2012.
Interference 105,871, Clark Opposition 1 dated Aug. 17, 2012.
Interference 105,871, Clark opposition 10 dated Nov. 8, 2013.
Interference 105,871, Clark Opposition 19 dated Jul. 25, 2012.
Interference 105,871, Clark Opposition 6 dated Aug. 17, 2012.
Interference 105,871, Clark Opposition 8 dated Nov. 13, 2012.
Interference 105,871, Clark opposition dated Jul. 26, 2013.
Interference 105,871, Clark Priority Statement dated Jun. 5, 2012.
Interference 105,871, Clark Real Party-In-Interest dated Mar. 7, 2012.
Interference 105,871, Clark Reply 1 dated Oct. 11, 2012.
Interference 105,871, Clark reply 10 dated Nov. 22, 2013.
Interference 105,871, Clark Reply 2 dated Oct. 11, 2012.
Interference 105,871, Clark Reply 3 dated Oct. 11, 2012.
Interference 105,871, Clark Reply 6 dated Oct. 11, 2012.
Interference 105,871, Clark Reply 7 dated Nov. 19, 2012.
Interference 105,871, Clark reply 9 dated Sep. 6, 2013.
Interference 105,871, Clark Request for File Copies dated Mar. 7, 2012.
Interference 105,871, Clark request for oral argument 2 and list of issues dated Oct. 18, 2013.
Interference 105,871, Clark Request for Oral Arguments dated Oct. 23, 2012.
Interference 105,871, Clark response to Sommadossi reply 9 alleged material facts dated Sep. 17, 2013.
Interference 105,871, Clark Submission of Corrected Replies 1 and 6 dated Oct. 11, 2012.
Interference 105,871, Clark submission of DVD dated Dec. 23, 2013.
Interference 105,871, Clark submission of priority phase exhibits dated Nov. 7, 2013.
Interference 105,871, Clark submission of record 2 dated Dec. 4, 2013.
Interference 105,871, Clark Submission of Record dated Nov. 28, 2012.
Interference 105,871, Clark Submission of Sommadossi Declarations dated Jun. 28, 2012.
Interference 105,871, Clark Substantive Motion 1 dated Jun. 5, 2012.
Interference 105,871, Clark Substantive Motion 2 dated Jun. 5, 2012.
Interference 105,871, Clark Substantive Motion 3 dated Jun. 5, 2012.
Interference 105,871, Clark Substantive Motion 6 dated Jun. 5, 2012.
Interference 105,871, Clark substantive motion 9 dated Jun. 28, 2013.
Interference 105,871, Decision dated Jan. 29, 2014.
Interference 105,871, Decision on Motions dated Mar. 22, 2013.
Interference 105,871, Decision on Request for Rehearing dated Apr. 23, 2013.
Interference 105,871, email communication dated Jul. 22, 2013.
Interference 105,871, Judgement dated Jan. 29, 2014.
Interference 105,871, Notice Regarding Sommadossi Substantive Motion 5 dated Jun. 22, 2012.
Interference 105,871, Notice to Declare Interference dated Feb. 22, 2012.
Interference 105,871, Order Authorizing Miscellaneous Motion dated Jul. 16, 2012.
Interference 105,871, Order Authorizing Motions dated Apr. 24, 2012.
Interference 105,871, Order Authorizing Responsive Motion dated Jun. 18, 2012.
Interference 105,871, Order Cross Examination of Marquez dated Sep. 27, 2012.
Interference 105,871, Order Cross Examination of Witnesses dated Jul. 5, 2012.
Interference 105,871, Order Denying Requests for Oral Argument dated Nov. 16, 2012.
Interference 105,871, Order evidentiary matters dated Jul. 15, 2013.

(56) References Cited

OTHER PUBLICATIONS

Interference 105,871, Order miscellaneous dated Aug. 1, 2013.
Interference 105,871, Order miscellaneous dated Jul. 2, 2013.
Interference 105,871, Order miscellaneous dated Jul. 1, 2013.
Interference 105,871, Order miscellaneous dated Nov. 26, 2013.
Interference 105,871, Order miscellaneous dated Sep. 11, 2013.
Interference 105,871, Order miscellaneous dated Sep. 18, 2013.
Interference 105,871, Order regarding conference call of Apr. 2, 2013 dated Apr. 3, 2013.
Interference 105,871, Order regarding inappropriate communications dated Jan. 16, 2014.
Interference 105,871, Order Regarding Miscellaneous Motion and Notion Numbering dated Aug. 16, 2012.
Interference 105,871, Redeclaration dated Mar. 22, 2013.
Interference 105,871, Sommadossi Clean Claims dated Mar. 7, 2012.
Interference 105,871, Sommadossi Exhibit List dated Jun. 5, 2012.
Interference 105,871, Sommadossi File Copy Request dated Mar. 7, 2012.
Interference 105,871, Sommadossi filing of demonstrative exhibits dated Dec. 30, 2013.
Interference 105,871, Sommadossi Filing of the Record dated Nov. 28, 2012.
Interference 105,871, Sommadossi list of exhibits containing testimony of Edith Badel dated Jul. 18, 2013.
Interference 105,871, Sommadossi list of exhibits dated Nov. 8, 2013.
Interference 105,871, Sommadossi List of Issues dated Oct. 18, 2013.
Interference 105,871, Sommadossi miscellaneous motion 10 dated Oct. 18, 2013.
Interference 105,871, Sommadossi Miscellaneous Motion 19 dated Jul. 18, 2012.
Interference 105,871, Sommadossi Miscellaneous Motion 8 dated Oct. 23, 2012.
Interference 105,871, Sommadossi Motion 5 dated Jun. 5, 2012.
Interference 105,871, Sommadossi Motions List dated Apr. 11, 2012.
Interference 105,871, Sommadossi notice of judicial review dated Feb. 6, 2014.
Interference 105,871, Sommadossi Notice of Real Parties in Interest dated Mar. 7, 2012.
Interference 105,871, Sommadossi notice of related litigations dated Apr. 11, 2013.
Interference 105,871, Sommadossi Notice of Related Proceedings dated Mar. 7, 2012.
Interference 105,871, Sommadossi Notice of Service of Supplemental Evidence 4 dated Jun. 3, 2013.
Interference 105,871, Sommadossi Opposition 1 dated Aug. 17, 2012.
Interference 105,871, Sommadossi Opposition 2 dated Aug. 17, 2012.
Interference 105,871, Sommadossi Opposition 3 dated Aug. 17, 2012.
Interference 105,871, Sommadossi Opposition 6 dated Aug. 17, 2012.
Interference 105,871, Sommadossi Opposition 7 dated Nov. 13, 2012.
Interference 105,871, Sommadossi opposition 9 dated Jul. 26, 2013.
Interference 105,871, Sommadossi Priority Statement dated Jun. 5, 2012.
Interference 105,871, Sommadossi Reply 1 dated Oct. 11, 2012.
Interference 105,871, Sommadossi reply 10 dated Nov. 22, 2013.
Interference 105,871, Sommadossi Reply 19 dated Jul. 30, 2012.
Interference 105,871, Sommadossi Reply 6 dated Oct. 11, 2012.
Interference 105,871, Sommadossi Reply 8 dated Nov. 19, 2012.
Interference 105,871, Sommadossi reply 9 dated Sep. 6, 2013.
Interference 105,871, Sommadossi request for rehearing dated Apr. 5, 2013.
Interference 105,871, Sommadossi responses to Clark's MF of Clark reply 9 dated Sep. 17, 2013.
Interference 105,871, Sommadossi Responses to Material Facts of Clark Reply 3 dated Oct. 18, 2012.
Interference 105,871, Sommadossi Responses to Material Facts of Clark Corrected Reply 1 dated Oct. 18, 2012.
Interference 105,871, Sommadossi Responses to Material Facts of Clark Reply 2 dated Oct. 18, 2012.
Interference 105,871, Sommadossi Responses to Material Facts of Clark Corrected Reply 6 dated Oct. 18, 2012.
Interference 105,871, Sommadossi Submission of Clark Declarations dated Jun. 28, 2012.
Interference 105,871, Sommadossi submission of priority phase exhibits dated Nov. 8, 2013.
Interference 105,871, Sommadossi Substantive Motion 1 dated Jun. 5, 2012.
Interference 105,871, Sommadossi Substantive Motion 18 dated Jun. 22, 2012.
Interference 105,871, Sommadossi Substantive Motion 8 dated May 10, 2013.
Interference 105,871, Sommadossi supplemental notice of related proceedings dated Sep. 17, 2013.
Interference 105,871, Sommadossi supplemental notice of service of exhibits dated Jul. 26, 2013.
Interference 105,871, Sommodossi opposition 10 dated Nov. 8, 2013.
Interference 105,871, substitute Clark substantive motion 9 dated Jul. 22, 2013.
Interference 105,871, Substitute Sommadossi substantive motion 8, dated Jul. 18, 2013.
Interference 105,871, Transcript of Oral hearing held Jan. 7, 2014 dated Jan. 29, 2014.
Interference 105,981, Clark Reply 8 dated Jul. 9, 2014.
Interference 105,981, Clark Substantive Motion 7 dated Mar. 10, 2014.
Interference 105,981, Clark Substantive Motion 8 dated Mar. 10, 2014.
Interference 105,981, Clark Substantive Motion 9 dated Mar. 10, 2014.
Interference 105,981, Judgment dated Mar. 23, 2015.
Interference 105,981, Storer Opposition 7 dated May 23, 2014.
Interference 105,981, Storer Opposition 8 dated May 23, 2014.
Ishii et al., Hepatology 29: 1227-35 (1999).
Itoh, et al., "Divergent and Stereocontrolled Approach to the Synthesis of Uracil Nucleosides Branched at the Anomeric Position," J. Org. Chem., 60:656-662 (1995).
Jeong, Lak S. et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572 (1994).
Johnson, et al., "3'-C-Trifluoromethyl Ribonucleosides," Nucleoside Nucleosides, 14:185-194 (1995).
Jones, et al., "4'-Substituted Nucleosides. 5. Hydroxymehylation of Nucleoside 5'-Aldehydes," J. Org. Chem., 44:1309-1317 (1979).
Jones, et al., "Oxidation of Carbohydrates by the Sulfoxide-Carbodiimide and Related Methods," Meth. Carbohydrate Chem., 6:315-322 (1972).
Jordan et al., J. Infect. Dis. 182: 1214-17 (2000).
Julander et al., Antiviral Res. 86: 261-7 (2010).
Kakefuda, et al., "Nucleosides and Nucleotides. 120. Stereoselective Radical Deoxygenation of Tert-Alcohols in the Sugar Moiety of Nucleosides: Synthesis of 2',3'-Dideoxy-2'-C-Methyl- and -2'-C-Ethynyl-β-D-Threo-Pentofuranosyl Pyrimidines and Adenine as Potential Antiviral and Antitumor Agents," Tetrahedron, 49:8513-8528 (1993).
Kamaike, et al., "An Efficient Method for the Synthesis of [4-15N]Cytidine, 2'-Deoxy[4-15N]Cytidine, [6-15N]Adenosine, and 2'-Deoxy[6-15N]Adenosine Derivatives," Nucleosides Nucleotides, 15:749-769 (1996).
Kaneko, et al., "A Convenient Synthesis of Cytosine Nucleosides," Chem. Pharm. Bull., 20:1050-1053 (1972).

(56) References Cited

OTHER PUBLICATIONS

Kawana et al., "The Synthesis of C-Methyl Branched -Chain Deoxy Sugar Nucleosides by the Deoxygenative Methylation of O-Tosylated Adenosines with Grignard Reagents," Bull. Chem. Soc. Jpn., 61:2437-2442 (1988).
Kawana, et al., "The Deoxygenations of Tosylated Adenosine Derivatives with Grignard Reagents," Nucleic Acids Symp Ser., 17:37-40 (1986).
Kempe, et al., "Selective 2'-Benzoylation at the Cis 2',3'-Diols of Protected Ribonucleosides. New Solid Phase Synthesis of RNA and DNA-RNA Mixtures," Nucleic Acids Res., 10:6695-6714 (1982).
Kerr, et al., "N-(Dialkylamino)Methylene Derivatives of 2'-Deoxycytidine and Arabinocytidine:.Physicochemical Studies for Potential Prodrug Applications," J. Pharm. Sci., 83:582-586 (1994).
Khamnei, "Neighboring Group Catalysis in the Design of Nucleotide Prodrugs," J. Med. Chem., 39:4109-4115 (1996).
Kim et al., Biochem. Biophys. Res. Commun. 290: 105-12 (2002).
Kim, et al., "A Novel Nucleoside Prodrug-Activating Enzyme: Substrate Specificity of Biphenyl Hydrolase-like Protein," Mol. Pharm., 1:117-127 (2004).
King et al., "Inhibition of the replication of a hepatitis C virus-like RNA template by interferon and 3'-deoxycytidine," Antiviral Chemistry and Chemotherapy, 13:363-370 (2002).
Klumpp, et al., "The Novel Nucleoside Analog R1479 (4'-Azidocytidine) Is a Potent Inhibitor of NS5B-Dependent RNA Synthesis and Hepatitis C Virus Replication in Cell Culture," J. Biol. Chem., 281:3793-3799 (2006).
Kohn, et al., "A New Method for the Synthesis of Furanose Derivatives of Aldohexoses," J. Am. Chem. Soc., 87:5475-5480 (1965).
Kolykhalov et al., Science 277: 570-74 (1997).
Kotra, et al., "Structure-Activity Relationships of 2'-Deoxy-2',2'-Difluoro-L-Erythro-Pentofuranosyl Nucleosides," J. Med. Chem., 40:3635-3644 (1997).
Krieger et al., J. Virol. 75: 4614-24 (2001).
Kucera, et al., "Novel Membrane-Interactive Ether Lipid Analogs that Inhibit Infectious HIV-1 Production and Induce Defective Virus Formation," AIDS Res. Hum. Retro Viruses, 6:491-501 (1990).
Kuhn, et al., "Uber eine Molekulare Umlagerung von N-Glucosiden," Jahrg., 69:1745-1754 (1936).
Kuroboshi et al., Synlett 987-988 (1995).
Kurtzberg, et al., "Differential Toxicity of Carbovir and AZT to Human Bone Marrow Hematopoietic Progenitor Cells in Vitro," Exp. Hematol., 18:1094-1095 (1990).
Lai, et al., "Mutational Analysis of Bovine Viral Diarrhea Virus RNA-Dependant RNA Polymerase," J. Virol., 73:10129-101136 (1999).
Lal, G. Sankar, et al., Electrophilic NF Fluorinating Agents, Chem. Rev., vol. 96, pp. 1737-1755.
Lalezari, J., et al., Potent Antiviral Activity of the HCV Nucleoside Polymerase Inhibitor R7128 with PEG-IFN and Ribavirin: Interim Results of R7128 500mg BID for 28 Days, J. Hepatology, vol. 48, Supplement 2, p. S29 (2008).
Lalezari, J., et al., Potent Antiviral Activity of the HCV Nucleoside Polymerase Inhibitor, R7128, in Combination with PEG-IFN α-2a and Ribavirin, 43rd Annual Meeting of EASL, Milan, Italy, Apr. 23-27, 2008.
Lam et al., Antimicrob. Agents Chemother. 54: 3187-3196 (2010).
Lam et al., Antimicrob. Agents Chemother. 55: 2566-2575 (2011).
Landowski, "Nucleoside Ester Prodrug Substrate Specificity of Liver Carboxylesterase," J. Pharmacol. Exp. Ther., 316:572-580 (2006).
Lanford and Bigger, Virology 293: 1-9 (2002).
Lavaire, et al., "3'-Deoxy-3'-C-Trifluoromethyl Nucleosides: Synthesis and Antiviral Evaluation," Nucleosides Nucleotides, 17:2267-2280 (1998).
Lawitz et al., Abstract 102, Global Antiviral J. 5: 96.
Lawitz et al., Abstract 7, J. Hepatol. 56: S4 (2012).

Le Pogam, et al., "In Vitro Selected Conl Subgenomic Replicons Resistant to 2'-C-Methyl-Cytidine or to R1479 Show Lack of Cross Resistance," Virology, 351:349-359 (2006).
Le Pogam, et al., "Selection and Characterization of Replicon Variants Dually Resistant to Thumb- and Palm-Binding Nonnucleoside Polymerase Inhibitors of the Hepatitis C Virus," J. Virology, 80:6146-6154 (2006).
Leonard, et al., "5-Amino-5-deoxyribose Derivatives. Synthesis and Use in the Preparation of 'Reversed' Nucleosides (1a)," J. Heterocycl. Chem., 3:485-489 (1966).
Lerza, et al., "In Vitro Synergistic Inhibition of Human Bone Marrow Hemopoietic Progenitor Growth by a 3'-Azido-3' -Deoxy-Thymidine, 2',3'-Dideoxycytidine Combination," Exp. Hematol., 25:252-255 (1997).
Lesburg et al., Curr. Opin. Investig. Drugs 1: 289-96 (2000).
Lewis, et al., "Fialuridine and its Metabolites Inhibit DNA Polymerase y at Sites of Multiple Adjacent Analog Incorporating, Decrease mtDNA Abundance, and Cause Mitochondrial Structural Defects in Cultured Hepatoblasts," Proc. Natl. Acad. Sci. U.S.A., 93:3592-3597 (1996).
Lewis, et al., "Ultrastructural Changes Associated with Reduced Mitochondrial DNA and Impaired Mitochondrial Function in the Presence of 2',3'-Dideoxycytidine," Antimicrob. Agents Chemother., 36:2061-2065 (1992).
Lewis, et al., "Zidovudine Induces Molecular, Biochemical, and Ultrastructural Changes in Rat Skeletal Muscle Mitochondria," J. Clin. Invest., 89:1354-1360 (1992).
Leyssen, et al., "Perspectives for the Treatment of Infections with Flaviviridae," Clin. Microbiol. Rev., 13:67-82 (2000).
Li, et al., "2'-C-Branched Ribonucleosides. 2. Synthesis of 2'-C-β-Trifluormethyl Pyrimidine Ribonucleosides," Org. Lett., 3:1025-1028 (2001).
Limbach, Patrick A., et al., Summary: The Modified Nucleosides of RNA, Nucleic Acids Research, vol. 22, No. 12, pp. 2183-2196 (1994).
Lin, et al., "Synthesis of Several Pyrimidine L-Nucleoside Analogues as Potential Antiviral Agents," Tetrahedron Lett., 51:1055-1068 (1995).
Lindenbach, B.D. and Rice, C.M., Flaviviridae: The Viruses and Their Replication (Chapter 32) in Knipe, D.M. et al., eds., Fields Virology, 4th ed. Philadelphia, Lippincott Williams & Wilkins (2001).
Lohmann et al. 1999, J. Biol. Chem. 274: 10807-15.
Lohmann et al., J. Virol. 71: 8416-28 (1997).
Lohmann et al., J. Virol. 75: 1437-49 (2001).
Lohmann, et al., "Biochemical and Kinetic Analyses of NS5B RNA-Dependent RNA Polymerase of the Hepatitis C Virus," Virology, 249:108-118 (1998).
Lohmann, V et al., Replication of Subgenomic Hepatitis C Virus RNAs in a Hepatoma Cell Line, Science, vol. 285, pp. 110-113 (1999).
Lopez-Herrera, et al., "A New Synthesis of 2-C-Methyl-D-Ribono-1,4-Lactone and the C-9/C-13 Fragment of Methynolide," J. Carbohydrate Chem., 13:767-775 (1994).
Luh, et al., "A Convenient Method for the Selective Esterification of Amino-Alcohols," Synth. Commun., 8:327-333 (1978).
Maga, et al., "Lack of Stereospecificity of Suid Pseudorabies Virus Thymidine Kinase," Biochem. J., 294:381-385 (1993).
Mahmoudian, et al., "A Versatile Procedure for the Generation of Nucleoside 5'-Carboxylic Acids Using Nucleoside Oxidase," Tetrahedron, 54:8171-8182 (1998).
Mansour, et al., "Editorial," Antiinfec Agents Med. Chem., 6:1 (2007).
Markland et al., Antimicrob. Agents Chemother. 44: 859-66 (2000).
Markland, et al., "Broad-Spectrum Antiviral Activity of the IMP Dehydrogenase Inhibitor VX-497: A Comparison with Ribavirin and Demonstration of Antiviral Additivity with Alpha Interferon," Antimicrob. Agents Chemother., 44:859-866 (2000).
Marshall, Science 290: 1870-71 (2000).
Martin, et al., "Intramolecular Hydrogen Bonding in Primary Hydroxyl of Thymine 1-(1-Deoxy-β-D-Piscofuranosyl)Nucleoside," Tetrahedron, 50:6689-6694 (1994).

(56) References Cited

OTHER PUBLICATIONS

Martin, et al., "Synthesis and Antiviral Activity of Monofluoro and Difluoro Analogues of Pyrimidine Deoxyribonucleosides against Human Immnodeficiency Virus (HIV-1)," J. Med. Chem., 33:2137-2145 (1990).
Matsuda et al., Chem. Pharm. Bull. 36(3): 945-953 and 3967-3970 (1988).
Matsuda, et al., "Alkyl Addition Reaction of Pyrimidine 2'-Keta-onucleosides: Synthesis of 2'-Branched-Chain Sugar Pyrimidine Nucleosides (Nucleosides and Nucleotides. LXXXI)," Chem. Pharm. Bull., 36:945-53 (1988).
Matsuda, et al., "Nucleosides and Nucleotides 104. Radical and Palladium-Catalyzed Deoxygenation of the Allylic Alcohol Systems in the Sugar Moiety of Pyrimidine Nucleosides," Nucleosides Nucleotides, 11:197-226 (1992).
Matsuda, et al., "Nucleosides and Nucleotides 94. Radical Deoxygenation of Tert-Alcohols in 1-(2-C-Alkylpentafuranosyl)Pyrimidines: Synthesis of (2'S)-2-Deoxy-2'-C-Methylcytidine, and Antileukemic Nucleoside," J. Med. Chem., 34:234-239 (1991).
Matsuda, et al., "Radical Deoxygenation of Tert-Alcohols in 2'-Branched-Chain Sugar Pyrimidine Nucleosides: Synthesis and Antileukemic Activity of 2'-Deoxy-2'(S)-Methylcytidine," Chem. Pharm. Bull., 35: 3967-3970 (1987).
McCormick, J., et al., "Structure and Total Synthesis of HF-7, a Neuroactive Glyconucleoside Disulfate from the Funnel-Web Spider Hololena Curta," J. Am. Chem. Soc., 121:5661-5665 (1999).
Mcfarlin, et al., "The Reaction of Lithium Aluminum Hydride with Alcohols. Lithium Tri-t-Butoxy-Aluminohydride as a New Selective Reducing Agent," J. Am. Chem. Soc., 80:5372-5376 (1958).
McGuigan et al, Antiviral Chem. & Chemother. 12: 293-300 (2001).
McGuigan et al., Antiviral Chem. Chemother. 5: 271-277 (1994).
McKenzie, et al., "Hepatic Failure and Lactic Acidosis Due to Fialuridine (FIAU), an Investigational Nucleoside Analogue for Chronic Hepatitis B," N. Engl. J. Med., 333:1099-1105 (1995).
McKenzie, Robin, M.D., et al., Hepatic Failure and Lactic Acidosis Due to Fialuridine (FIAU), an Investigational Nucleoside Analogue for Chronic Hepatitis B, the New England Journal of Medicine, vol. 333, No. 17, pp. 1099-1105 (1995).
McManus, Appl. Environ. Microbiol. 31: 35-38 (1976).
Medina, et al., "Comparison of Mitochondrial Morphology, Mitochondrial DNA Content, and Cell Viability in Cultured Cell Treated with Three Anti-Human Immunodeficiency Vims Dideoxynucleosides," Antimicrob Agents Chemother., 38:1824-8 (1994).
Meier, et al., "Cyclic Saligenyl Phosphotriesters of 2',3'-Dideoxy-2',3'-Didehydrothymidine (d4T)—a New Pro-Nucleic Approach," Bioorg. Med. Chem. Lett., 7:99-104 (1997).
Meyer, et al., "2'-O-Acyl-6-Thioinosine Cyclic 3',5'-Phosphates as Prodrugs of Thioinosinic Acid," J. Med. Chem., 22:811-815 (1979).
Mikhailov, et al., "Hydrolysis of 2'- and 3'-C-Methyluridine 2',3'-Cyclic Monophosphates and Interconversion and Dephosphorylation of the Resulting 2'- and 3'-Monophosphates: Comparison with the Reactions of Uridine Monophosphates," J. Org. Chem., 57:4122-4126 (1992).
Mikhailov, et al., "Substrate Properties of C'-Methylnucleoside and C'-Methyl-2'-Deoxynucleoside 5'-Triphosphates in RNA and DNA Synthesis Reactions Catalyzed by RNA and DNA polymerases," Nucleosides Nucleotides, 10:339-343 (1991).
Mikhailov, et al., "Synthesis and Properties of 3'-C-Methylnucleosides and Their Phosphoric Esters," Carbohydrate Res., 124:75-96 (1983).
Miles, et al., "Circular Dichroism of Nucleoside Derivatives. IX. Vicinal Effects on the Circular Dichroism of Pyrimidine Nucleosides," J. Am. Chem. Soc., 92:3872-3881 (1970).
Milne, H. Bayard and Peng, Chi-Hsieh, The Use of Benzylsulfonyl Chloride in Peptide Syntheses, J. Am. Chem. Soc., vol. 79, pp. 639-644 (1956).
Moiseyev, et al., "Determination of the Nucleotide Conformation in the Productive Enzyme-Substrate Complexes of RNA-Depolymerases," FEBS Lett., 404:169-172 (1997).
Moore, et al., "Synthesis of Nucleotide Analogues that Potently and Selectively Inhibit Human DNA Primase," Biochemistry, 41:14066-14075 (2002).
Moradpour et al., J. Biol. Chem. 277: 593-601 (2002).
Mottola et al., Virology 293:31-43 (2002).
Murai, et al., "A Synthesis and an X-Ray Analysis of 2'-C-, 3'-C- and 5'-C-Methylsangivamycins," Heterocycles, 33:391-404 (1992).
Murakami et al., J. Biol. Chem. 285: 34337-34347 (2010).
Neidlein, et al., "Mild Preparation of 1-Benzyloxyiminoalkylphosphonic Dichlorides: Application to the Synthesis of Cyclic Phosphonic Diesters and Cyclic Monoester Amides," Heterocycles, 35:1185-1203 (1993).
Ness and Fletcher, J. Org. Chem. 22: 1470-1473 (1957).
News & Analysis, Nature Reviews 10: 891 (2011).
Nishiguchi, et al., "Methods to Detect Substitutions in the Interferon-Sensitivity-Determining Region of Hepatitis C Virus lb for Prediction of Response to Interferon Therapy," Hepatology, 33:241-247 (2001).
Nishimura, et al., "Studies on Synthetic Nucleosides. Trimethylsilyl Derivatives of Pyrimidines and Purines," Chem. Pharm. Bul., 12:352-356 (1964).
Non-Final Office Action dated Jan. 5, 2011 from U.S. Appl. No. 12/504,601.
Notice of Allowance dated Dec. 27, 2005 from U.S. Appl. No. 10/602,693.
Notice of Allowance dated Dec. 27, 2005 from U.S. Appl. No. 10/602,694.
Notice of Allowance dated Dec. 28, 2005 from U.S. Appl. No. 10/602,692.
Notice of Allowance dated Feb. 19, 2004 from U.S. Appl. No. 09/864,078.
Notice of Allowance dated Jan. 8, 2008 from U.S. Appl. No. 11/005,441.
Notice of Allowance dated Jun. 15, 2009 from U.S. Appl. No. 10/602,691.
Notice of Allowance dated Jun. 21, 2012 from U.S. Appl. No. 12/504,601.
Notice of Allowance dated Jun. 22, 2007 from U.S. Appl. No. 11/005,441.
Notice of Allowance dated Jun. 23, 2004 from U.S. Appl. No. 09/863,816.
Notice of Allowance dated Mar. 9, 2006 from U.S. Appl. No. 10/602,136.
Notice of Allowance dated May 17, 2005 from U.S. Appl. No. 10/602,135.
Notice of Allowance dated Oct. 13, 2005 from U.S. Appl. No. 10/602,976.
Novak, "Chiroptical Properties of 2-Methyl-1,4-Lactones; Revised Absolute Configuration of 2-Deoxy-2-C-Methyl-Elythro-D-Pentono-1,4-Lactones," Collect. Czech. Chem. Commun., 39:869-882 (1974).
Novak, et al., "Nucleic Acid Components and Their Analogues. CXX. 2-C-Methyl-D-Ribose and Its Derivatives," Collect. Czech. Chem. Commun., 34:857-866 (1969).
Nutt, et al., "Branched-Chain Sugar Nucleosides. III. 3'-C-Methyladenine," J. Org. Chem., 33:1789-1795 (1968).
O'Boyle, "Development of a cell-based high-throughput specificity screen using a hepatitis C virus-bovine viral diarrhea virus dual replicon assay," Antimicrob. Agents Chemother., 49(4):1346-1353 (2005).
Office Action dated Jan. 28, 2008 from U.S. Appl. No. 10/608,907.
Office Action dated May 31, 2007 from U.S. Appl. No. 10/608,907.
Office Action dated Aug. 15, 2006 from U.S. Appl. No. 10/608,907.
Office Action dated Apr. 5, 2005 from U.S. Appl. No. 10/602,135.
Office Action dated Apr. 5, 2005 from U.S. Appl. No. 10/602,692.
Office Action dated Apr. 6, 2005 from U.S. Appl. No. 10/602,693.
Office Action dated Apr. 6, 2005 from U.S. Appl. No. 10/602,694.
Office Action dated Aug. 2, 2006 from U.S. Appl. No. 10/609,298.
Office Action dated Aug. 21, 2006 from U.S. Appl. No. 11/005,441.
Office Action dated Aug. 27, 2003 from U.S. Appl. No. 09/864,078.
Office Action dated Aug. 7, 2006 from U.S. Appl. No. 11/005,442.
Office Action dated Dec. 10, 2008 from U.S. Appl. No. 10/602,142.
Office Action dated Dec. 29, 2006 from U.S. Appl. No. 10/602,691.
Office Action dated Dec. 5, 2006 from U.S. Appl. No. 11/005,440.

(56) References Cited

OTHER PUBLICATIONS

Office Action dated Feb. 26, 2008 from U.S. Appl. No. 10/602,142.
Office Action dated Feb. 26, 2008 from U.S. Appl. No. 10/602,691.
Office Action dated Jul. 10, 2008 from U.S. Appl. No. 10/609,298.
Office Action dated Jul. 28, 2006 from U.S. Appl. No. 10/602,142.
Office Action dated Jun. 13, 2007 from U.S. Appl. No. 11/005,440.
Office Action dated Mar. 29, 2007 from U.S. Appl. No. 10/602,142.
Office Action dated May 16, 2007 from U.S. Appl. No. 11/005,442.
Office Action dated May 19, 2005 from U.S. Appl. No. 10/602,976.
Office Action dated May 30, 2006 from U.S. Appl. No. 10/602,691.
Office Action dated Nov. 15, 2005 from U.S. Appl. No. 10/602,142.
Office Action dated Nov. 26, 2008 from U.S. Appl. No. 10/608,907.
Office Action dated Nov. 28, 2007 from U.S. Appl. No. 11/005,442.
Office Action dated Nov. 7, 2005 from U.S. Appl. No. 10/602,691.
Office Action dated Oct. 1, 2003 from U.S. Appl. No. 09/863,816.
Office Action dated Oct. 16, 2007 from U.S. Appl. No. 11/005,440.
Office Action dated Oct. 5, 2005 from U.S. Appl. No. 11/005,440.
Office Action dated Sep. 10, 2004 from U.S. Appl. No. 10/602,976.
Office Action dated Sep. 20, 2007 from U.S. Appl. No. 10/602,142.
Oh et al., J. Virol. 73: 7694-702 (1999).
Oivanen, et al., "Additional Evidence for the Exceptional Mechanism of the Acid-Catalyzed Hydrolysis of 4-Oxopyrimidine Nucleosides: Hydrolysis of 1-(1-Alkoxyalkyl)uracils, Seconucleosides, 3'-C-Alkyl nucleosides and Nucleoside 3',5'-Cyclic Monophosphates," J. Chem. Soc. Perkin Trans. 2, 309-314 (1994).
Ong, et al., "Synthesis of 3'-C-Methyladenosine and 3'-C-Methyluridine Diphosphates and Their Interaction with the Ribonucleoside Diphosphate Reductase from Corynebacterium Nephridii," Biochemistry, 31:11210-11215 (1992).
Oxtoby, David W., et al., Principles of Modern Chemistry, Fourth Edition, pp. A.41-A.49 (1999).
Pagliaro, et al., "Epatologia: Ieri, Oggi E (Forse) Domani," Recenti Progressi in Medicina, 97:741-750 (2006).
Pankiewicz, "Fluorinated nucleosides," Carbohydr. Res., 327(1-2):87-105 (2000).
Pan-Zhou, et al., "Differential Effects of Antiretroviral Nucleoside Analogs on Mitochondrial Function in HepG2 Cells," Antimicrob. Agents Chemother., 44:496-503 (2000).
Piantadosi, et al., "Synthesis and Evaluation of Novel Ether Lipid Nucleoside Conjugates for Anti-HIV-1 Activity," J. Med. Chem., 34:1408-1414 (1991).
Pierra, et al., "NM 283, an Efficient Prodrug of the Potent Anti-HCV Agent 2'-C-Methylcytidine," Nucleosides, Nucleotides Nucleic Acids, 24:767-770 (2005).
Pierra, et al., "Synthesis and Pharmacokinetics of Valopicitabine (NM283), an Efficient Prodrug of the Potent Anti-HCV Agent 2'-C-Methylcytidine," J. Med. Chem., 49:6614-6620 (2006).
Pierra., et al., "Comparative Studies of Selected Potential Prodrugs of B-L-dC, a Potent and Selective Anti-HBV Agent," Antiviral. Res., 50:A79 (2001).
Pietschmann et al., J. Virol. 75: 1252-64 (2001).
Prusoff, Cancer Res. 23: 1246-59 (1963).
Randall and Rice, Curr. Opin. Infect. Dis. 14: 743-47 (2001).
Reist, et al., "Potential Anticancer Agents. LXXVII. Synthesis of Nucleosides of Purine-6-Thiol(6-Mercaptopurine) Containing 'Fraudulent' Sugars," J. Org. Chem., 27:3279-3283 (1962).
Richman, et al., "The Toxicity of Azidothymidine (AZT) in the Treatment of Patients with AIDS and AIDS-Related Complex," N. Engl. J. Med., 317:192-197 (1987).
Robins, et al., "Purine Nucleosides. XXIX. The Synthesis of 2'-Deoxy-L-Adenosine and 2'-Deoxy-L-Guanosine and Their α Anomers," J. Org. Chem., 35:636-639 (1970).
Rong, et al., "The Synthesis and Conformation of 2'- and 3'-Hypermodified Tricyclic Nucleosides and Their Use in the Synthesis of Novel 2'- or 3'-Isomeric 4(7)-Substituted Isoxazolidine-Nucleosides," Tetrahedron, 50:4921-4936. (1994).
Roque-Afonso, et al., "Performance of TRUGENE™ Hepatitis C Virus 5' Noncoding Genotyping Kit, a New CLIP™ Sequencing-Based Assay for Hepatitis C Virus Genotype Determination," J. Viral Hepatitis., 9:385-389 (2002).

Rosenberg, J. Mol. Biol. 313: 451-64 (2001).
Rosenthal, et al., "Branched-Chain Sugar Nucleosides. Synthesis of 3'-C-Ethyl (and 3'-C-Butyl)Uridine," Carbohydrate Res., 79:235-242 (1980).
Sakthivel, et al., "Direct SNAr Amination of Fluorinated Imidazo[4,5-c]Pyridine Nucleosides: Efficient Syntheses of 3-Fluoro-3-Deazaadenosine Analogs," Tetrahedron Lett., 46:3883-3887 (2005).
Sakthivel, et al., "Electrophilic Fluorination of 5-(Cyanomethyl)Imidazole-4-Carboxylate Nucleosides: Facile Entry to 3-Fluoro-3- Deazaguanosine Analogues," Synlett, 1586-1590 (2005).
Saladino, et al., "A New and Efficient Synthesis of Cytidine and Adenosine Derivatives by Dimethyldioxirane Oxidation of Thiopyrimidine and Thiopurine Nucleosides," J. Chem. Soc., Perkin Trans. I, 21:3053-3054 (1994).
Samano, et al., "Nucleic Acid Related Compounds. 77. 2',3'-Didehydro-2',3'-Dideoxy-2'(and 3')-Methylnucleo sides via [3,3]-Sigmatropic Rearrangements of 2'(and 3')-Methylene-3'(and 2')-O-Thiocarbonyl Derivatives and Radical Reduction of a 2'-Chloro-3'-Methylene Analogue," Can. J. Chem., 71:186-191 (1993).
Samano, et al., "Synthesis and Radical-Induced Ring-Opening Reactions of 2'-Deoxyadenosine-2'-Spirocyclopropane and its Uridine Analogue. Mechanistic Probes for Ribonucleotide Reductases," J. Am. Chem. Soc. 114:4007-4008 (1992).
Sandhu, et al., "Evaluation of Microdosing Strategies for Studies in Preclinical Drug Development: Demonstration of Linear Pharmacokinetics in Dogs of a Nucleoside Analog over a 50-Fold Dose Range," Drug Metab. Dispos., 32:1254-1259 (2004).
Sato, et al., "C-Nucleoside Synthesis. 10. Synthesis of 2'-Methylated Pyrimidine C-Nucleosides," Tetrahedron Lett., 21:1971-1974 (1980).
Sato, et al., "C-Nucleoside Synthesis. 19. Stereocontrolled General Synthesis of Pyrimidine C-Nucleosides Having Branched-Chain Sugar Moieties," Bull. Chem. Soc. Jpn., 56:2680-99 (1983).
Savochkina, et al., "Substrate Properties of C—Methylnucleoside Triphosphates in RNA Syntheses Catalyzed by *Escherichia coli* RNA—Polymerase," Mol. Biol., 23:1700-1710 (1989).
Scheibler, "Ueber das Saccharin and die Saccharinsaure," Chem. Ber., 13:2212-2217 (1880).
Schiff, "Emerging Strategies for Pegylated Interferon Combination Therapy," Nat. re Clin. Pract. Gastoenterol. Hepatol., 4:S17-S21 (2007).
Schmit, et al., "The Effects of 2'- and 3'-Alkyl Substituents on Oligonucleotide Hybridization and Stability," Bioorg. Med. Chem. Lett., 4:1969-1974 (1994).
Schmit, et al., "Synthesis of 2'-Deoxy-2'-Alpha-Monofluoromethyl and Trifluoromethylnucleosides," Synlett, 4:241-242 (1994).
Schmit, Synlett 238-240 (1994).
Serafinowski, et al., "New Method for the Preparation of Some 2'- and 3'-Trifluoromethy 1-2',3'-Dideoxyuridine Derivatives," Tetrahedron, 56:333-339 (1999).
Shalaby, et al., "Conformations and Structure Studies of Sugar Lactones in the Solid State. Part II. The Molecular Structure of α-D-Glucosaccharino-γ-Lactone: 2-C-Mehtyl-D-Ribo-Pentono-1,4-Lactone," Carbohydrate Res., 264:191-198 (1994).
Sharma, et al., "Synthesis of 3'-Trifluoromethyl Nucleosides as Potential Antiviral Agents," Nucleosides, Nucleotides Nucleic Acids, 19:757-774 (2000).
Shi and Lai, Cell. Mol. Life Sci. 58: 1276-95 (2001).
Shi, et al., "Synthesis and in vitro Anti-HCV Activity of β-d- and 1-2'-Deoxy-2'-Fluororibonucleosides," Nucleosides, Nucleotides Nucleic Acids, 23:875-879 (2005).
Shim, "Recent Patents on Nucleoside and Nucleotide Inhibitors for HCV," Recent Pat. Antiinfect Drug Discov., 1:323-331 (2006).
Shim, J. et al., Canonical 3'-deoxyribonucleotides as a chain terminator for HCV NS5B RNA-dependent RNA polymerase, Antiviral Research, vol. 58, pp. 243-251 (2003).
Shimakami et al., Proc. Nat'l. Acad. Sci U.S.A. 109:941-6 (2012).
Singh, Rajendra P. and Shreeve, Jean'ne M., Recent Advances in Nucleophilic Fluorination Reactions of Organic Compounds Using Deoxofluor and DAST, Synthesis, No. 17, pp. 2561-2678 (2002).

(56) References Cited

OTHER PUBLICATIONS

Sinko, et al., "Carrier-Mediated Intestinal Absorption of Valacyclovir, the L-Valyl Ester Prodrug of Acyclovir," Biopharm. Dmg Dispos., 19:209-217 (1998).
Sinkula, et al., "Rationale for Design of Biologically Reversible Drug Derivatives: Prodrugs," J. Pharm. Sci., 64:181-210 (1975).
Smith, et al., "Synthesis of New 2'-β-C-Methyl Related Triciribine Analogues as Anti-HCV Agents," Bioorg. Med. Chem. Lett., 14:3517-3520 (2004).
Sofia et al., J. Med. Chem. 53: 7202-7218 (2010).
Sofia et al., Abstracts of Papers, 238th ACS National Meeting, Washington, DC, United States, Aug. 16-20, 2009, MEDI-101.
Sofia, Michael J., et al., Nucleoside, Nucleotide, and Non-Nucleoside Inhibitors of Hepatitis C Virus NS5B RNA-Dependent RNA-Polymerase, J. Med. Chem., vol. 55, pp. 2481-2531 (2012).
Sommadossi, et al., "Comparison of Cytotxicity of the (-)- and (+)-Enantiomer of 2',3'-Dideoxy-3'-Thiacytidine in Normal Human Bone Marrow Progenitor Cells," Biochem. Pharmacol., 44-1921-1925 (1992).
Sommadossi, et al., "Toxicity of 3'-Azido-3'-Deoxythymidine and 9-(1,3-Dihydroxy-2-Propoxymethyl)Guanine for Normal Human Hematopoietic Progenitor Cells in Vitro," Antimicrob. Agents Chemother., 31:452-454 (1987).
Song, et al., "Amino Acid Ester Prodrugs of the Anticancer Agent Gemcitabine: Synthesis, Bioconversion, Metabolic Bioevasion, and hPEPT1-Medicated Transport," Mol. Pharm., 2:157-167 (2005).
Sorbera, et al., "Valopicitabine: Anti-Hepatitis C Virus Drug RNA—Directed RNA Polymerase (NS5B) Inhibitor," Drugs of the Future, 31:320-324 (2006).
Sowa et al., Bulletin of the Chemical Society of Japan 48(7): 2084-2090 (1975).
Sowden, "The Saccharinic Acids," Adv. Carbohydrate Chem., 12:43-46 (1957).
Spardari, et al., "L-Thymidine Is Phosphorylated by Herpes Simplex Virus Type 1 Thymidine Kinase and Inhibits Viral Growth," J. Med. Chem., 35:4214-4220 (1992).
Standring, et al., "Antiviral β-L-Nucleosides Specific for Hepatitis B Virus Infection," Antiviral Chem. Chemother., 12 :119-129 (2001).
Starrett, et al., "Synthesis, Oral Bioavailability Determination, and in Vitro Evaluation of Prodrugs of the Antiviral Agents 9-(2-(Phosphonomethoxy)Ethyl)Adenine (PMEA)," J. Med. Chem., 37:1857-1864 (1994).
Stein et al., "Phosphorylation of Nucleoside Analog Antiretrovirals: A Review for Clinicians," Phamacotherapy, 21:11-34 (2001).
Stuvyer, L.J. et al., Inhibition of Hepatitis C Replicon RNA Synthesis by β-D-2'-Deoxy-2'-fluoro-2'-C-methylcytidine: A Specific Inhibitor of Hepatitis C Virus Replication, Antimicrobial Agents & Chemotherapy, vol. 17, pp. 79-87 (2006).
Stuyver et al., "Hepatitis C therapeutics: current status and emerging strategies," Nat. Rev. Drug Dicov., 1(11):867-881 (2002).
Stuyver, et al., "Ribonucleoside Analogue that Block Replication of Bovine Viral Diarrhea and Hepatitis C Viruses in Culture," Antimicrob. Agents Chemother., 47:244-254 (2003).
Stuyver, L.J., et al., Inhibition of the Subgenomic Hepatitis C Virus Replicon in Huh-7 Cells by 2'-deoxy-2'-fluorocytidine, Antimicrobial Agents and Chemotherapy, vol. 48, No. 2, pp. 651-654 (2004).
Substitute Declaration of Christoph Seeger, Ph.D.
Substitute Declaration of Victor E. Marquez, Ph.D.
Sundberg, et al., Advanced Organic Chemistry, Part B, pp. 232 and 236 (1990).
Taguchi et al., J. of the American Chemical Society 96: 3010-3011 (1974).
Takenuki, et al., "Nucleosides and Nucleotides. XLIII. On the Stereoselectivity of Alkyl Addition Reaction of Pyrimidine 2'-Ketonucleosides," Chem. Pharm. Bull., 38:2947-2952 (1990).
Taktakishvili and Nair, Tetrahedron Letters 41: 7173-7176 (2000).
Tan et al., "Hepatitis C therapeutics: current status and emerging strategies," Nat. Rev. Drug Discov., 1(11):867-881 (2002).
Tang, et al., "2'-C-Branched Ribonucleosides: Synthesis of the Phophoramidite Derivatives of 2'-C-B-Methylcytidine and Their Incorporation into Oligonucleotides," J. Org. Chem., 64:747-754 (1999).
The Journal of the Americal Chemical Society, Table of Contents, vol. 79, No. 3 (1957).
The Merck Index, 12th edition, p. 275 (1996).
The Merck Index, 2001, 13th ed., 4401.
Tisdale et al., Antivir. Chem. Chemother., 4(5): 281-7 (1993).
Tong et al., "Nucleosides of thioguanine and other 2-amino-6-substituted purines from 2-acetamido-5-chloropurine," J. Org. Chem., 32:859-862 (1967).
Transcript of Deposition of Christoph Seeger, Ph.D., taken Jul. 25, 2012.
Transcript of Deposition of Christoph Seeger, Ph.D., taken Sep. 28, 2012.
Transcript of Deposition of Victor E. Marquez, Ph.D., taken Jul. 27, 2012.
Transcript of Deposition of Victor E. Marquez, Ph.D., taken Sep. 26, 2012.
Tritsch, et al., "3'-β-Ethynyl and 2'-Deoxy-3'-β-Ethynyl Adenosines: First 3'-β-Branched Adenosine Substrates of Adenosine Deaminase," Bioorg. Med. Chem. Lett., 10:139-141 (2000).
Tronchet, et al., "72. Synthese et Desamination Enzymatique Des C-Hydroxymethyl-3'-et C-Methyl-3'-β-D-Xylofurannosyl-9-Adenines," Hely. Chim. Acta, 62:689-695 (1979).
Trost, Barry M. and Kallander, Lara S., A Versatile Enantioselective Strategy Toward L-C-Nucleosides: A Total Synthesis of L-Showdomycin, J. Org. Chem., vol. 64, No. 15, pp. 5427-5435 (1999).
Trost, Barry M., et al., Asymmetric Synthesis of Oxygen Heterocycles via Pd-Catalyzed Dynamic Kinetic Asymmetric Transformations: Application to Nucleosides, Chem Eur. J., vol. 9, pp. 4442-4451 (2003).
Tunitskaya, et al., "Substrate Properties of C'-Methyl UTP Derivatives in T7 RNA Polymerase Reactions. Evidence for N-Type NTP Conformation," FEBS Lett., 400:263-266 (1997).
Tyrsted, et al., "Inhibition of the Synthesis of 5-Phosphoribosyl-l-Pyrophosphate by 3'-Deoxyadenosine and Structurally Related Nucleoside Analogs," Biochem. Biophys. Acta., 155:619-622 (1968).
U.S. Appl. No. 11/854,218 Preliminary Amendment dated Sep. 12, 2007.
U.S. Appl. No. 10/608,907 Amendment filed Jul. 24, 2008.
U.S. Appl. No. 10/608,907 Amendment filed Aug. 20, 2007.
U.S. Appl. No. 10/608,907 Amendment filed Feb. 15, 2007.
U.S. Appl. No. 10/608,907 Amendment filed Jan. 20, 2009.
U.S. Appl. No. 10/608,907 Amendment filed May 25, 2006.
U.S. Appl. No. 10/608,907 Declaration and Power of Attorney filed Jan. 12, 2004.
U.S. Appl. No. 10/608,907 Notice of Allowance dated Apr. 7, 2009.
U.S. Appl. No. 10/608,907 Supplemental Amendment filed Oct. 30, 2007.
U.S. Appl. No. 11/005,444 Amendment dated Apr. 4, 2008.
U.S. Appl. No. 11/005,444 Amendment dated Apr. 6, 2009.
U.S. Appl. No. 11/005,446 Amendment dated May 7, 2007.
U.S. Appl. No. 11/005,469 Amendment dated Dec. 14, 2007.
U.S. Appl. No. 11/005,469 Amendment dated Apr. 5, 2007.
U.S. Appl. No. 11/854,218 Amendment dated Jun. 20, 2011.
U.S. Appl. No. 11/854,218 Amendment dated Oct. 11, 2010.
U.S. Appl. No. 11/854,218 Office Action dated Dec. 23, 2010.
U.S. Appl. No. 11/854,218 Office Action dated Jul. 22, 2010.
U.S. Appl. No. 12/131,868 Amendment dated Jun. 21, 2012.
U.S. Appl. No. 12/131,868 Amendment dated May 27, 2011.
U.S. Appl. No. 12/131,868 Amendment dated Sep. 20, 2011.
U.S. Appl. No. 12/131,868 Declaration and Power of Attorney filed Jun. 2, 2008.
U.S. Appl. No. 12/131,868, filed Jun. 2, 2008.
U.S. Appl. No. 12/131,868 Office Action dated Aug. 16, 2011.
U.S. Appl. No. 12/131,868 Office Action dated Mar. 3, 2011.
U.S. Appl. No. 12/131,868 Preliminary Amendment filed Jun. 2, 2008.
U.S. Appl. No. 12/131,868 Response to Notice to File Corrected Application Papers dated Sep. 17, 2008.

(56) References Cited

OTHER PUBLICATIONS

U.S. Appl. No. 12/131,868 Response to Restriction Requirement dated Dec. 14, 2010.
U.S. Appl. No. 12/131,868 Substitute Specification (clean version).
U.S. Appl. No. 12/131,868 Substitute Specification (marked up version).
U.S. Appl. No. 12/150,327 Amendment dated Nov. 16, 2010.
U.S. Appl. No. 12/878,262 Office Action dated Jun. 8, 2011.
U.S. Appl. No. 12/878,262 Preliminary Amendment dated Sep. 9, 2010.
U.S. Appl. No. 60/392,350 Corrected Filing Receipt dated Jan. 17, 2008.
U.S. Appl. No. 60/392,350 Provisional Application filed Jun. 28, 2002.
U.S. Appl. No. 60/474,368 Provisional Appln. Cover Sheet dated May 30, 2003.
U.S. Appl. No. 60/474,368, Petition to Correct Inventorship dated Jul. 11, 2005.
U.S. Pat. No. 7,429,572 Restriction Requirement dated Sep. 5, 2006.
Usui, et al., "Synthesis of 2'-Deoxy-8,2'-Ethanoadenosine and 3'-Deoxy-8,3'-Ethanoadenosine (Nucleotides & Nucleosides. LXIV)," Chem. Pharm. Bull., 34:15-23 (1986).
Van Boom et al., Tetrahedron Letters 27: 1211-1214 (1986).
Vassilev, et al., "Bovine Viral Diarrhea Virus Induced Apoptosis Correlates with Increased Intracellular Viral RNA Accumulation," Virus Res., 69:95-107 (2000).
Velazquez, et al., "Synthesis of [1-[3',5'-Bis-O-(Tert-Butyldimethylsilyl)-β-D-Arabino- and β-D-Ribofuransoyl]Cytosine]-2'—Spiro-5"-(4"-Amino-1",2"-Oxathiole-2",2"-Dioxide). Analogues of the Highly Specific Anti-HIV-1 Agent TSAO-T," Tetrahedron, 50:11013-11022 (1994).
Verri, et al., "Lack of Enantiospecificity of Human 2'-Deoxycytidine Kinase: Relevance for the Activation of B-L-Deoxycytidine Analogs as Antineoplastic and Antiviral Agents," Mol. Pharmacol., 51:132-138 (1997).
Verri, et al., "Relaxed Enantioselectivity of Human Mitochondrial Thymidine Kinase and Chemotherapeutic Uses of L-Nucleoside Analogues," Biochem. J., 328:317-320 (1997).
Victor E. Marquez, Ph.D. curriculum vitae.
Visser v. Hofvander, Interference 103,579, Final Decision (BPAI).
Vithanomsat et al., Southeast Asian J. Trop. Med. Public Health 15: 27-31 (1984).
Von Buren, et al., "Branched Oligodeoxynucleotides: Automated Synthesis and Triple Helical Hybridization Studies," Tetrahedron, 51:8491-8506 (1995).
Von Janta-Lipiniski, et al., "Newly Synthesized L-Enantiomers of 3'-Fluoro-Modified (3-2'-Deoxyribonucleoside 5'-Triphosphates Inhibit Hepatitis B DNA Polymerase but Not the Five Cellular DNA Polymerases α, β, γ, δ, and ε nor HIV-1 Reverse Transcriptase," J. Med. Chem., 41:2040-2046 (1998).
Vorbrüggen and Ruh-Pohlenz, Handbook of Nucleoside Synthesis (John Wiley & Sons., Inc., New York), pp. 140-141 and 403 (2001).
W.J. Middleton, J. Org. Chem. 40(5): 574-578 (1975).
Wachtmeister et al., Tetrahedron 55: 10761-10770 (1999).
Wagner, et al., "Preparation and Synthetic Utility of Some Organotin Derivatives of Nucleosides," J. Org. Chem., 39:24-30 (1974).
Wakita, T., et al., Production of infectious hepatitis C virus in tissue culture from a cloned viral genome, Nature Medicine, vol. 11, pp. 791-796 (2005).
Walczak, et al., "Synthesis of 1-(3-Alkyl-2,3-Dideoxy-D-Pentofuranosyl)Uracils with Potential Anti-HIV Activity," Acta Chem. Scand., 45:930-934 (1991).
Walker and Hong, "HCV RNA-dependent RNA polymerase as a target for antiviral development," Curr. Opin. Pharmacol., 2(5):534-540 (2002).
Walton et al., "Branched-Chain Sugar Nucleosides. A New Type of Biologically Active Nucleoside," J. Am. Chem. Soc., 88:4524-4525 (1966).
Walton, et al., "Branched-Chain Sugar Nucleosides: V. Synthesis and Antiviral Properties of Several Branched-Chain Sugar Nucleosides," J. Med. Chem. 12:306-309 (1969).
Wang et al., "Reactions of N-Acylimidazole with Nucleosides and Nucleotides," Heterocycles, 28:593-601 (1989).
Wang, Peiyuan, et al., An Efficient and Diastereoselective Synthesis of PSI-6130: A Clinically Efficacious Inhibitor of HCV NS5B Polymerase, J. Org. Chem., vol. 74, No. 17, pp. 6819-6824 (2009).
Watts and Damha, Can. J. Chem., 86: 641-656 (2008).
Weinberg, et al., "Effect of Antiviral Drugs and Hematopoietic Growth Factors on In Vitro Erythropoiesis," Mt. Sinai J. Med.; 65:5-13 (1998).
Whistler, et al., "α'-D-Glucosaccharino-1,4-Lactone," Methods in Carbohydrate Chemistry, 2:484-485 (1963).
Wilds and Damha, Nucleic Acids Res. 28(18): 3625-3635 (2000).
Wohlrab et al., Biochim. Biophys. Acta, 824: 233-42 (1985).
Wohnsland, et al., "Viral Determinants of Resistance to Treatment in Patients with Hepatitis C," Clin. Microbiol. Rev., 20:23-38 (2007).
Wolf, et al., "New 2'-C-Branched-Chain Sugar Nucleoside Analogs with Potential Antiviral or Antitumor Activity," Synthesis, 8:773-778 (1992).
Wolfe, et al., "A Concise Synthesis of 2'-C-Methylribonucleosides," Tetrahedron Lett., 36:7611-7614 (1995).
Wu, et al., "A New Stereospecific Synthesis of [3.1.0] Bicyclic Cyclopropano Analog of 2',3'-Dideoxyuridine," Tetrahedron, 46:2587-2592 (1990).
Wu, et al., "Targeting NS5B RNA-Dependent RNA Polymerase for Anti-HCV Chemotherapy," Curr. Drug Targets Infect. Disord., 3:207-219 (2003).
Wu, Hepatology 33: 1550-51 (2001).
Yamashita et al., J. Biol. Chem. 273: 15479-86 (1998).
Yanagi et al., Proc. Natl. Acad. Sci. USA 94: 8738-43 (1997).
Yanagi et al., Virology 244: 161-72 (1998).
Yang, Shu Shu, et al., Synthesis of DL-1-deoxy-fluoro-6-O-methyl-chiro-inositol: confirmation of a structural-DAST fluorination correlation, Carbohydrate Research, vol. 249, pp. 259-263 (1993).
Yarchoan, et al., "Long-Term Toxicity/Activity Profile of 2',3'-Dideoxyinosine in AIDS or AIDS-Related Complex," Lancet, 336:526-529 (1990).
Yi et al., Proc. Nat'l Acad. Sci. U.S.A. 103:2310-5 (2006).
Yi, MinKyung, et al., Subgenomic Hepatitis C Virus Replicons Inducing Expression of a Secreted Enzymatic Reporter Protein, Virology, vol. 304, pp. 197-210 (2002).
Yoo et al., J. Virol. 69: 32-38 (1995).
Yoshida, et al., "Reversal of Azidothymidine-Induced Bone Marrow Suppression by 2',3'-Dideoxythymidine as Studied by Hemopoietic Clonal Culture," AIDS Res. Hum. Retroviruses, 6:929-932 (1990).
Zedeck, et al., "Inhibition of the Steroid Induced Synthesis of Δ5-3-Ketosteroid Isomerase in Pseudomonas Testosteroni by a New Purine Deoxyribonucleoside Analog: 6-Chloro-8-Aza-9-Cyclopentylpurine," Mol. Phys., 3:386-395 (1967).
Zemlicka, et al., "Aminoacyl Derivatives of Nucleosides, Nucleotides, and Polynucleotides. VIII. The Preparation of 2'(3')-O-L-Phenylalanyluridine, -Cytidine, -Adenosine, -Inosine, -Guanosine and 2'-Deoxy-3'-O-L-Phenylalanyladenosine," Collect. Czech. Chem. Commun., 43:3755-3768 (1969).
Zemlicka, et al., "Substrate Specificity of Ribosomal Peptidyltransferase. Effect of Modifications in the Heterocyclic, Carbohydrate and Amino Acid Moiety of 2'(3)-O-L-Phenylalanyladenosine," Biochemistry., 14:5239-5279 (1975).
Zhou, et al., "Pharmacokinetics and Pharmacodynamics of Valopicitabine,". J. Hepatology, 42:229 (2005).
Zinchenko, et al., "[2'-, 3'- & .5'-Methyl Analogs of Uridine in the Reaction of Microbiologic Transglycosylation]," Dokl. Akad. Nauk. S.S.S.R., 297:731-734 (1987).
Zintchenko, et al., "Substrate Specificity of Uridine and Purine Nucleoside Phosphorylases of the Whole Cells of Escherichia coli," Nucleic Acids Symp. Ser., 18:137-140 (1987).
Zintchenko, et al., "Substrate Specificity of Uridine and Purine Nucleoside Phosphorylases in Whole Cells of Escherichia coli," Biopolymers & a cell, v. 4, No. 6 (1988).

(56) References Cited

OTHER PUBLICATIONS

Zon, "Cyclophosphamide Analogues," Chapter 4 in Progress in Medicinal Chemistry, vol. 19, G. P., Ellis and G. B. West, Eds., pp. 205-246 (1982).

Zuck, Paul, et al., A Cell-based β-lactamase Reporter Gene Assay for the Identification of Inhibitors of Hepatitis C Virus Replication, Analytical Biochemistry, vol. 344, pp. 344-355 (2004).

β-D-1'-CH₃-riboG

Ribavirin

β-D-1'-CH₃-riboA

FIAU

METHODS AND COMPOSITIONS FOR TREATING HEPATITIS C VIRUS

CROSS REFERENCE TO RELATED APPLICATIONS

This application is a continuation of U.S. application Ser. No. 13/730,669, filed on Dec. 28, 2012, which is a continuation of U.S. application Ser. No. 13/623,674, filed on Sep. 20, 2012, which is a continuation of U.S. application Ser. No. 12/504,601, filed on Jul. 16, 2009, which is a continuation of U.S. application Ser. No. 10/602,691, filed on Jun. 20, 2003, which is a continuation of U.S. application Ser. No. 09/864,078, filed on May 23, 2001, which claims the benefit of priority to U.S. Provisional Application No. 60/206,585, filed on May 23, 2000, the disclosure of each of which is incorporated herein by reference in its entirety.

FIELD OF THE INVENTION

This invention is in the area of pharmaceutical chemistry, and is in particular, is a compound, method and composition for the treatment of hepatitis C virus.

BACKGROUND OF THE INVENTION

The hepatitis C virus (HCV) is the leading cause of chronic liver disease worldwide. (Boyer, N. et al. *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, October: 80-85, (1999); Boyer, N. et al. *J. Hepatol.* 32:98-112, 2000). An estimated 170 million persons are infected with HCV worldwide. (Boyer, N. et al. *J. Hepatol.* 32:98-112, 2000). Cirrhosis caused by chronic hepatitis C infection accounts for 8,000-12,000 deaths per year in the United States, and HCV infection is the leading indication for liver transplant.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed toward the development of improved methods of treatment of chronic HCV infections in humans (Di Besceglie, A. M. and Bacon, B. R., *Scientific American*, October: 80-85, (1999)). Currently, there are two primary antiviral compounds, Ribavirin and interferon-alpha, which are used for the treatment of chronic HCV infections in humans.

Treatment of HCV Infection with Ribivarin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p 1304, 1989). U.S. Pat. No. 3,798,209 and RE29,835 disclose and claim Ribavirin. Ribavirin is structurally similar to guanosine, and has in vitro activity against several DNA and RNA viruses including Flaviviridae (Gary L. Davis. Gastroenterology 118:S104-S114, 2000).

Ribavirin reduces serum amino transferase levels to normal in 40% or patients, but it does not lower serum levels of HCV-RNA (Gary L. Davis. Gastroenterology 118:S104-S114, 2000). Thus, Ribavirin alone is not effective in reducing viral RNA levels. Additionally, Ribavirin has significant toxicity and is known to induce anemia.

Treatment of HCV Infection with Interferon

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Gary L. Davis. *Gastroenterology* 118:S104-S114, 2000).

A number of patents disclose HCV treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696.

Combination of Interferon and Ribavirin

The combination of IFN and Ribavirin for the treatment of HCV infection has been reported to be effective in the treatment of IFN naïve patients (Battaglia, A. M. et al., *Ann. Pharmacother.* 34:487-494, 2000). Results are promising for this combination treatment both before hepatitis develops or when histological disease is present (Berenguer, M. et al. *Antivir. Ther.* 3(Suppl. 3):125-136, 1998). Side effects of combination therapy include hemolysis, flu-like symptoms, anemia, and fatigue. (Gary L. Davis. Gastroenterology 118: S104-S114, 2000).

Additional References Disclosing Methods to Treat HCV Infections

A number of HCV treatments are reviewed by Bymock et al. in *Antiviral Chemistry & Chemotherapy*, 11:2; 79-95 (2000).

Several substrate-based NS3 protease inhibitors have been identified in the literature, in which the scissile amide bond of a cleaved substrate is replaced by an electrophile, which interacts with the catalytic serine. Attwood et al. (1998) *Antiviral peptide derivatives*, 98/22496; Attwood et al. (1999), *Antiviral Chemistry and Chemotherapy* 10.259-273; Attwood et al. (1999) Preparation and use of amino acid derivatives as anti-viral agents, German Patent Publication DE 19914474; Tung et al. (1998) Inhibitors of serine proteases, particularly hepatitis C virus NS3 protease, WO 98/17679. The reported inhibitors terminate in an electrophile such as a boronic acid or phosphonate. Llinas-Brunet et al. (1999) Hepatitis C inhibitor peptide analogues, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) *Biochemical and Biophysical Research Communications*, 238:643-647; Sudo, K. et al. (1998) *Antiviral Chemistry and Chemotherapy* 9:186. Using a reverse-phase HPLC assay, the two most potent compounds identified were RD3-4082 and RD3-4078, the former substituted on the amide with a 14 carbon chain and the latter processing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al. (1996) *Antiviral Research* 32:9-18. Compound RD-1-6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al. *J. EBS Letters* 421:217-220; Takeshita N. et al., *Analytical Biochemistry* 247:242-246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenan-threnequinone, possessed micromolar activity against HCV protease in a SDS-PAGE and autoradiography assay. Chu M. et al., *Tetrahedron Letters* 37:7229-7232, 1996. In another example by the same authors, Sch 351633, isolated from the fungus *Penicillium griscofuluum*, demonstrated micromolar activity in a scintillation proximity assay. Chu M. et al., *Bioorganic and Medicinal Chemistry Letters* 9:1949-1952. Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

HCV helicase inhibitors have also been reported. U.S. Pat. No. 5,633,358 to Diana G. D. et al.; PCT Publication No. WO 97/36554 of Diana G. D. et al. There are a few reports of HCV polymerase inhibitors: some nucleotide analogues, gliotoxin and the natural product cerulenin. Ferrari R. et al., *Journal of Virology* 73:1649-1654, 1999; Lohmann V. et al., *Virology* 249:108-118, 1998.

Antisense phosphorothioate oligodeoxynucleotides complementary to sequence stretches in the 5' non-coding region of the HCV, are reported as efficient inhibitors of HCV gene expression in in vitro translation and IIcpG2 IICV-luciferase cell culture systems. Alt M. et al., *Hepatology* 22:707-717, 1995. Recent work has demonstrated that nucleotides 326-348 comprising the 3' end of the NCR and nucleotides 371-388 located in the core coding region of the HCV RNA are effective targets for antisense-mediated inhibition of viral translation. Alt M. et al., *Archives of Virology* 142:589-599, 1997. U.S. Pat. No. 6,001,990 to Wands et al. discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV-RNA. U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., *Journal of Cellular Physiology* 181:251-257, 1999).

Other compounds have been reported as inhibitors of IRES-dependent translation in HCV. Japanese Patent Publication JP-08268890 of Ikeda N et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., *Hepatology* 30 abstract 995, 1999. The use of ribozymes to treat HCV is also disclosed in U.S. Pat. No. 6,043,077 to Barber et al., and U.S. Pat. Nos. 5,869,253 and 5,610,054 to Draper et al.

Other patents disclose the use of immune system potentiating compounds for the treatment of HCV. For example, U.S. Pat. No. 6,001,799 to Chretien et al. discloses a method of treating hepatitis C in non-responders to interferon treatment by administering an immune system potentiating dose of thymosin or a thymosin fragment. U.S. Pat. No. 5,972,347 to Eder et al. and U.S. Pat. No. 5,969,109 to Bona et al. disclose antibody-based treatments for treating HCV.

U.S. Pat. No. 6,034,134 to Gold et al. discloses certain NMDA receptor agonists having immunodulatory, antimalarial, anti-Borna virus and anti-Hepatitis C activities. The disclosed NMDA receptor agonists belong to a family of 1-amino-alkylcyclohexanes. U.S. Pat. No. 6,030,960 to Morris-Natschke et al. discloses the use of certain alkyl lipids to inhibit the production of hepatitis-induced antigens, including those produced by the HCV virus. U.S. Pat. No. 5,922,757 to Chojkier et al. discloses the use of vitamin E and other antioxidants to treat hepatic disorders including HCV. U.S. Pat. No. 5,858,389 to Elsherbi et al. discloses the use of squalene for treating hepatitis C. U.S. Pat. No. 5,849,800 to Smith et al discloses the use of amantadine for treatment of Hepatitis C. U.S. Pat. No. 5,846,964 to Ozeki et al. discloses the use of bile acids for treating HCV. U.S. Pat. No. 5,491,135 to Blough et al. discloses the use of N-(phosphonoacetyl)-L-aspartic acid to treat flaviviruses such as HCV.

Other compounds proposed for treating HCV include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.).

In light of the fact that the hepatitis C virus has reached epidemic levels worldwide, and has tragic effects on the infected patient, there remains a strong need to provide new effective pharmaceutical agents to treat hepatitis C that has low toxicity to the host.

Therefore, it is an object of the present invention to provide a compound, method and composition for the treatment of a host infected with hepatitis C virus.

SUMMARY OF THE INVENTION

Compounds, methods and compositions for the treatment of hepatitis C infection are described that include an effective hepatitis C treatment amount of a β-D- or β-L-nucleoside of the Formulas (I)-(XVIII), or a pharmaceutically acceptable salt or prodrug thereof.

In a first principal embodiment, a compound of Formula I, or a pharmaceutically acceptable salt or prodrug thereof, is provided:

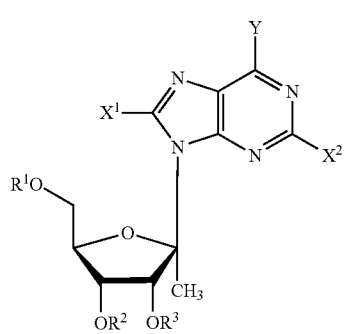

(I)

wherein:
$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a second principal embodiment, a compound of Formula II, or a pharmaceutically acceptable salt or prodrug thereof, is provided:

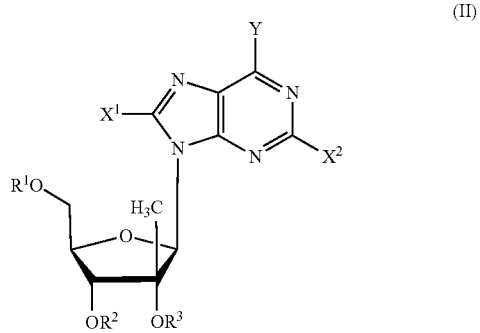

(II)

wherein:
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a third principal embodiment, a compound of Formula III, or a pharmaceutically acceptable salt or prodrug thereof, is provided:

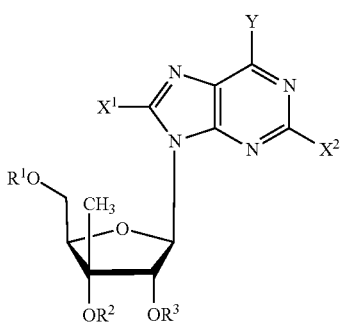

(III)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fourth principal embodiment, a compound of Formula IV, or a pharmaceutically acceptable salt or prodrug thereof, is provided:

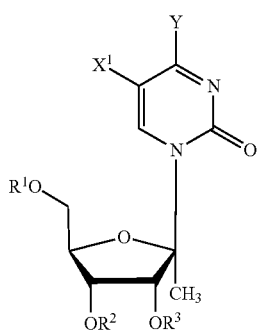

(IV)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fifth principal embodiment, a compound of Formula V, or a pharmaceutically acceptable salt or prodrug thereof, is provided:

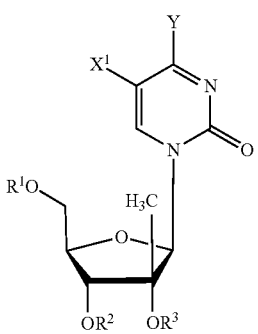

(V)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a sixth principal embodiment, a compound of Formula VI, or a pharmaceutically acceptable salt or prodrug thereof, is provided:

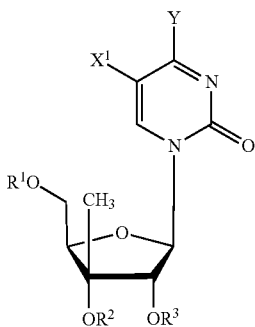

wherein:

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate; and Y is hydrogen, bromo, chloro, fluoro, iodo, OR⁴, NR⁴R⁵ or SR⁴;

X¹ is selected from the group consisting of H, straight chained, branched or cyclic alkyl, CO-alkyl, CO-aryl, CO-alkoxyalkyl, chloro, bromo, fluoro, iodo, OR⁴, NR⁴NR⁵ or SR⁵; and R⁴ and R⁵ are independently hydrogen, acyl (including lower acyl), or alkyl (including but not limited to methyl, ethyl, propyl and cyclopropyl).

In a seventh principal embodiment, a compound selected from Formulas VII, VIII and IX, or a pharmaceutically acceptable salt or prodrug thereof, is provided:

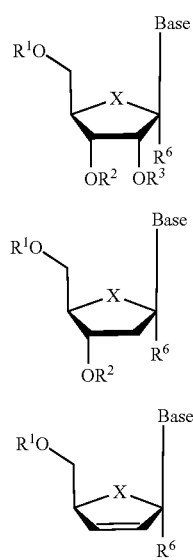

wherein:

Base is a purine or pyrimidine base as defined herein;

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate;

R⁶ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), CF₃, chloro, bromo, fluoro, iodo, NO₂, NH₂, —NH(lower alkyl), —NH(acyl), —N(lower alkyl)₂, —N(acyl)₂; and X is O, S, SO₂ or CH₂.

In a eighth principal embodiment, a compound of Formulas X, XI and XII, or a pharmaceutically acceptable salt or prodrug thereof, is provided:

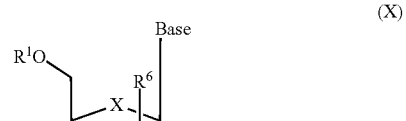

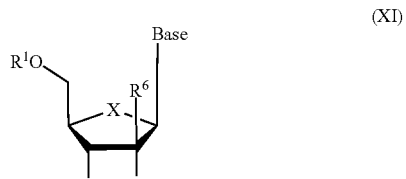

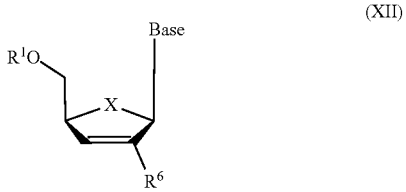

wherein:

Base is a purine or pyrimidine base as defined herein;

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂;

R⁷ is hydrogen, OR³, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO₂, NH₂, —NH(lower alkyl), —NH(acyl), —N(lower alkyl)₂, —N(acyl)₂; and X is O, S, SO₂ or CH₂.

In a ninth principal embodiment a compound selected from Formulas XIII, XIV and XV, or a pharmaceutically acceptable salt or prodrug thereof, is provided:

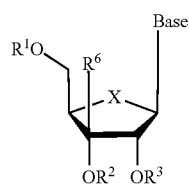

(XIII)

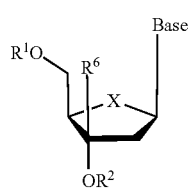

(XIV)

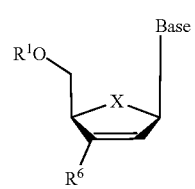

(XV)

wherein:

Base is a purine or pyrimidine base as defined herein;

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂; and X is O, S, SO₂ or CH₂.

In a tenth principal embodiment the invention provides a compound of Formula XVI, or a pharmaceutically acceptable salt or prodrug thereof:

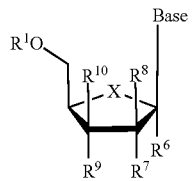

(XVI)

wherein:

Base is a purine or pyrimidine base as defined herein;

R¹ and R² are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ or R² is independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂;

R⁷ and R⁹ are independently hydrogen, OR², hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO₂, NH₂, —NH(lower alkyl), —NH(acyl), —N(lower alkyl)₂, —N(acyl)₂;

R⁸ and R¹⁰ are independently H, alkyl (including lower alkyl), chlorine, bromine or iodine;

alternatively, R⁷ and R⁹, R⁷ and R¹', R⁸ and R⁹, or R⁸ and R¹⁰ can come together to form a pi bond; and X is O, S, SO₂ or CH₂.

In a eleventh principal embodiment the invention provides a compound of Formula XVII, or a pharmaceutically acceptable salt or prodrug thereof:

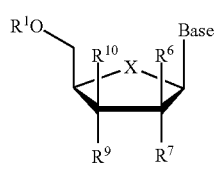

(XVII)

wherein:

Base is a purine or pyrimidine base as defined herein;

R¹ and R² are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;
$R^{10}$ is H, alkyl (including lower alkyl), chlorine, bromine or iodine;
alternatively, $R^7$ and $R^9$, or $R^7$ and $R^{10}$ can come together to form a pi bond; and
X is O, S, $SO_2$ or $CH_2$.

In an twelfth principal embodiment, the invention provides a compound of Formula XVIII, or a pharmaceutically acceptable salt or prodrug thereof:

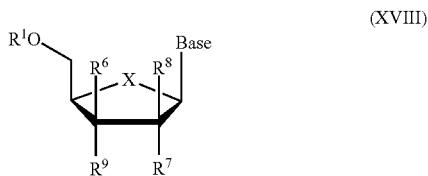

(XVIII)

wherein:
Base is a purine or pyrimidine base as defined herein;
$R^1$ and $R^2$ independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(lower-alkyl)amino;
$R^8$ is H, alkyl (including lower alkyl), chlorine, bromine or iodine;
alternatively, $R^7$ and $R^9$, or $R^8$ and $R^9$ can come together to form a pi bond;
X is O, S, $SO_2$ or $CH_2$.

The β-D- and β-L-nucleosides of this invention may inhibit HCV polymerase activity. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 25, 15, 10, 5, or 1 micromolar.

In another embodiment, the active compound can be administered in combination or alternation with another anti-HCV agent. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include:

(1) an interferon and/or ribavirin (Battaglia, A. M. et al., Ann. Pharmacother. 34:487-494, 2000); Berenguer, M. et al. Antivir. Ther. 3(Suppl. 3): 125-136, 1998);

(2) Substrate-based NS3 protease inhibitors (Attwood et al., Antiviral peptide derivatives, PCT WO 98/22496, 1998; Attwood et al., Antiviral Chemistry and Chemotherapy 10.259-273, 1999; Attwood et al., Preparation and use of amino acid derivatives as anti-viral agents, German Patent Publication DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

(3) Non-substrate-based inhibitors such as 2,4,6-trihydroxy-3-nitro-benzamide derivatives (Sudo K. et al., Biochemical and Biophysical Research Communications, 238: 643-647, 1997; Sudo K. et al. Antiviral Chemistry and Chemotherapy 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., Antiviral Research 32:9-18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. J. EBS Letters 421:217-220; Takeshita N. et al. Analytical Biochemistry 247:242-246, 1997;

(6) A phenan-threnequinone possessing activity against HCV protease in a SDS-PAGE and autoradiography assay isolated from the fermentation culture broth of Streptomyces sp., Sch 68631 (Chu M. et al., Tetrahedron Letters 37:7229-7232, 1996), and Sch 351633, isolated from the fungus Penicillium griscofuluum, which demonstrates activity in a scintillation proximity assay (Chu M. et al., Bioorganic and Medicinal Chemistry Letters 9:1949-1952);

(7) Selective NS3 inhibitors based on the macromolecule elgin c, isolated from leech (Qasim M. A. et al., *Biochemistry* 36:1598-1607, 1997);

(8) HCV helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) HCV polymerase inhibitors such as nucleotide analogues, gliotoxin (Ferrari R. et al. *Journal of Virology* 73:1649-1654, 1999), and the natural product cerulenin (Lohmann V. et al., *Virology* 249:108-118, 1998);

(10) Antisense phosphorothioate oligodeoxynucleotides (S-ODN) complementary to sequence stretches in the 5' non-coding region (NCR) of the HCV (Alt M. et al., *Hepatology* 22:707-717, 1995), or nucleotides 326-348 comprising the 3' end of the NCR and nucleotides 371-388 located in the core coding region of the IICV RNA (Alt M. et al., *Archives of Virology* 142:589-599, 1997; Galderisi U. et al., *Journal of Cellular Physiology* 181:251-257, 1999);

(11) Inhibitors of IRES-dependent translation (Ikeda N et al., Agent for the prevention and treatment of hepatitis C, Japanese Patent Publication JP-08268890; Kai Y. et al. Prevention and treatment of viral diseases, Japanese Patent Publication JP-10101591);

(12) Nuclease-resistant ribozymes (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

DETAILED DESCRIPTION OF THE INVENTION

Figure 1:
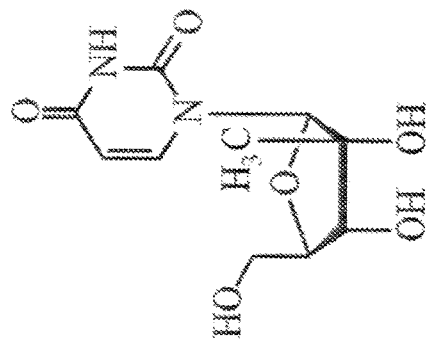
FIG. 1 provides the structure of various non-limiting examples of nucleosides of the present invention, as well as other known nucleosides, FIAU and Ribavirin, which are used as comparative examples in the text.
Figure 1:
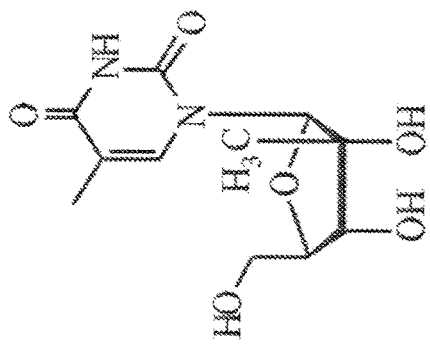
Figure 1:
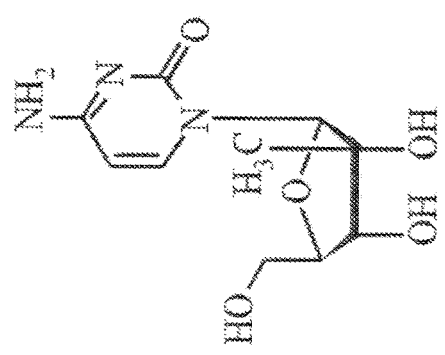
Figure 1:
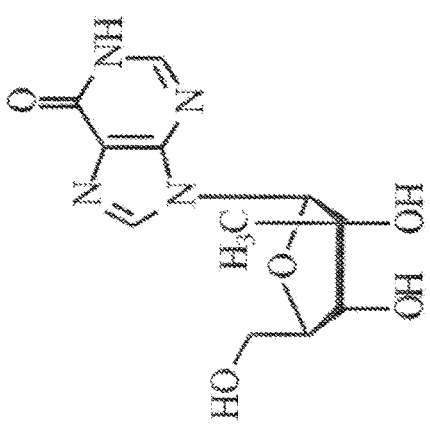
Figure 1:
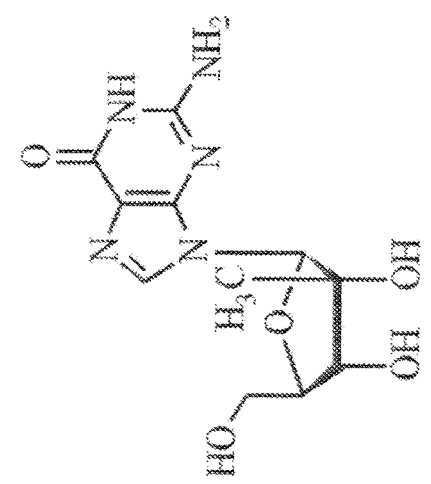
Figure 1:
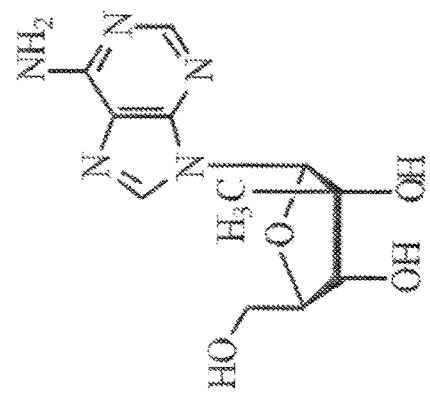
Figure 1:
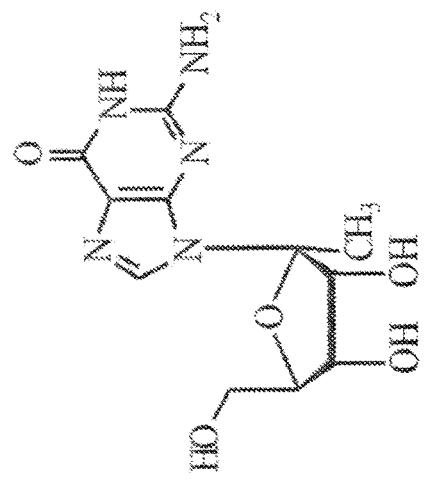
Figure 1:
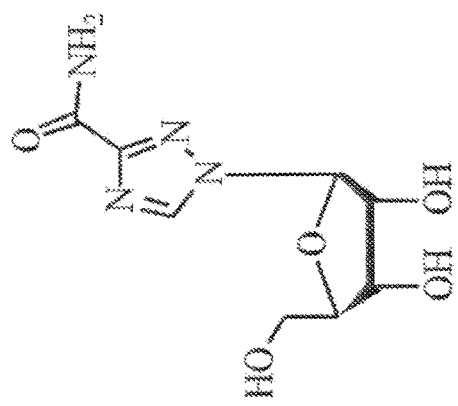
Figure 1:
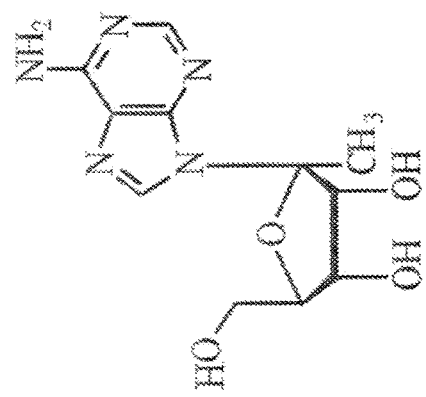
Figure 1:
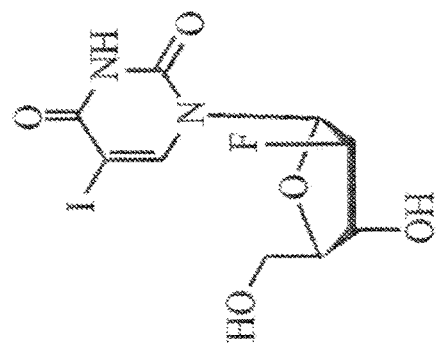

The invention as disclosed herein is a compound, method and composition for the treatment of hepatitis C in humans or other host animals, that includes administering an effective HCV treatment amount of a β-D- or β-L-nucleoside as described herein or a pharmaceutically acceptable salt or prodrug thereof, optionally in a pharmaceutically acceptable carrier. The compounds of this invention either possess antiviral (i.e., anti-HCV) activity, or are metabolized to a compound that exhibits such activity.

In summary, the present invention includes the following features:

(a) β-D- and β-L-nucleosides, as described herein, and pharmaceutically acceptable salts and prodrugs thereof;

(b) β-D- and β-L-nucleosides as described herein, and pharmaceutically acceptable salts and prodrugs thereof for use in the treatment or prophylaxis of an HCV infection, especially in individuals diagnosed as having an HCV infection or being at risk for becoming infected by HCV;

(c) use of these β-D- and β-L-nucleosides, and pharmaceutically acceptable salts and prodrugs thereof in the manufacture of a medicament for treatment of an HCV infection;

(d) pharmaceutical formulations comprising the β-D- or β-L-nucleosides or pharmaceutically acceptable salts or prodrugs thereof together with a pharmaceutically acceptable carrier or diluent;

(e) β-D- and β-L-nucleosides as described herein substantially in the absence of enantiomers of the described nucleoside, or substantially isolated from other chemical entities;

(f) processes for the preparation of β-D- and β-L-nucleosides, as described in more detail below; and (g) processes for the preparation of β-D- and β-L-nucleosides substantially in the absence of enantiomers of the described nucleoside, or substantially isolated from other chemical entities.

I. Active Compound, and Physiologically Acceptable Salts and Prodrugs Thereof

In a first principal embodiment, a compound of Formula I, or a pharmaceutically acceptable salt or prodrug thereof, is provided:

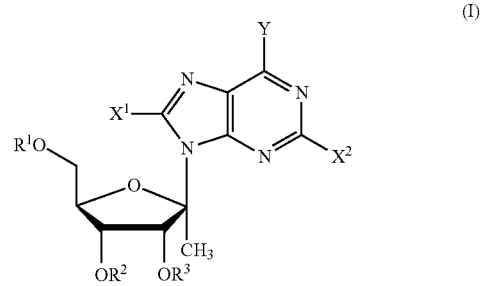

(I)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula I, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a second principal embodiment, a compound of Formula II, or a pharmaceutically acceptable salt or prodrug thereof, is provided:

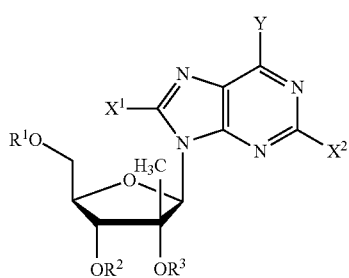

(II)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula II, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a third principal embodiment, a compound of Formula III, or a pharmaceutically acceptable salt or prodrug thereof, is provided:

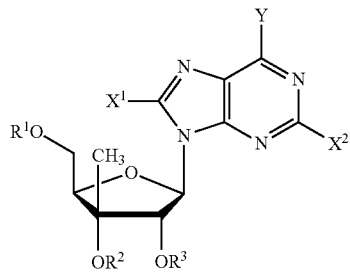

(III)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula III, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a fourth principal embodiment, a compound of Formula IV, or a pharmaceutically acceptable salt or prodrug thereof, is provided:

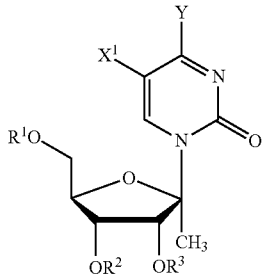

(IV)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula IV, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a fifth principal embodiment, a compound of Formula V, or a pharmaceutically acceptable salt or prodrug thereof, is provided:

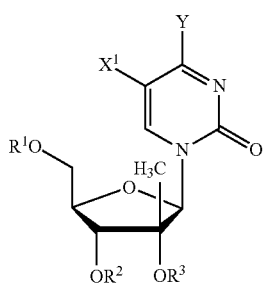

(V)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula V, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a sixth principal embodiment, a compound of Formula VI, or a pharmaceutically acceptable salt or prodrug thereof, is provided:

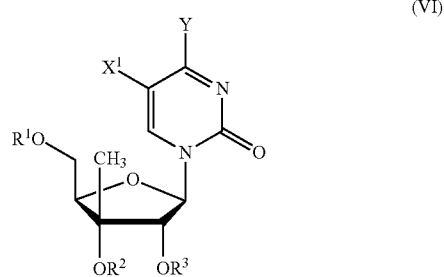

(VI)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula VI, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a seventh principal embodiment, a compound selected from Formulas VII, VIII and IX, or a pharmaceutically acceptable salt or prodrug thereof, is provided:

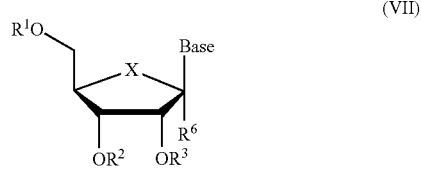

(VII)

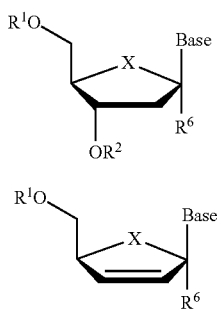

(VIII)

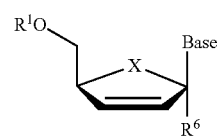

(IX)

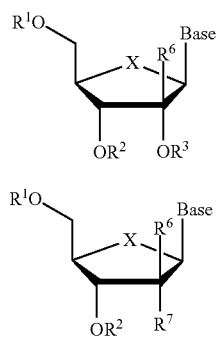

(X)

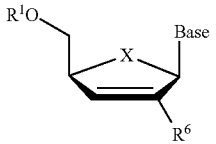

(XI)

(XII)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$, or $CH_2$.

In a first preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O, S, $SO_2$ or $CH_2$.

In a second preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are hydrogens;

$R^6$ is alkyl; and

X is O, S, $SO_2$ or $CH_2$.

In a third preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O.

In a eighth principal embodiment, a compound of Formula X, XI or XII, or a pharmaceutically acceptable salt or prodrug thereof, is provided:

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(loweralkyl)$_2$, —N(acyl)$_2$; and X is O, S, $SO_2$ or $CH_2$.

In a first preferred subembodiment, a compound of Formula X, XI or XII, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O, S, $SO_2$ or $CH_2$.

In a second preferred subembodiment, a compound of Formula X, XI or XII, or a pharmaceutically acceptable salt or prodrug thereof, is provided wherein:

Base is a purine or pyrimidine base as defined herein;

$R^1$, $R^2$ and $R^3$ are hydrogens;

$R^6$ is alkyl; and

X is O, S, $SO_2$ or $CH_2$.

In a third preferred subembodiment, a compound of Formula X, XI or XII, or a pharmaceutically acceptable salt or prodrug thereof, is provided wherein:

Base is a purine or pyrimidine base as defined herein;
$R^1$, $R^2$ and $R^3$ are independently H or phosphate;
$R^6$ is alkyl; and
X is O.

In even more preferred subembodiments, a compound of Formula XI, or its pharmaceutically acceptable salt or prodrug, is provided:

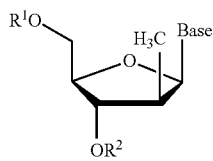

(XI)

wherein:
Base is a purine or pyrimidine base as defined herein; optionally substituted with an amine or cyclopropyl (e.g., 2-amino, 2,6-diamino or cyclopropyl guanosine); and
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate.

In a ninth principal embodiment a compound selected from Formula XIII, XIV or XV, or a pharmaceutically acceptable salt or prodrug thereof, is provided:

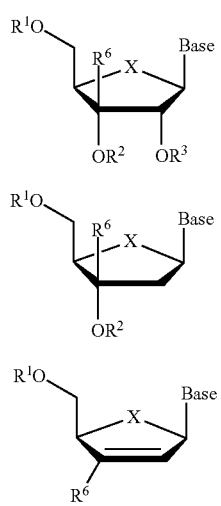

(XIII)

(XIV)

(XV)

wherein:
Base is a purine or pyrimidine base as defined herein;
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$; and
X is O, S, $SO_2$ or $CH_2$.

In a first preferred subembodiment, a compound of Formula XIII, XIV or XV, or a pharmaceutically acceptable salt or prodrug thereof, is provided wherein:
Base is a purine or pyrimidine base as defined herein;
$R^1$, $R^2$ and $R^3$ are independently hydrogen or phosphate;
$R^6$ is alkyl; and
X is O, S, $SO_2$ or $CH_2$.

In a second preferred subembodiment, a compound of Formula XIII, XIV or XV, or a pharmaceutically acceptable salt or prodrug thereof, is provided wherein:
Base is a purine or pyrimidine base as defined herein;
$R^1$, $R^2$ and $R^3$ are hydrogens;
$R^6$ is alkyl; and
X is O, S, $SO_2$ or $CH_2$.

In a third preferred subembodiment, a compound of Formula XIII, XIV or XV, or a pharmaceutically acceptable salt or prodrug thereof, is provided wherein:
Base is a purine or pyrimidine base as defined herein;
$R^1$, $R^2$ and $R^3$ are independently hydrogen or phosphate;
$R^6$ is alkyl; and
X is O.

In a tenth principal embodiment the invention provides a compound of Formula XVI, or a pharmaceutically acceptable salt or prodrug thereof:

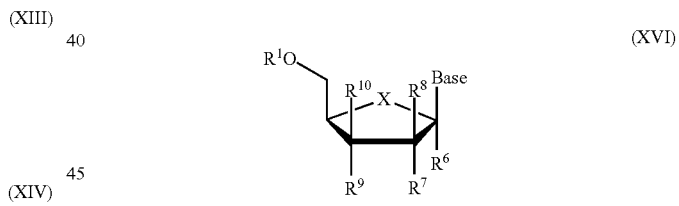

(XVI)

wherein:
Base is a purine or pyrimidine base as defined herein;
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ and $R^2$ are independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH (lower alkyl), —NH(acyl), —N(lower alkyl)$_2$, —N(acyl)$_2$; $R^8$ and $R^{10}$ are independently H, alkyl (including lower alkyl), chlorine, bromine or iodine;

alternatively, $R^7$ and $R^9$, $R^7$ and $R^{1'}$, $R^8$ and $R^9$, or $R^8$ and $R^{10}$ can come together to form a pi bond; and X is O, S, $SO_2$ or $CH_2$.

In a first preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine, or iodine; and (6) X is O, S, $SO_2$ or $CH_2$.

In a second preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ and $R^{10}$ are independently H, alkyl (including lower alkyl), chlorine, bromine, or iodine; and (6) X is O, S, $SO_2$ or $CH_2$.

In a third preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are H; and (6) X is O, S, $SO_2$ or $CH_2$.

In a fourth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are independently H, alkyl (including lower alkyl), chlorine, bromine, or iodine; and (6) X is O.

In a fifth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^1$; (5) $R^8$ and $R^{10}$ are independently H, alkyl (including lower alkyl), chlorine, bromine or iodine; and (6) X is O, S, $SO_2$ or $CH_2$.

In a sixth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are H; and (6) X is O, S, $SO_2$, or $CH_2$.

In a seventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine or iodine; and (6) X is O.

In an eighth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a ninth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are independently H, alkyl (including lower alkyl), chlorine, bromine or iodine; and (6) X is O.

In a tenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are hydrogen; and (6) X is O.

In an eleventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a twelfth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ and $R^{10}$ are hydrogen; and (6) X is O, S, $SO_2$, or $CH_2$.

In a thirteenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ and $R^{10}$ are independently H, alkyl (including lower alkyl), chlorine, bromine, or iodine; and (6) X is O.

In a fourteenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are hydrogen; and (6) X is O.

In even more preferred subembodiments, a compound of Formula XVI, or its pharmaceutically acceptable salt or prodrug, is provided in which: (1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is guanine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is cytosine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is thymine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is uracil; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is adenine; (2) $R^6$ is phosphate; (3) $R^6$ is methyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is ethyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is propyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is butyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is methyl; (4) $R^7$ is hydrogen and $R^9$ is hydroxyl; (5) $R^8$ and $R^{10}$ are hydrogen; and (6) X is O; (1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is S;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $SO_2$;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $CH_2$;

In a eleventh principal embodiment the invention provides a compound of Formula XVII, or a pharmaceutically acceptable salt or prodrug thereof:

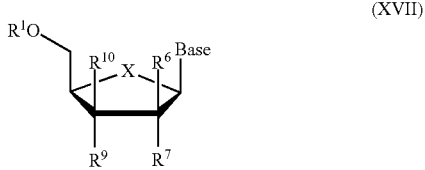

(XVII)

wherein:
Base is a purine or pyrimidine base as defined herein;
$R^1$ is H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH (lower alkyl), —NH(acyl), —N(lower alkyl)$_2$, —N(acyl)$_2$;
$R^{10}$ is H, alkyl (including lower alkyl), chlorine, bromine, or iodine;

alternatively, $R^7$ and $R^9$, or $R^7$ and $R^{10}$ can come together to form a pi bond; and
X is O, S, $SO_2$ or $CH_2$.

In a first preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H; and (6) X is O, S, $SO_2$, or $CH_2$.

In a second preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine, or iodine; and (6) X is O, S, $SO_2$ or $CH_2$.

In a third preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O.

In a fourth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H; and (6) X is O, S, $SO_2$ or $CH_2$.

In a fifth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine or iodine; and (6) X is O.

In a sixth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^{10}$ is H; and (6) X is O.

In a seventh preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O.

In an eighth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O, S, $SO_2$, or $CH_2$.

In a ninth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O, S, $SO_2$, or $CH_2$.

In a tenth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^{10}$ is H; and (6) X is O, S, $SO_2$, or $CH_2$.

In even more preferred subembodiments, a compound of Formula XVII, or its pharmaceutically acceptable salt or prodrug, is provided in which: (1) Base is adenine; (2) $R^1$ is hydrogen; (3) $R^6$ is methyl; (4) $R^7$ and $R^9$ are hydroxyl; (5) $R^{10}$ is hydrogen; and (6) X is O;

(1) Base is guanine; (2) $R^1$ is hydrogen; (3) $R^6$ is methyl; (4) $R^7$ and $R^9$ are hydroxyl; (5) $R^{10}$ is hydrogen; and (6) X is O;

(1) Base is cytosine; (2) $R^1$ is hydrogen; (3) $R^6$ is methyl; (4) $R^7$ and $R^9$ are hydroxyl; (5) $R^{10}$ is hydrogen; and (6) X is O;

(1) Base is thymine; (2) $R^1$ is hydrogen; (3) $R^6$ is methyl; (4) $R^7$ and $R^9$ are hydroxyl; (5) $R^{10}$ is hydrogen; and (6) X is O;

(1) Base is uracil; (2) $R^1$ is hydrogen; (3) $R^6$ is methyl; (4) $R^7$ and $R^9$ are hydroxyl; (5) $R^{10}$ is hydrogen; and (6) X is O;

(1) Base is adenine; (2) $R^1$ is phosphate; (3) $R^6$ is methyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is ethyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is propyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is butyl; (4) $R^1$ and $R^9$ are hydroxyl; (5) $R^{10}$ is hydrogen; and (6) X is O;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is S;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^{10}$ is hydrogen; and (6) X is $CH_2$.

In an twelfth principal embodiment the invention provides a compound of Formula XVIII, or a pharmaceutically acceptable salt or prodrug thereof:

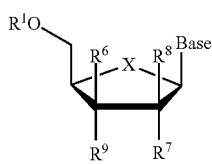

(XVIII)

wherein:
Base is a purine or pyrimidine base as defined herein;
$R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, lower alkylamino, or di(loweralkyl)amino;
$R^8$ is H, alkyl (including lower alkyl), chlorine, bromine or iodine;
alternatively, $R^1$ and $R^9$, or $R^8$ and $R^9$ can come together to form a pi bond;
X is O, S, $SO_2$ or $CH_2$.

In a first preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^1$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ is H, alkyl (including lower alkyl), chlorine, bromine or iodine; and (6) X is O, S, $SO_2$ or $CH_2$.

In a second preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H, alkyl (including lower alkyl), chlorine, bromine, or iodine; and (6) X is O, S, $SO_2$ or $CH_2$.

In a third preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(lower-alkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O, S, $SO_2$ or $CH_2$.

In a fourth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H, alkyl (including lower alkyl), chlorine, bromine, or iodine; and (6) X is O.

In a fifth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ is H; and (6) X is O, S, $SO_2$, or $CH_2$.

In a sixth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ is H, alkyl (including lower alkyl), chlorine, bromine, or iodine; and (6) X is O.

In a seventh preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O.

In an eighth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H; and (6) X is O, S, $SO_2$ or $CH_2$.

In a ninth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ is H; and (6) X is O, S, $SO_2$, or $CH_2$.

In a tenth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ is H; and (6) X is O.

In even more preferred subembodiments, a compound of Formula XVIII, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^8$ is hydrogen; and (6) X is O;

(1) Base is guanine; (2) $R^1$ is hydrogen; (3) $R^6$ is methyl; (4) $R^7$ and $R^9$ are hydroxyl; (5) $R^8$ is hydrogen; and (6) X is O;

(1) Base is cytosine; (2) $R^1$ is hydrogen; (3) $R^6$ is methyl; (4) $R^7$ and $R^9$ are hydroxyl; (5) $R^8$ is hydrogen; and (6) X is O;

(1) Base is thymine; (2) $R^1$ is hydrogen; (3) $R^6$ is methyl; (4) $R^7$ and $R^9$ are hydroxyl; (5) $R^8$ is hydrogen; and (6) X is O;

(1) Base is uracil; (2) $R^1$ is hydrogen; (3) $R^6$ is methyl; (4) $R^7$ and $R^9$ are hydroxyl; (5) $R^8$ is hydrogen; and (6) X is O;

(1) Base is adenine; (2) $R^1$ is phosphate; (3) $R^6$ is methyl; (4) $R^7$ and $R^9$ are hydroxyl; (5) $R^8$ is hydrogen; and (6) X is O;

(1) Base is adenine; (2) $R^1$ is hydrogen; (3) $R^6$ is ethyl; (4) $R^7$ and $R^9$ are hydroxyl; (5) $R^8$ is hydrogen; and (6) X is O;

(1) Base is adenine; (2) $R^1$ is hydrogen; (3) $R^6$ is propyl; (4) $R^7$ and $R^9$ are hydroxyl; (5) $R^8$ is hydrogen; and (6) X is O;

(1) Base is adenine; (2) $R^1$ is hydrogen; (3) $R^6$ is butyl; (4) $R^7$ and $R^9$ are hydroxyl; (5) $R^8$ is hydrogen; and (6) X is O;

(1) Base is adenine; (2) $R^1$ is hydrogen; (3) $R^6$ is methyl; (4) $R^7$ and $R^9$ are hydroxyl; (5) $R^8$ is hydrogen; and (6) X is S;

(1) Base is adenine; (2) $R^1$ is hydrogen; (3) $R^6$ is methyl; (4) $R^7$ and $R^9$ are hydroxyl; (5) $R^8$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^8$ is hydrogen; and (6) X is $CH_2$.

The β-D- and β-L-nucleosides of this invention may inhibit HCV polymerase activity. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar, when measured according to the polymerase assay described in Ferrari et al., *Jnl. of Vir.,* 73:1649-1654, 1999; Ishii et al., *Hepatology,* 29:1227-1235,1999; Lohmann et al., *Jnl. of Bio. Chem.,* 274:10807-10815, 1999; or Yamashita et al, *Jnl. of Bio. Chem.,* 273:15479-15486, 1998.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound that has been alkylated or acylated at the 5'-position or on the purine or pyrimidine base (a type of "pharmaceutically acceptable prodrug").

Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

II. Definitions

The term alkyl, as used herein, unless otherwise specified, refers to a saturated straight, branched, or cyclic, primary, secondary, or tertiary hydrocarbon of typically $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is a lower alkyl.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside.

In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "independently" is used herein to indicate that the variable which is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term host, as used herein, refers to an unicellular or multicellular organism in which the virus can replicate, including cell lines and animals, and preferably a human. Alternatively, the host can be carrying a part of the hepatitis C viral genome, whose replication or function can be altered by the compounds of the present invention. The term host specifically refers to infected cells, cells transfected with all or part of the HCV genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against HCV, or are metabolized to a compound that exhibits such activity.

III. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research,* 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); 5,194,654 (Mar. 16, 1993, Hostetler et al., U.S. Pat. No. 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

IV. Combination and Alternation Therapy

It has been recognized that drug-resistant variants of HCV can emerge after prolonged treatment with an antiviral agent. Drug resistance most typically occurs by mutation of a gene that encodes for an enzyme used in viral replication. The efficacy of a drug against HCV infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Nonlimiting examples of antiviral agents that can be used in combination with the compounds disclosed herein include:

(1) an interferon and/or ribavirin (Battaglia, A. M. et al., Ann. Pharmacother. 34:487-494, 2000); Berenguer, M. et al. Antivir. Ther. 3(Suppl. 3): 125-136, 1998);

(2) Substrate-based NS3 protease inhibitors (Attwood et al., Antiviral peptide derivatives, PCT WO 98/22496, 1998; Attwood et al., Antiviral Chemistry and Chemotherapy 10.259-273, 1999; Attwood et al., Preparation and use of amino acid derivatives as anti-viral agents, German Patent Publication DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

(3) Non-substrate-based inhibitors such as 2,4,6-trihydroxy-3-nitro-benzamide derivatives (Sudo K. et al., Biochemical and Biophysical Research Communications, 238: 643-647, 1997; Sudo K. et al. Antiviral Chemistry and Chemotherapy 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., Antiviral Research 32:9-18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. J EBS Letters 421:217-220; Takeshita N. et al. Analytical Biochemistry 247:242-246, 1997; (6) A phenanthrenequinone possessing activity against HCV protease in a SDS-PAGE and autoradiography assay isolated from the fermentation culture broth of Streptomyces sp., Sch 68631 (Chu M. et al., Tetrahedron Letters 37:7229-7232, 1996), and Sch 351633, isolated from the fungus Penicillium griscofuluum, which demonstrates activity in a scintillation proximity assay (Chu M. et al., Bioorganic and Medicinal Chemistry Letters 9:1949-1952);

(7) Selective NS3 inhibitors based on the macromolecule elgin c, isolated from leech (Qasim M. A. et al., Biochemistry 36:1598-1607, 1997);

(8) HCV helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) HCV polymerase inhibitors such as nucleotide analogues, gliotoxin (Ferrari R. et al. Journal of Virology 73:1649-1654, 1999), and the natural product cerulenin (Lohmann V. et al., Virology 249:108-118, 1998);

(10) Antisense phosphorothioate oligodeoxynucleotides (S-ODN) complementary to sequence stretches in the 5' non-coding region (NCR) of the HCV (Alt M. et al., Hepatology 22:707-717, 1995), or nucleotides 326-348 comprising the 3' end of the NCR and nucleotides 371-388 located in the core coding region of the IICV RNA (Alt M. et al., Archives of Virology 142:589-599, 1997; Galderisi U. et al., Journal of Cellular Physiology 181:251-257, 1999);

(11) Inhibitors of IRES-dependent translation (Ikeda N et al., Agent for the prevention and treatment of hepatitis C, Japanese Patent Publication JP-08268890; Kai Y. et al. Prevention and treatment of viral diseases, Japanese Patent Publication JP-10101591);

(12) Nuclease-resistant ribozymes. (Maccjak D. J. et al., Hepatology 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

V. Pharmaceutical Compositions

Hosts, including humans, infected with HCV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for HCV will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI. Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside. The following non-limiting embodiments illustrate some general methodology to obtain the nucleosides of the present invention.

A. General Synthesis of 1'-C-Branched Nucleosides

1'-C-Branched ribonucleosides of the following structure:

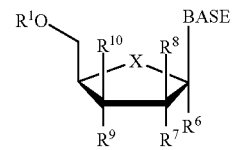

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH (lower alkyl), —NH(acyl), —N(lower alkyl)$_2$, —N(acyl)$_2$; $R^8$ and $R^{10}$ are independently H, alkyl (including lower alkyl), chlorine, bromine or iodine;

alternatively, $R^7$ and $R^9$, $R^7$ and $R^{1'}$, $R^8$ and $R^9$, or $R^8$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is an alkyl, chloro-, bromo-, fluoro-, or iodo-alkyl (i.e. $CF_3$), alkenyl, or alkynyl (i.e. allyl); and X is O, S, $SO_2$ or $CH_2$ can be prepared by one of the following general methods.

1) Modification from the Lactone

The key starting material for this process is an appropriately substituted lactone. The lactone can be purchased or can be prepared by any known means including standard epimerization, substitution and cyclization techniques. The lactone can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991. The protected lactone can then be coupled with a suitable coupling agent, such as an organometallic carbon nucleophile, such as a Grignard reagent, an organolithium, lithium dialkylcopper or $R^6$—$SiMe_3$ in TBAF with the appropriate non-protic solvent at a suitable temperature, to give the 1'-alkylated sugar.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 1'-C-branched ribonucleoside is desired. The synthesis of a ribonucleoside is shown in Scheme 1. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction: i.e. via the Barton reduction.

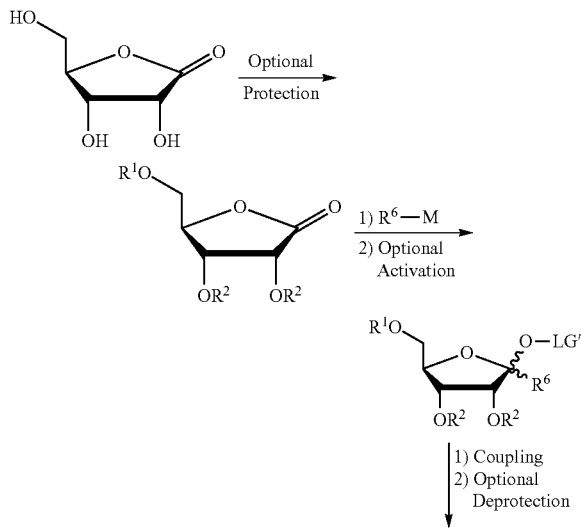

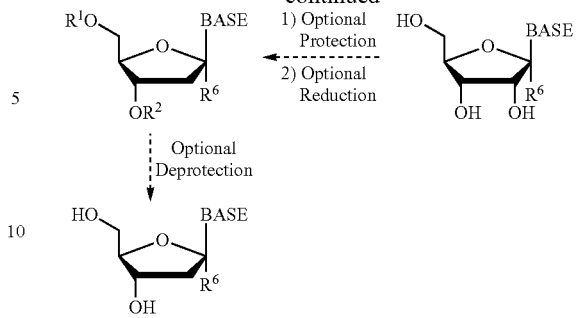

2. Alternative Method for the Preparation of 1'-C-Branched Nucleosides

The key starting material for this process is an appropriately substituted hexose. The hexose can be purchased or can be prepared by any known means including standard epimerization, such as alkaline treatment, substitution and coupling techniques. The hexose can be selectively protected to give the appropriate hexa-furanose, as taught by Townsend *Chemistry of Nucleosides and Nucleotides*, Plenum Press, 1994.

The 1'-hydroxyl can be optionally activated to a suitable leaving group such as an acyl group or a chloro, bromo, fluoro, iodo via acylation or halogenation, respectively. The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

The 1'-$CH_2$—OH, if protected, can be selectively deprotected by methods well known in the art. The resultant primary hydroxyl can be functionalized to yield various C-branched nucleosides. For example, the primary hydroxyl can be reduced to give the methyl, using a suitable reducing agent. Alternatively, the hydroxyl can be activated prior to reduction to facilitate the reaction; i.e. via the Barton reduction. In an alternate embodiment, the primary hydroxyl can be oxidized to the aldehyde, then coupled with a carbon nucleophile, such as a Grignard reagent, an organolithium, lithium dialkylcopper or $R^6$—$SiMe_3$ in TBAF with the appropriate non-protic solvent at a suitable temperature.

In a particular embodiment, the 1'-C-branched ribonucleoside is desired. The synthesis of a ribonucleoside is shown in Scheme 2. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In addition, the L-enantiomers corresponding to the compounds of the invention can be prepared following the same general methods (1 or 2), beginning with the corresponding L-sugar or nucleoside L-enantiomer as starting material.

Scheme 2

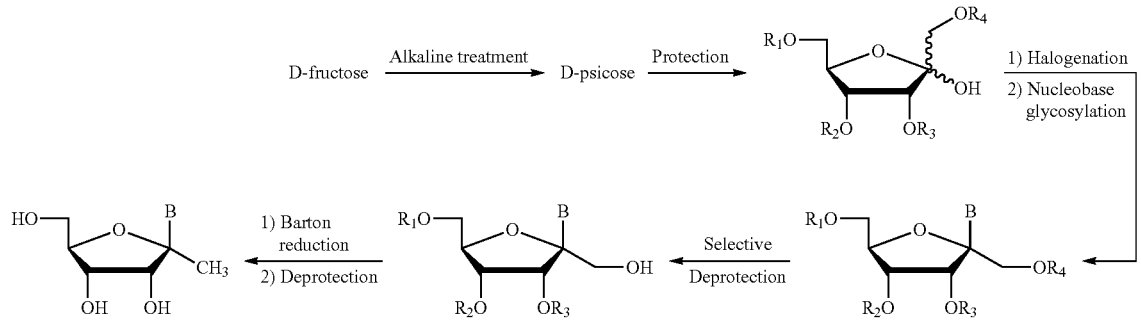

B. General Synthesis of 2'-C-Branched Nucleosides

2'-C-Branched ribonucleosides of the following structure:

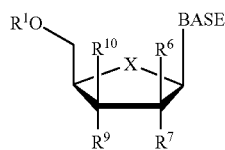

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^{10}$ is H, alkyl (including lower alkyl), chlorine, bromine or iodine;

alternatively, $R^7$ and $R^9$, or $R^7$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is an alkyl, chloro-, bromo-, fluoro-, iodo-alkyl (i.e. $CF_3$), alkenyl, or alkynyl (i.e. allyl); and X is O, S, $SO_2$ or $CH_2$ can be prepared by one of the following general methods.

1. Glycosylation of the Nucleobase with an Appropriately Modified Sugar

The key starting material for this process is an appropriately substituted sugar with a 2'-OH and 2'-H, with the appropriate leaving group (LG), for example an acyl group or a chloro, bromo, fluoro or iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 3. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 3

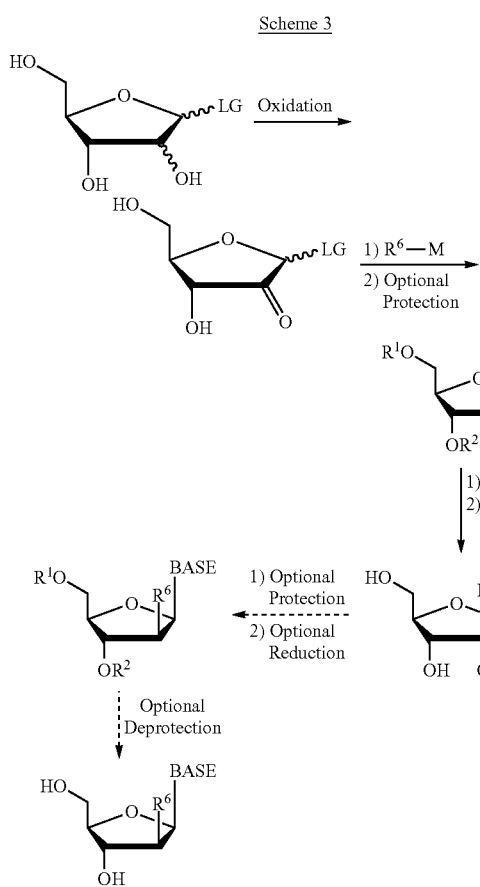

2. Modification of a Pre-Formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by GreeneGreene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

Scheme 4

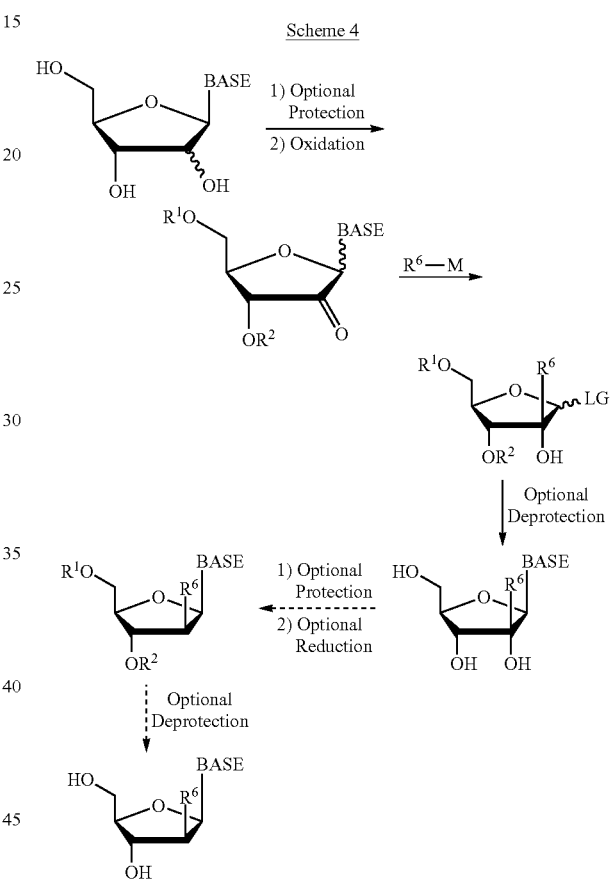

C. General Synthesis of 3'-C-Branched Nucleosides

3'-C-Branched ribonucleosides of the following structure:

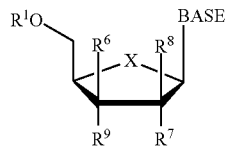

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH (lower alkyl), —NH(acyl), —N(lower alkyl)$_2$, —N(acyl)$_2$;

R⁸ is H, alkyl (including lower alkyl), chlorine, bromine or iodine;

alternatively, R⁷ and R⁹, or R⁸ and R⁹ can come together to form a pi bond;

R¹ and R² are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ or R² is independently H or phosphate;

R⁶ is an alkyl, chloro-, fluoro-, bromo-, iodo-alkyl (i.e. CF₃), alkenyl, or alkynyl (i.e. allyl); and X is O, S, SO₂ or CH₂ can be prepared by one of the following general methods.

1. Glycosylation of the Nucleobase with an Appropriately Modified Sugar

The key starting material for this process is an appropriately substituted sugar with a 3'-OH and 3'-H, with the appropriate leaving group (LG), for example an acyl group or a chloro, bromo, fluoro, iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 3'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO₂, ruthenium tetroxide, phase transfer catalysts such as chromic acid or permanganate supported on a polymer, Cl₂-pyridine, H₂O₂-ammonium molybdate, NaBrO₂—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or R⁶—SiMe₃ in TBAF with the ketone with the appropriate non-protic solvent at a suitable temperature, yields the 3'-C-branched sugar. The 3'-C-branched sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 5. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

2. Modification of a Pre-Formed Nucleoside

The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO₂, ruthenium tetroxide, phase transfer catalysts such as chromic acid or permanganate supported on a polymer, Cl₂-pyridine, H₂O₂-ammonium molybdate, NaBrO₂—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

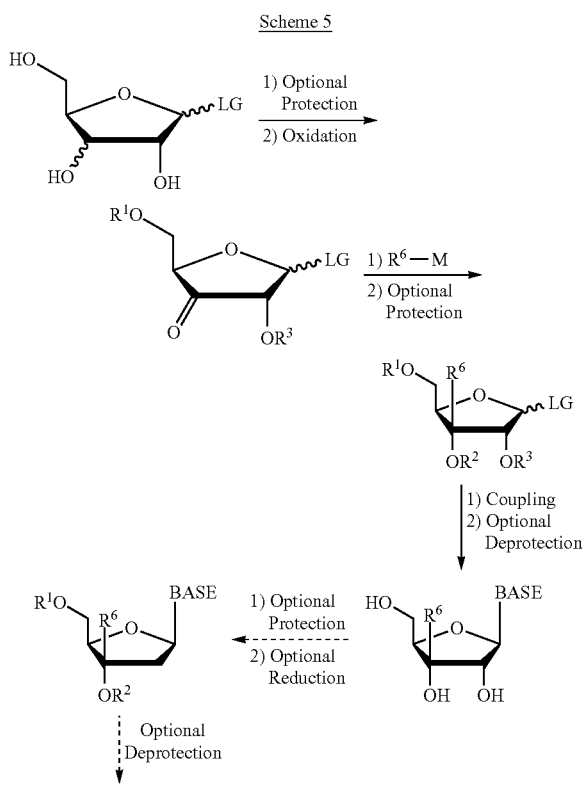

Scheme 5

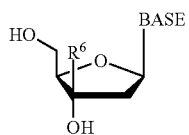

Subsequently, the nucleoside can be deprotected by methods well known to those skilled in the art, as taught by GreeneGreene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 6. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

Scheme 6

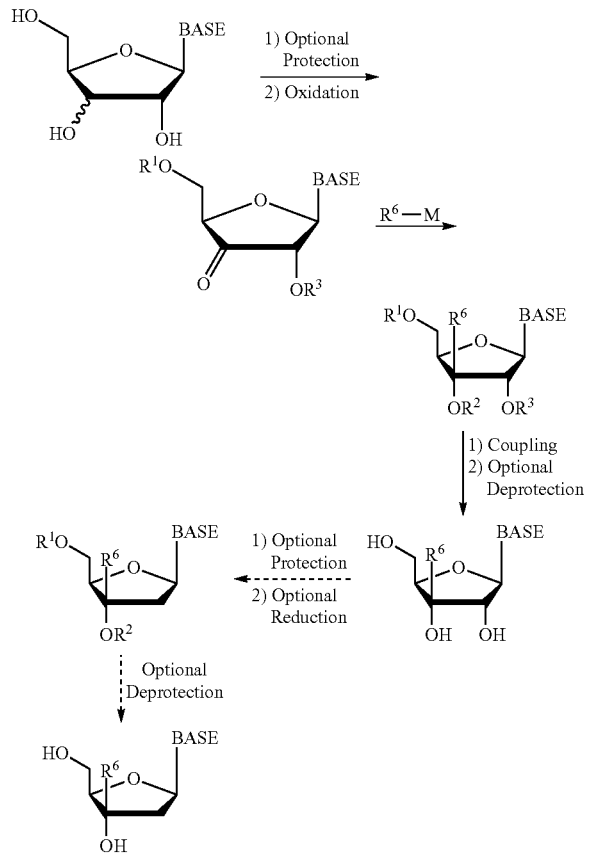

EXAMPLES

Example 1: Preparation of 1'-C-methylriboadenine via 6-amino-9-(1-deoxy-β-D-psicofuranosyl)purine As another alternative method of preparation, the title compound could also be prepared according to a published procedure (J. Farkas, and F. Sorm, "Nucleic acid components and their analogues. XCIV. Synthesis of 6-amino-9-(1-deoxy-3-D-psicofuranosyl)purine", *Collect. Czech. Chem. Commun.* 1967, 32, 2663-2667. J. Farkas", *Collect. Czech. Chem. Commun.* 1966, 31, 1535) (Scheme 7).

Scheme 7

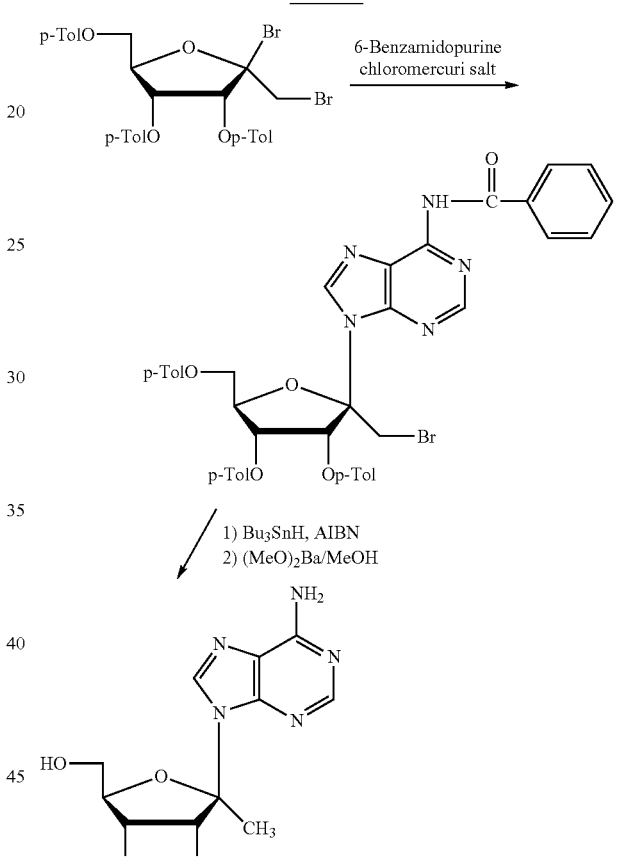

In a similar manner, but using the appropriate sugar and pyrimidine or purine bases, the following nucleosides of Formula I are prepared.

(I)

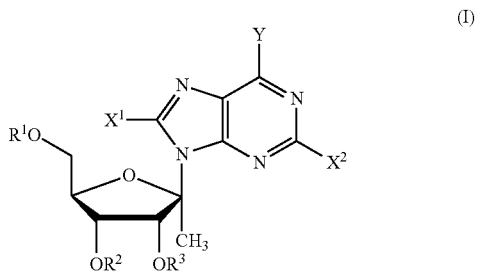

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |

-continued

| R¹ | R² | R³ | X¹ | X² | Y |
|---|---|---|---|---|---|
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | $NH_2$ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | $NH_2$ |
| H | H | H | F | H | NH-cyclopropyl |
| H | H | H | F | H | OH |
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |
| H | H | H | Br | H | F |
| H | H | H | Br | H | Cl |
| H | H | H | $NH_2$ | H | $NH_2$ |
| H | H | H | $NH_2$ | H | NH-cyclopropyl |
| H | H | H | $NH_2$ | H | OH |
| H | H | H | $NH_2$ | H | F |
| H | H | H | $NH_2$ | H | Cl |
| H | H | H | SH | H | $NH_2$ |
| H | H | H | SH | H | NH-cyclopropyl |
| H | H | H | SH | H | OH |
| H | H | H | SH | H | F |
| H | H | H | SH | H | Cl |
| acetyl | H | H | H | H | $NH_2$ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | $NH_2$ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | $NH_2$ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | $NH_2$ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | $NH_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | $NH_2$ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | $NH_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | $NH_2$ | H |
| H | H | H | H | $NH_2$ | $NH_2$ |
| H | H | H | H | $NH_2$ | NH-cyclopropyl |
| H | H | H | H | $NH_2$ | NH-methyl |
| H | H | H | H | $NH_2$ | NH-ethyl |
| H | H | H | H | $NH_2$ | NH-acetyl |
| H | H | H | H | $NH_2$ | OH |
| H | H | H | H | $NH_2$ | OMe |

-continued

| R¹ | R² | R³ | X¹ | X² | Y |
|---|---|---|---|---|---|
| H | H | H | H | NH₂ | OEt |
| H | H | H | H | NH₂ | O-cyclopropyl |
| H | H | H | H | NH₂ | O-acetyl |
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |

-continued

| R¹ | R² | R³ | X¹ | X² | Y |
|---|---|---|---|---|---|
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |

-continued

| R¹ | R² | R³ | X¹ | X² | Y |
|---|---|---|---|---|---|
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | NH₂ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | NH₂ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | NH₂ |
| triphosphate | triphosphate | triphosphate | H | Cl | NH-cyclopropyl |
| triphosphate | triphosphate | triphosphate | H | Cl | OH |
| H | H | H | F | Cl | NH₂ |
| H | H | H | F | Cl | NH-cyclopropyl |
| H | H | H | F | Cl | OH |
| H | H | H | Cl | Cl | NH₂ |
| H | H | H | Cl | Cl | NH-cyclopropyl |
| H | H | H | Cl | Cl | OH |
| H | H | H | Br | Cl | NH₂ |
| H | H | H | Br | Cl | NH-cyclopropyl |
| H | H | H | Br | Cl | OH |
| H | H | H | NH₂ | Cl | NH₂ |
| H | H | H | NH₂ | Cl | NH-cyclopropyl |
| H | H | H | NH₂ | Cl | OH |
| H | H | H | SH | Cl | NH₂ |
| H | H | H | SH | Cl | NH-cyclopropyl |
| H | H | H | SH | Cl | OH |
| acetyl | H | H | H | Cl | NH₂ |
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |

| R¹ | R² | R³ | X¹ | X² | Y |
|---|---|---|---|---|---|
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula IV are prepared, using the appropriate sugar and pyrimidine or purine bases.

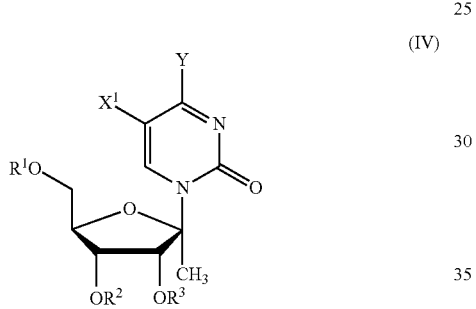

(IV)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |

| R¹ | R² | R³ | X¹ | Y |
|---|---|---|---|---|
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | $NH_2$ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | $NH_2$ |
| monophosphate | monophosphate | monophosphate | H | NH-cyclopropyl |
| monophosphate | monophosphate | monophosphate | H | OH |
| diphosphate | diphosphate | diphosphate | H | $NH_2$ |
| diphosphate | diphosphate | diphosphate | H | NH-cyclopropyl |
| diphosphate | diphosphate | diphosphate | H | OH |
| triphosphate | triphosphate | triphosphate | H | $NH_2$ |
| triphosphate | triphosphate | triphosphate | H | NH-cyclopropyl |
| triphosphate | triphosphate | triphosphate | H | OH |
| H | H | H | F | $NH_2$ |
| H | H | H | F | NH-cyclopropyl |
| H | H | H | F | OH |
| H | H | H | Cl | $NH_2$ |
| H | H | H | Cl | NH-cyclopropyl |
| H | H | H | Cl | OH |
| H | H | H | Br | $NH_2$ |
| H | H | H | Br | NH-cyclopropyl |
| H | H | H | Br | OH |
| H | H | H | $NH_2$ | $NH_2$ |
| H | H | H | $NH_2$ | NH-cyclopropyl |
| H | H | H | $NH_2$ | OH |
| H | H | H | SH | $NH_2$ |
| H | H | H | SH | NH-cyclopropyl |
| H | H | H | SH | OH |
| acetyl | H | H | H | $NH_2$ |
| acetyl | H | H | H | NH-cyclopropyl |
| acetyl | H | H | H | OH |
| acetyl | H | H | F | $NH_2$ |
| acetyl | H | H | F | NH-cyclopropyl |
| acetyl | H | H | F | OH |
| H | acetyl | acetyl | H | $NH_2$ |
| H | acetyl | acetyl | H | NH-cyclopropyl |
| H | acetyl | acetyl | H | OH |
| acetyl | acetyl | acetyl | H | $NH_2$ |
| acetyl | acetyl | acetyl | H | NH-cyclopropyl |
| acetyl | acetyl | acetyl | H | OH |
| monophosphate | acetyl | acetyl | H | $NH_2$ |
| monophosphate | acetyl | acetyl | H | NH-cyclopropyl |
| monophosphate | acetyl | acetyl | H | OH |
| diphosphate | acetyl | acetyl | H | $NH_2$ |
| diphosphate | acetyl | acetyl | H | NH-cyclopropyl |
| diphosphate | acetyl | acetyl | H | OH |
| triphosphate | acetyl | acetyl | H | $NH_2$ |
| triphosphate | acetyl | acetyl | H | NH-cyclopropyl |
| triphosphate | acetyl | acetyl | H | OH |

Alternatively, the following nucleosides of Formula VII are prepared, using the appropriate sugar and pyrimidine or purine bases.

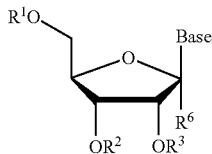

(VII)

5 wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |

-continued

| R¹ | R² | R³ | R⁶ | X | Base |
|---|---|---|---|---|---|
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |

-continued

| R¹ | R² | R³ | R⁶ | X | Base |
|---|---|---|---|---|---|
| H | H | H | $CH_3$ | S | 6-O-acetyl guanine |
| H | H | H | $CH_3$ | S | 8-fluoroguanine |
| H | H | H | $CH_3$ | S | guanine |
| H | H | H | $CH_3$ | S | 6-(N,N-diacetyl)-adenine |
| H | H | H | $CH_3$ | S | 2-fluoroadenine |
| H | H | H | $CH_3$ | S | 8-fluoroadenine |
| H | H | H | $CH_3$ | S | 2,8-difluoro-adenine |
| H | H | H | $CH_3$ | S | adenine |
| monophosphate | H | H | $CH_3$ | O | 2-(N,N-diacetyl)-guanine |
| monophosphate | H | H | $CH_3$ | O | 6-O-acetyl guanine |
| monophosphate | H | H | $CH_3$ | O | 8-fluoroguanine |
| monophosphate | H | H | $CH_3$ | O | guanine |
| monophosphate | H | H | $CH_3$ | O | 6-(N,N-diacetyl)-adenine |
| monophosphate | H | H | $CH_3$ | O | 2-fluoroadenine |
| monophosphate | H | H | $CH_3$ | O | 8-fluoroadenine |
| monophosphate | H | H | $CH_3$ | O | 2,8-difluoro-adenine |
| monophosphate | H | H | $CH_3$ | O | adenine |
| monophosphate | H | H | $CH_3$ | S | 2-(N,N-diacetyl)-guanine |
| monophosphate | H | H | $CH_3$ | S | 6-O-acetyl guanine |
| monophosphate | H | H | $CH_3$ | S | 8-fluoroguanine |
| monophosphate | H | H | $CH_3$ | S | guanine |
| monophosphate | H | H | $CH_3$ | S | 6-(N,N-diacetyl)-adenine |
| monophosphate | H | H | $CH_3$ | S | 2-fluoroadenine |
| monophosphate | H | H | $CH_3$ | S | 8-fluoroadenine |
| monophosphate | H | H | $CH_3$ | S | 2,8-difluoro-adenine |
| monophosphate | H | H | $CH_3$ | S | adenine |
| diphosphate | H | H | $CH_3$ | O | 2-(N,N-diacetyl)-guanine |
| diphosphate | H | H | $CH_3$ | O | 6-O-acetyl guanine |
| diphosphate | H | H | $CH_3$ | O | 8-fluoroguanine |
| diphosphate | H | H | $CH_3$ | O | guanine |
| diphosphate | H | H | $CH_3$ | O | 6-(N,N-diacetyl)-adenine |
| diphosphate | H | H | $CH_3$ | O | 2-fluoroadenine |
| diphosphate | H | H | $CH_3$ | O | 8-fluoroadenine |
| diphosphate | H | H | $CH_3$ | O | 2,8-difluoro-adenine |
| diphosphate | H | H | $CH_3$ | O | adenine |
| diphosphate | H | H | $CH_3$ | S | 2-(N,N-diacetyl)-guanine |
| diphosphate | H | H | $CH_3$ | S | 6-O-acetyl guanine |
| diphosphate | H | H | $CH_3$ | S | 8-fluoroguanine |
| diphosphate | H | H | $CH_3$ | S | guanine |
| diphosphate | H | H | $CH_3$ | S | 6-(N,N-diacetyl)-adenine |
| diphosphate | H | H | $CH_3$ | S | 2-fluoroadenine |
| diphosphate | H | H | $CH_3$ | S | 8-fluoroadenine |
| diphosphate | H | H | $CH_3$ | S | 2,8-difluoro-adenine |
| diphosphate | H | H | $CH_3$ | S | adenine |
| triphosphate | H | H | $CH_3$ | O | 2-(N,N-diacetyl)-guanine |
| triphosphate | H | H | $CH_3$ | O | 6-O-acetyl guanine |
| triphosphate | H | H | $CH_3$ | O | 8-fluoroguanine |
| triphosphate | H | H | $CH_3$ | O | guanine |
| triphosphate | H | H | $CH_3$ | O | 6-(N,N-diacetyl)-adenine |
| triphosphate | H | H | $CH_3$ | O | 2-fluoroadenine |
| triphosphate | H | H | $CH_3$ | O | 8-fluoroadenine |
| triphosphate | H | H | $CH_3$ | O | 2,8-difluoro-adenine |
| triphosphate | H | H | $CH_3$ | O | 2-(N,N-diacetyl)-guanine |

-continued

| R¹ | R² | R³ | R⁶ | X | Base |
|---|---|---|---|---|---|
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoro-adenine |
| monophosphate | monophosphate | monophosphate | CF₃ | O | adenine |
| monophosphate | monophosphate | monophosphate | CF₃ | S | 2-(N,N-diacetyl)-guanine |
| monophosphate | monophosphate | monophosphate | CF₃ | S | 6-O-acetyl guanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)-adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoro-adenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula VIII are prepared, using the appropriate sugar and pyrimidine or purine bases.

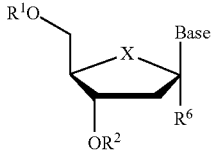

(VIII)

wherein

| R¹ | R² | R⁶ | X | Base |
|---|---|---|---|---|
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosine |
| H | H | CH₃ | S | 4-(N,N-diacetyl)cytosine |
| H | H | CH₃ | S | Uracil |
| H | H | CH₃ | S | 5-Fluorouracil |
| monophosphate | H | CH₃ | O | 2,4-O-Diacetyluracil |
| monophosphate | H | CH₃ | O | Hypoxanthine |
| monophosphate | H | CH₃ | O | 2,4-O-Diacetylthymine |
| monophosphate | H | CH₃ | O | Thymine |
| monophosphate | H | CH₃ | O | Cytosine |
| monophosphate | H | CH₃ | O | 4-(N-mono-acetyl)cytosine |

| R¹ | R² | R⁶ | X | Base |
|---|---|---|---|---|
| monophosphate | H | CH₃ | O | 4-(N,N-diacetyl)cytosine |
| monophosphate | H | CH₃ | O | Uracil |
| monophosphate | H | CH₃ | O | 5-Fluorouracil |
| monophosphate | H | CH₃ | S | 2,4-O-Diacetyluracil |
| monophosphate | H | CH₃ | S | Hypoxanthine |
| monophosphate | H | CH₃ | S | 2,4-O-Diacetylthymine |
| monophosphate | H | CH₃ | S | Thymine |
| monophosphate | H | CH₃ | S | Cytosine |
| monophosphate | H | CH₃ | S | 4-(N-monoacetyl)cytosine |
| monophosphate | H | CH₃ | S | 4-(N,N-diacetyl)cytosine |
| monophosphate | H | CH₃ | S | Uracil |
| monophosphate | H | CH₃ | S | 5-Fluorouracil |
| diphosphate | H | CH₃ | O | 2,4-O-Diacetyluracil |
| diphosphate | H | CH₃ | O | Hypoxanthine |
| diphosphate | H | CH₃ | O | 2,4-O-Diacetylthymine |
| diphosphate | H | CH₃ | O | Thymine |
| diphosphate | H | CH₃ | O | Cytosine |
| diphosphate | H | CH₃ | O | 4-(N-monoacetyl)cytosine |
| diphosphate | H | CH₃ | O | 4-(N,N-diacetyl)cytosine |
| diphosphate | H | CH₃ | O | Uracil |
| diphosphate | H | CH₃ | O | 5-Fluorouracil |
| diphosphate | H | CH₃ | S | 2,4-O-Diacetyluracil |
| diphosphate | H | CH₃ | S | Hypoxanthine |
| diphosphate | H | CH₃ | S | 2,4-O-Diacetylthym |
| diphosphate | H | CH₃ | S | Thymine |
| diphosphate | H | CH₃ | S | Cytosine |
| diphosphate | H | CH₃ | S | 4-(n-monoacetyl)cytosine |
| diphosphate | H | CH₃ | S | 4-(N,N-diacetyl)cytosine |
| diphosphate | H | CH₃ | S | Uracil |
| diphosphate | H | CH₃ | S | 5-Fluorouracil |
| triphosphate | H | CH₃ | O | 2,4-O-Diacetyluracil |
| triphosphate | H | CH₃ | O | Hypoxanthine |
| triphosphate | H | CH₃ | O | 2,4-O-diacetylthymine |
| triphosphate | H | CH₃ | O | Thymine |
| triphosphate | H | CH₃ | O | Cytosine |
| triphosphate | H | CH₃ | O | 4-(N-monoacetyl)cytosine |
| triphosphate | H | CH₃ | O | 4-(N,N-diacetyl)cytosine |
| triphosphate | H | CH₃ | O | Uracil |
| triphosphate | H | CH₃ | O | 5-Fluorouracil |
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| triphosphate | H | CH₃ | S | 4-(n-monoacetyl)cytosine |
| triphosphate | H | CH₃ | S | 4-(N,N-diacetyl)cytosine |
| triphosphate | H | CH₃ | S | Uracil |
| triphosphate | H | CH₃ | S | 5-Fluorouracil |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-monoacetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-monoacetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |
| H | H | CH₃ | O | 2-(N,N-diacetyl)-guanine |
| H | H | CH₃ | O | 6-O-acetyl guanine |
| H | H | CH₃ | O | 8-fluoroguanine |
| H | H | CH₃ | O | guanine |
| H | H | CH₃ | O | 6-(N,N-diacetyl)-adenine |
| H | H | CH₃ | O | 2-fluoroadenine |
| H | H | CH₃ | O | 8-fluoroadenine |
| H | H | CH₃ | O | 2,8-difluoro-adenine |
| H | H | CH₃ | O | adenine |
| H | H | CH₃ | S | 2-(N,N-diacetyl)-guanine |
| H | H | CH₃ | S | 6-O-acetyl guanine |
| H | H | CH₃ | S | 8-fluoroguanine |
| H | H | CH₃ | S | guanine |
| H | H | CH₃ | S | 6-(N,N-diacetyl)-adenine |
| H | H | CH₃ | S | 2-fluoroadenine |
| H | H | CH₃ | S | 8-fluoroadenine |
| H | H | CH₃ | S | 2,8-difluoro-adenine |
| H | H | CH₃ | S | adenine |
| monophosphate | H | CH₃ | O | 2-(N,N-diacetyl)-guanine |
| monophosphate | H | CH₃ | O | 6-O-acetyl guanine |
| monophosphate | H | CH₃ | O | 8-fluoroguanine |
| monophosphate | H | CH₃ | O | guanine |
| monophosphate | H | CH₃ | O | 6-(N,N-diacetyl)-adenine |
| monophosphate | H | CH₃ | O | 2-fluoroadenine |
| monophosphate | H | CH₃ | O | 8-fluoroadenine |
| monophosphate | H | CH₃ | O | 2,8-difluoro-adenine |
| monophosphate | H | CH₃ | O | adenine |
| monophosphate | H | CH₃ | S | 2-(N,N-diacetyl)-guanine |
| monophosphate | H | CH₃ | S | 6-O-acetyl guanine |
| monophosphate | H | CH₃ | S | 8-fluoroguanine |
| monophosphate | H | CH₃ | S | guanine |
| monophosphate | H | CH₃ | S | 6-(N,N-diacetyl)-adenine |
| monophosphate | H | CH₃ | S | 2-fluoroadenine |
| monophosphate | H | CH₃ | S | 8-fluoroadenine |
| monophosphate | H | CH₃ | S | 2,8-difluoro-adenine |

-continued

| R¹ | R² | R⁶ | X | Base |
|---|---|---|---|---|
| monophosphate | H | CH₃ | S | adenine |
| diphosphate | H | CH₃ | O | 2-(N,N-diacetyl)-guanine |
| diphosphate | H | CH₃ | O | 6-O-acetyl guanine |
| diphosphate | H | CH₃ | O | 8-fluoroguanine |
| diphosphate | H | CH₃ | O | guanine |
| diphosphate | H | CH₃ | O | 6-(N,N-diacetyl)-adenine |
| diphosphate | H | CH₃ | O | 2-fluoroadenine |
| diphosphate | H | CH₃ | O | 8-fluoroadenine |
| diphosphate | H | CH₃ | O | 2,8-difluoro-adenine |
| diphosphate | H | CH₃ | O | adenine |
| diphosphate | H | CH₃ | S | 2-(N,N-diacetyl)-guanine |
| diphosphate | H | CH₃ | S | 6-O-acetyl guanine |
| diphosphate | H | CH₃ | S | 8-fluoroguanine |
| diphosphate | H | CH₃ | S | guanine |
| diphosphate | H | CH₃ | S | 6-(N,N-diacetyl)-adenine |
| diphosphate | H | CH₃ | S | 2-fluoroadenine |
| diphosphate | H | CH₃ | S | 8-fluoroadenine |
| diphosphate | H | CH₃ | S | 2,8-difluoro-adenine |
| diphosphate | H | CH₃ | S | adenine |
| triphosphate | H | CH₃ | O | 2-(N,N-diacetyl)-guanine |
| triphosphate | H | CH₃ | O | 6-O-acetyl guanine |
| triphosphate | H | CH₃ | O | 8-fluoroguanine |
| triphosphate | H | CH₃ | O | guanine |
| triphosphate | H | CH₃ | O | 6-(N,N-diacetyl)-adenine |
| triphosphate | H | CH₃ | O | 2-fluoroadenine |
| triphosphate | H | CH₃ | O | 8-fluoroadenine |
| triphosphate | H | CH₃ | O | 2,8-difluoro-adenine |
| triphosphate | H | CH₃ | S | 2-(N,N-diacetyl)-guanine |
| triphosphate | H | CH₃ | S | 6-O-acetyl guanine |
| triphosphate | H | CH₃ | S | 8-fluoroguanine |
| triphosphate | H | CH₃ | S | guanine |
| triphosphate | H | CH₃ | S | 6-(N,N-diacetyl)-adenine |
| triphosphate | H | CH₃ | S | 2-fluoroadenine |
| triphosphate | H | CH₃ | S | 8-fluoroadenine |
| triphosphate | H | CH₃ | S | 2,8-difluoro-adenine |
| triphosphate | H | CH₃ | S | adenine |
| monophosphate | monophosphate | CF₃ | O | 2-(N,N-diacetyl)-guanine |
| monophosphate | monophosphate | CF₃ | O | 6-O-acetyl guanine |
| monophosphate | monophosphate | CF₃ | O | 8-fluoroguanine |
| monophosphate | monophosphate | CF₃ | O | guanine |
| monophosphate | monophosphate | CF₃ | O | 6-(N,N-diacetyl)-adenine |
| monophosphate | monophosphate | CF₃ | O | 2-fluoroadenine |
| monophosphate | monophosphate | CF₃ | O | 8-fluoroadenine |
| monophosphate | monophosphate | CF₃ | O | 2,8-difluoro-adenine |
| monophosphate | monophosphate | CF₃ | O | adenine |
| monophosphate | monophosphate | CF₃ | S | 2-(N,N-diacetyl)-guanine |
| monophosphate | monophosphate | CF₃ | S | 6-O-acetyl guanine |
| monophosphate | monophosphate | CF₃ | S | 8-fluoroguanine |
| monophosphate | monophosphate | CF₃ | S | guanine |
| monophosphate | monophosphate | CF₃ | S | 6-(N,N-diacetyl)-adenine |
| monophosphate | monophosphate | CF₃ | S | 2-fluoroadenine |
| monophosphate | monophosphate | CF₃ | S | 8-fluoroadenine |
| monophosphate | monophosphate | CF₃ | S | 2,8-difluoro-adenine |

-continued

| R¹ | R² | R⁶ | X | Base |
|---|---|---|---|---|
| monophosphate | monophosphate | CF₃ | S | adenine |
| acetyl | acetyl | CF₃ | O | guanine |
| acetyl | acetyl | CF₃ | S | guanine |
| acetyl | acetyl | 2-bromo-vinyl | O | guanine |
| acetyl | acetyl | 2-bromo-vinyl | S | guanine |

Alternatively, the following nucleosides of Formula IX are prepared, using the appropriate sugar and pyrimidine or purine bases.

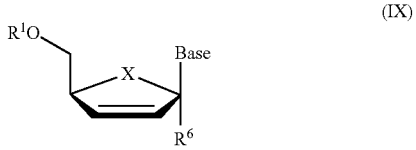

(IX)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytos |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |

-continued

| R¹ | R⁶ | X | Base |
|---|---|---|---|
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphospahate | CH₃ | S | 2,4-O-Diacetylthymine |
| triphospahate | CH₃ | S | Thymine |
| triphospahate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytos |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVI are prepared, using the appropriate sugar and pyrimidine or purine bases.

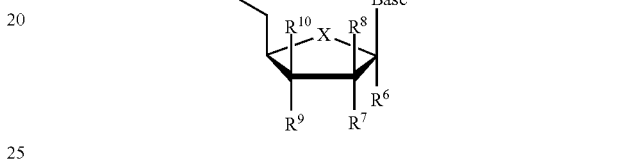

(XVI)

wherein:

| R¹ | R⁶ | R⁷ | R⁸ | X | Base | R¹⁰ | R⁹ |
|---|---|---|---|---|---|---|---|
| H | CH₃ | H | H | O | 2,4-O-Diacetyluracil | OH | Me |
| H | CH₃ | H | H | O | Hypoxanthine | OH | Me |
| H | CH₃ | H | H | O | 2,4-O-Diacetylthymine | OH | Me |
| H | CH₃ | H | H | O | Thymine | OH | Me |
| H | CH₃ | H | H | O | Cytosine | OH | Me |
| H | CH₃ | H | H | O | 4-(N-mono-acetyl)cytosine | OH | Me |
| H | CH₃ | H | H | O | 4-(N,N-diacetyl)cytosine | OH | Me |
| H | CH₃ | H | H | O | Uracil | OH | Me |
| H | CH₃ | H | H | O | 5-Fluorouracil | OH | Me |
| H | CH₃ | H | H | S | 2,4-O-Diacetyluracil | OH | Me |
| H | CH₃ | H | H | S | Hypoxanthine | OH | Me |
| H | CH₃ | H | H | S | 2,4-O-Diacetylthymine | OH | Me |
| H | CH₃ | H | H | S | Thymine | OH | Me |
| H | CH₃ | H | H | S | Cytosine | OH | Me |
| H | CH₃ | H | H | S | 4-(N-mono-acetyl)cytosine | OH | Me |
| H | CH₃ | H | H | S | 4-(N,N-diacetyl)cytosine | OH | Me |
| H | CH₃ | H | H | S | Uracil | OH | Me |
| H | CH₃ | H | H | S | 5-Fluorouracil | OH | Me |
| monophosphate | CH₃ | H | H | O | 2,4-O-Diacetyluracil | OH | Me |
| monophosphate | CH₃ | H | H | O | Hypoxanthine | OH | Me |
| monophosphate | CH₃ | H | H | O | 2,4-O-Diacetylthymine | OH | Me |
| monophosphate | CH₃ | H | H | O | Thymine | OH | Me |
| monophosphate | CH₃ | H | H | O | Cytosine | OH | Me |
| monophosphate | CH₃ | H | H | O | 4-(N-mono-acetyl)cytosine | OH | Me |
| monophosphate | CH₃ | H | H | O | 4-(N,N-diacetyl)cytosine | OH | Me |
| monophosphate | CH₃ | H | H | O | Uracil | OH | Me |
| monophosphate | CH₃ | H | H | O | 5-Fluorouracil | OH | Me |
| monophosphate | CH₃ | H | H | S | 2,4-O-Diacetyluracil | OH | Me |
| monophosphate | CH₃ | H | H | S | Hypoxanthine | OH | Me |
| monophosphate | CH₃ | H | H | S | 2,4-O-Diacetylthymine | OH | Me |
| monophosphate | CH₃ | H | H | S | Thymine | OH | Me |
| monophosphate | CH₃ | H | H | S | Cytosine | OH | Me |
| monophosphate | CH₃ | H | H | S | 4-(N-mono-acetyl)cytosine | OH | Me |
| monophosphate | CH₃ | H | H | S | 4-(N,N-diacetyl)cytosine | OH | Me |
| monophosphate | CH₃ | H | H | S | Uracil | OH | Me |
| monophosphate | CH₃ | H | H | S | 5-Fluorouracil | OH | Me |
| diphosphate | CH₃ | H | H | O | 2,4-O-Diacetyluracil | OH | Me |
| diphosphate | CH₃ | H | H | O | Hypoxanthine | OH | Me |
| diphosphate | CH₃ | H | H | O | 2,4-O-Diacetylthymine | OH | Me |
| diphosphate | CH₃ | H | H | O | Thymine | OH | Me |
| diphosphate | CH₃ | H | H | O | Cytosine | OH | Me |
| diphosphate | CH₃ | H | H | O | 4-(N-mono-acetyl)cytosine | OH | Me |
| diphosphate | CH₃ | H | H | O | 4-(N,N-diacetyl)cytosine | OH | Me |
| diphosphate | CH₃ | H | H | O | Uracil | OH | Me |
| diphosphate | CH₃ | H | H | O | 5-Fluorouracil | OH | Me |

-continued

| R¹ | R⁶ | R⁷ | R⁸ | X | Base | R¹⁰ | R⁹ |
|---|---|---|---|---|---|---|---|
| diphosphate | CH₃ | H | H | S | 2,4-O-Diacetyluracil | OH | Me |
| diphosphate | CH₃ | H | H | S | Hypoxanthine | OH | Me |
| diphosphate | CH₃ | H | H | S | 2,4-O-Diacetylthymine | OH | Me |
| diphosphate | CH₃ | H | H | S | Thymine | OH | Me |
| diphosphate | CH₃ | H | H | S | Cytosine | OH | Me |
| triphosphate | CH₃ | H | H | O | 2,4-O-Diacetyluracil | OH | Me |
| triphosphate | CH₃ | H | H | O | Hypoxanthine | OH | Me |
| triphosphate | CH₃ | H | H | O | 2,4-O-Diacetylthymine | OH | Me |
| triphosphate | CH₃ | H | H | O | Thymine | OH | Me |
| triphosphate | CH₃ | H | H | O | Cytosine | OH | Me |
| triphosphate | CH₃ | H | H | O | 4-(N-mono-acetyl)cytosine | OH | Me |
| triphosphate | CH₃ | H | H | O | 4-(N,N-diacetyl)cytosine | OH | Me |
| triphosphate | CH₃ | H | H | O | Uracil | OH | Me |
| triphosphate | CH₃ | H | H | O | 5-Fluorouracil | OH | Me |
| triphosphate | CH₃ | H | H | S | 2,4-O-Diacetyluracil | OH | Me |
| triphosphate | CH₃ | H | H | S | Hypoxanthine | OH | Me |
| triphosphate | CH₃ | H | H | S | 2,4-O-Diacetylthymine | OH | Me |
| triphosphate | CH₃ | H | H | S | Thymine | OH | Me |
| triphosphate | CH₃ | H | H | S | Cytosine | OH | Me |
| monophosphate | CF₃ | H | H | O | 2,4-O-Diacetyluracil | OH | Me |
| monophosphate | CF₃ | H | H | O | Hypoxanthine | OH | Me |
| monophosphate | CF₃ | H | H | O | 2,4-O-Diacetylthymine | OH | Me |
| monophosphate | CF₃ | H | H | O | Thymine | OH | Me |
| monophosphate | CF₃ | H | H | O | Cytosine | OH | Me |
| monophosphate | CF₃ | H | H | O | 4-(N-mono-acetyl)cytosine | OH | Me |
| monophosphate | CF₃ | H | H | O | 4-(N,N-diacetyl)cytosine | OH | Me |
| monophosphate | CF₃ | H | H | O | Uracil | OH | Me |
| monophosphate | CF₃ | H | H | O | 5-Fluorouracil | OH | Me |
| monophosphate | CF₃ | H | H | S | 2,4-O-Diacetyluracil | OH | Me |
| monophosphate | CF₃ | H | H | S | Hypoxanthine | OH | Me |
| monophosphate | CF₃ | H | H | S | 2,4-O-Diacetylthymine | OH | Me |
| monophosphate | CF₃ | H | H | S | Thymine | OH | Me |
| monophosphate | CF₃ | H | H | S | Cytosine | OH | Me |
| monophosphate | CF₃ | H | H | S | 4-(N-mono-acetyl)cytosine | OH | Me |
| monophosphate | CF₃ | H | H | S | 4-(N,N-diacetyl)cytosine | OH | Me |
| monophosphate | CF₃ | H | H | S | Uracil | OH | Me |
| monophosphate | CF₃ | H | H | S | 5-Fluorouracil | OH | Me |
| acetyl | CH₃ | H | H | O | 4-(N,N-diacetyl)cytosine | H | Br |
| acetyl | CH₃ | H | H | S | 4-(N,N-diacetyl)cytosine | H | Br |
| acetyl | CH₃ | OH | H | O | 4-(N,N-diacetyl)cytosine | H | Br |
| acetyl | CH₃ | OH | H | S | 4-(N,N-diacetyl)cytosine | H | Br |

Example 2: Preparation of 2'-C-methylriboadenine

The title compound was prepared according to a published procedure (R. E. Harry-O'kuru, J. M. Smith, and M. S. Wolfe, "A short, flexible route toward 2'-C-branched ribonucleosides", *J. Org. Chem.* 1997, 62, 1754-1759) (Scheme 8).

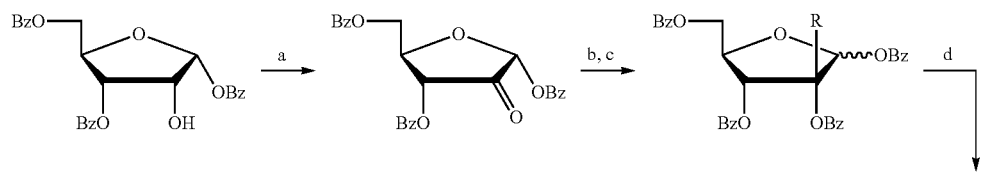

-continued

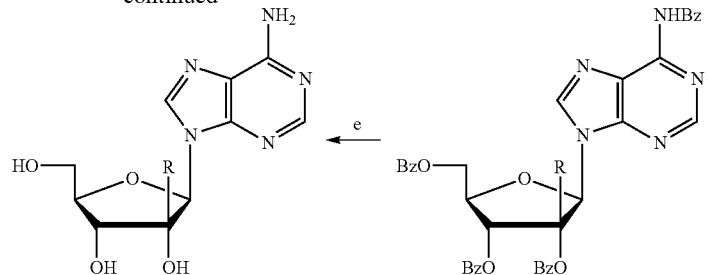

R = CH₃

(a) Dess-Martin periodinane; (b) MeMgBr/TiCl₄; (c) BzCl, DMAP, Et₃N; (d) bis(trimethylsilyl)acetamide, N⁶-benzoyl adenine, TMSOTf; (e) NH₃/MeOH In a similar manner, but using the appropriate sugar and pyrimidine or purine bases, the following nucleosides of Formula II are prepared.

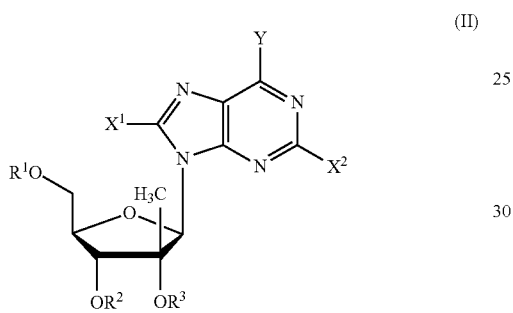

(II)

wherein:

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |

-continued

| R¹ | R² | R³ | X¹ | X² | Y |
|---|---|---|---|---|---|
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | NH₂ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | NH₂ |
| H | H | H | F | H | NH-cyclopropyl |
| H | H | H | F | H | OH |
| H | H | H | F | H | F |
| H | H | H | F | H | Cl |
| H | H | H | Cl | H | NH₂ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | NH₂ |
| H | H | H | Br | H | NH-cyclopropyl |
| H | H | H | Br | H | OH |
| H | H | H | Br | H | F |
| H | H | H | Br | H | Cl |
| H | H | H | NH₂ | H | NH₂ |
| H | H | H | NH₂ | H | NH-cyclopropyl |
| H | H | H | NH₂ | H | OH |
| H | H | H | NH₂ | H | F |
| H | H | H | NH₂ | H | Cl |
| H | H | H | SH | H | NH₂ |
| H | H | H | SH | H | NH-cyclopropyl |
| H | H | H | SH | H | OH |

-continued

| R¹ | R² | R³ | X¹ | X² | Y |
|---|---|---|---|---|---|
| H | H | H | SH | H | F |
| H | H | H | SH | H | Cl |
| acetyl | H | H | H | H | NH₂ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | NH₂ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | NH₂ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | NH₂ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | NH₂ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | NH₂ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | NH₂ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | NH₂ | H |
| H | H | H | H | NH₂ | NH₂ |
| H | H | H | H | NH₂ | NH-cyclopropyl |
| H | H | H | H | NH₂ | NH-methyl |
| H | H | H | H | NH₂ | NH-ethyl |
| H | H | H | H | NH₂ | NH-acetyl |
| H | H | H | H | NH₂ | OH |
| H | H | H | H | NH₂ | OMe |
| H | H | H | H | NH₂ | OEt |
| H | H | H | H | NH₂ | O-cyclopropyl |
| H | H | H | H | NH₂ | O-acetyl |
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |

-continued

| R¹ | R² | R³ | X¹ | X² | Y |
|---|---|---|---|---|---|
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |

-continued

| R¹ | R² | R³ | X¹ | X² | Y |
|---|---|---|---|---|---|
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |

-continued

| R¹ | R² | R³ | X¹ | X² | Y |
|---|---|---|---|---|---|
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | $NH_2$ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | $NH_2$ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | $NH_2$ |
| triphosphate | triphosphate | triphosphate | H | Cl | NH-cyclopropyl |
| triphosphate | triphosphate | triphosphate | H | Cl | OH |
| H | H | H | F | Cl | $NH_2$ |
| H | H | H | F | Cl | NH-cyclopropyl |
| H | H | H | F | Cl | OH |
| H | H | H | Cl | Cl | $NH_2$ |
| H | H | H | Cl | Cl | NH-cyclopropyl |
| H | H | H | Cl | Cl | OH |
| H | H | H | Br | Cl | $NH_2$ |
| H | H | H | Br | Cl | NH-cyclopropyl |
| H | H | H | Br | Cl | OH |
| H | H | H | $NH_2$ | Cl | $NH_2$ |
| H | H | H | $NH_2$ | Cl | NH-cyclopropyl |
| H | H | H | $NH_2$ | Cl | OH |
| H | H | H | SH | Cl | $NH_2$ |
| H | H | H | SH | Cl | NH-cyclopropyl |
| H | H | H | SH | Cl | OH |
| acetyl | H | H | H | Cl | $NH_2$ |
| acetyl | H | H | H | Cl | NH-cyclopropyl |
| acetyl | H | H | H | Cl | OH |
| acetyl | H | H | F | Cl | $NH_2$ |
| acetyl | H | H | F | Cl | NH-cyclopropyl |
| acetyl | H | H | F | Cl | OH |
| H | acetyl | acetyl | H | Cl | $NH_2$ |
| H | acetyl | acetyl | H | Cl | NH-cyclopropyl |
| H | acetyl | acetyl | H | Cl | OH |
| acetyl | acetyl | acetyl | H | Cl | $NH_2$ |
| acetyl | acetyl | acetyl | H | Cl | NH-cyclopropyl |
| acetyl | acetyl | acetyl | H | Cl | OH |
| monophosphate | acetyl | acetyl | H | Cl | $NH_2$ |
| monophosphate | acetyl | acetyl | H | Cl | NH-cyclopropyl |
| monophosphate | acetyl | acetyl | H | Cl | OH |
| diphosphate | acetyl | acetyl | H | Cl | $NH_2$ |
| diphosphate | acetyl | acetyl | H | Cl | NH-cyclopropyl |
| diphosphate | acetyl | acetyl | H | Cl | OH |
| triphosphate | acetyl | acetyl | H | Cl | $NH_2$ |
| triphosphate | acetyl | acetyl | H | Cl | NH-cyclopropyl |
| triphosphate | acetyl | acetyl | H | Cl | OH |
| H | H | H | H | Cl | $NH_2$ |
| H | H | H | H | Cl | NH-cyclopropyl |
| H | H | H | H | Cl | OH |
| H | H | H | H | Br | $NH_2$ |
| H | H | H | H | Br | NH-cyclopropyl |
| H | H | H | H | Br | OH |

Alternatively, the following nucleosides of Formula V are prepared, using the appropriate sugar and pyrimidine or purine bases.

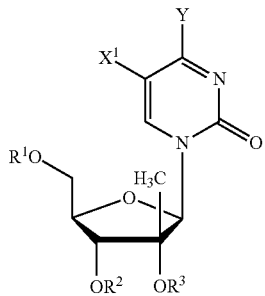

(V)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | NH₂ |
| monophosphate | monophosphate | monophosphate | H | NH-cyclopropyl |
| monophosphate | monophosphate | monophosphate | H | OH |
| diphosphate | diphosphate | diphosphate | H | NH₂ |
| diphosphate | diphosphate | diphosphate | H | NH-cyclopropyl |
| diphosphate | diphosphate | diphosphate | H | OH |
| triphosphate | triphosphate | triphosphate | H | NH₂ |
| triphosphate | triphosphate | triphosphate | H | NH-cyclopropyl |
| triphosphate | triphosphate | triphosphate | H | OH |
| H | H | H | F | NH₂ |
| H | H | H | F | NH-cyclopropyl |
| H | H | H | F | OH |
| H | H | H | Cl | NH₂ |
| H | H | H | Cl | NH-cyclopropyl |
| H | H | H | Cl | OH |
| H | H | H | Br | NH₂ |
| H | H | H | Br | NH-cyclopropyl |
| H | H | H | Br | OH |
| H | H | H | NH₂ | NH₂ |
| H | H | H | NH₂ | NH-cyclopropyl |
| H | H | H | NH₂ | OH |
| H | H | H | SH | NH₂ |
| H | H | H | SH | NH-cyclopropyl |
| H | H | H | SH | OH |
| acetyl | H | H | H | NH₂ |
| acetyl | H | H | H | NH-cyclopropyl |
| acetyl | H | H | H | OH |
| acetyl | H | H | F | NH₂ |
| acetyl | H | H | F | NH-cyclopropyl |
| acetyl | H | H | F | OH |
| H | acetyl | acetyl | H | NH₂ |
| H | acetyl | acetyl | H | NH-cyclopropyl |
| H | acetyl | acetyl | H | OH |
| acetyl | acetyl | acetyl | H | NH₂ |
| acetyl | acetyl | acetyl | H | NH-cyclopropyl |
| acetyl | acetyl | acetyl | H | OH |
| monophosphate | acetyl | acetyl | H | NH₂ |
| monophosphate | acetyl | acetyl | H | NH-cyclopropyl |
| monophosphate | acetyl | acetyl | H | OH |
| diphosphate | acetyl | acetyl | H | NH₂ |
| diphosphate | acetyl | acetyl | H | NH-cyclopropyl |
| diphosphate | acetyl | acetyl | H | OH |
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula X are prepared, using the appropriate sugar and pyrimidine or purine bases.

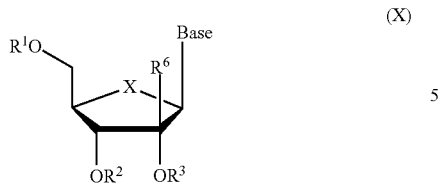 (X)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |

-continued

| R¹ | R² | R³ | R⁶ | X | Base |
|---|---|---|---|---|---|
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |

-continued

| R¹ | R² | R³ | R⁶ | X | Base |
|---|---|---|---|---|---|
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |

-continued

| R¹ | R² | R³ | R⁶ | X | Base |
|---|---|---|---|---|---|
| triphosphate | H | H | $CH_3$ | S | 2,8-difluoro-adenine |
| triphosphate | H | H | $CH_3$ | S | adenine |
| monophosphate | monophosphate | monophosphate | $CF_3$ | O | 2-(N,N-diacetyl)-guanine |
| monophosphate | monophosphate | monophosphate | $CF_3$ | O | 6-O-acetyl guanine |
| monophosphate | monophosphate | monophosphate | $CF_3$ | O | 8-fluoroguanine |
| monophosphate | monophosphate | monophosphate | $CF_3$ | O | guanine |
| monophosphate | monophosphate | monophosphate | $CF_3$ | O | 6-(N,N-diacetyl)-adenine |
| monophosphate | monophosphate | monophosphate | $CF_3$ | O | 2-fluoroadenine |
| monophosphate | monophosphate | monophosphate | $CF_3$ | O | 8-fluoroadenine |
| monophosphate | monophosphate | monophosphate | $CF_3$ | O | 2,8-difluoro-adenine |
| monophosphate | monophosphate | monophosphate | $CF_3$ | O | adenine |
| monophosphate | monophosphate | monophosphate | $CF_3$ | S | 2-(N,N-diacetyl)-guanine |
| monophosphate | monophosphate | monophosphate | $CF_3$ | S | 6-O-acetyl guanine |
| monophosphate | monophosphate | monophosphate | $CF_3$ | S | 8-fluoroguanine |
| monophosphate | monophosphate | monophosphate | $CF_3$ | S | guanine |
| monophosphate | monophosphate | monophosphate | $CF_3$ | S | 6-(N,N-diacetyl)-adenine |
| monophosphate | monophosphate | monophosphate | $CF_3$ | S | 2-fluoroadenine |
| monophosphate | monophosphate | monophosphate | $CF_3$ | S | 8-fluoroadenine |
| monophosphate | monophosphate | monophosphate | $CF_3$ | S | 2,8-difluoro-adenine |
| monophosphate | monophosphate | monophosphate | $CF_3$ | S | adenine |
| acetyl | acetyl | acetyl | $CF_3$ | O | guanine |
| acetyl | acetyl | acetyl | $CF_3$ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula XI are prepared, using the appropriate sugar and pyrimidine or purine bases.

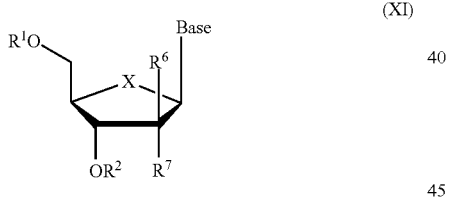

(XI)

wherein:

| R¹ | R² | R⁷ | R⁶ | X | Base |
|---|---|---|---|---|---|
| H | H | H | $CH_3$ | O | 2,4-O-Diacetyluracil |
| H | H | H | $CH_3$ | O | Hypoxanthine |
| H | H | H | $CH_3$ | O | 2,4-O-Diacetylthymine |
| H | H | H | $CH_3$ | O | Thymine |
| H | H | H | $CH_3$ | O | Cytosine |
| H | H | H | $CH_3$ | O | 4-(N-mono-acetyl)cytosine |
| H | H | H | $CH_3$ | O | 4-(N,N-diacetyl)cytosine |
| H | H | H | $CH_3$ | O | Uracil |
| H | H | H | $CH_3$ | O | 5-Fluorouracil |
| H | H | H | $CH_3$ | S | 2,4-O-Diacetyluracil |
| H | H | H | $CH_3$ | S | Hypoxanthine |
| H | H | H | $CH_3$ | S | 2,4-O-Diacetylthymine |
| H | H | H | $CH_3$ | S | Thymine |
| H | H | H | $CH_3$ | S | Cytosine |
| H | H | H | $CH_3$ | S | 4-(N-mono-acetyl)cytosin |
| H | H | H | $CH_3$ | S | 4-(N,N-diacetyl)cytosine |
| H | H | H | $CH_3$ | S | Uracil |
| H | H | H | $CH_3$ $CH_3$ | S | 5-Fluorouracil |
| monophosphate | H | H | $CH_3$ | O | 2,4-O-Diacetyluracil |

| R¹ | R² | R⁷ | R⁶ | X | Base |
|---|---|---|---|---|---|
| monophosphate | H | H | CH₃ | O | Hypoxanthine |
| monophosphate | H | H | CH₃ | O | 2,4-O-Diacetylthymine |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthymine |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetylurac |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytos |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthym |
| triphosphate | H | H | CH₃ | S | Thymine |
| triphosphate | H | H | CH₃ | S | Cytosine |
| monophosphate | monophosphate | Br | CF₃ | O | 2,4-O-Diacetyluracil |
| monophosphate | monophosphate | Br | CF₃ | O | Hypoxanthine |
| monophosphate | monophosphate | Br | CF₃ | O | 2,4-O-Diacetylthymine |
| monophosphate | monophosphate | Br | CF₃ | O | Thymine |
| monophosphate | monophosphate | Br | CF₃ | O | Cytosine |
| monophosphate | monophosphate | Br | CF₃ | O | 4-(N-mono-acetyl)cytosine |
| monophosphate | monophosphate | Br | CF₃ | O | 4-(N,N-diacetyl)cytosine |
| monophosphate | monophosphate | Br | CF₃ | O | Uracil |
| monophosphate | monophosphate | Br | CF₃ | O | 5-Fluorouracil |
| monophosphate | monophosphate | Br | CF₃ | S | 2,4-O-Diacetyluracil |
| monophosphate | monophosphate | Br | CF₃ | S | Hypoxanthine |
| monophosphate | monophosphate | Br | CF₃ | S | 2,4-O-Diacetylthymine |
| monophosphate | monophosphate | Br | CF₃ | S | Thymine |
| monophosphate | monophosphate | Br | CF₃ | S | Cytosine |
| monophosphate | monophosphate | Br | CF₃ | S | 4-(N-mono-acetyl)cytosine |
| monophosphate | monophosphate | Br | CF₃ | S | 4-(N,N-diacetyl)cytos |
| monophosphate | monophosphate | Br | CF₃ | S | Uracil |
| monophosphate | monophosphate | Br | CF₃ | S | 5-Fluorouracil |
| acetyl | acetyl | NO2 | CF₃ | O | 4-(N,N-diacetyl)cytosine |
| acetyl | acetyl | NO2 | CF₃ | S | 4-(N,N-diacetyl)cytosine |
| acetyl | acetyl | NO2 | CF₃ | O | 4-(N,N-diacetyl)cytosine |
| acetyl | acetyl | NO2 | 2-bromo-vinyl | S | 4-(N,N-diacetyl)cytosine |

Alternatively, the following nucleosides of Formula XII are prepared, using the appropriate sugar and pyrimidine or purine bases.

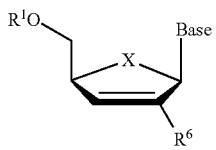

(XII)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytosine |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphosphate | CH₃ | S | 2,4-O-Diacetylthymine |
| triphosphate | CH₃ | S | Thymine |
| triphosphate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| Acetyl | 2-bromo-vinyl | S | 4-(N,N-diacetyl)cytosine |

Alternatively, the following nucleosides of Formula XVII are prepared, using the appropriate sugar and pyrimidine or purine bases.

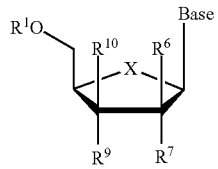

(XVII)

wherein

| R¹ | R⁶ | R⁷ | X | Base | R⁹ | R¹⁰ |
|---|---|---|---|---|---|---|
| H | CH₃ | H | O | 2,4-O-Diacetyluracil | NHAc | Me |
| H | CH₃ | H | O | Hypoxanthine | NH2 | Me |
| H | CH₃ | H | O | 2,4-O-Diacetylthymine | NHAc | Me |
| H | CH₃ | H | O | Thymine | NH2 | Me |
| H | CH₃ | H | O | Cytosine | NH2 | Me |
| H | CH₃ | H | O | 4-(N-mono-acetyl)cytosine | NHAc | Me |
| H | CH₃ | H | O | 4-(N,N-diacetyl)cytosine | NHAc | Me |
| H | CH₃ | H | O | Uracil | NH2 | Me |
| H | CH₃ | H | O | 5-Fluorouracil | NH2 | Me |
| H | CH₃ | H | S | 2,4-O-Diacetyluracil | NHAc | Me |
| H | CH₃ | H | S | Hypoxanthine | NH2 | Me |
| H | CH₃ | H | S | 2,4-O-Diacetylthymine | NHAc | Me |
| H | CH₃ | H | S | Thymine | NH2 | Me |
| H | CH₃ | H | S | Cytosine | NH2 | Me |

-continued

| R¹ | R⁶ | R⁷ | X | Base | R⁹ | R¹⁰ |
|---|---|---|---|---|---|---|
| H | CH₃ | H | S | 4-(N-mono-acetyl)cytosine | NHAc | Me |
| H | CH₃ | H | S | 4-(N,N-diacetyl)cytosine | NHAc | Me |
| H | CH₃ | H | S | Uracil | NH2 | Me |
| H | CH₃ | H | S | 5-Fluorouracil | NH2 | Me |
| monophosphate | CH₃ | H | O | 2,4-O-Diacetyluracil | NHAc | Me |
| monophosphate | CH₃ | H | O | Hypoxanthine | NH2 | Me |
| monophosphate | CH₃ | H | O | 2,4-O-Diacetylthymine | NHAc | Me |
| monophosphate | CH₃ | H | O | Thymine | NH2 | Me |
| monophosphate | CH₃ | H | O | Cytosine | NH2 | Me |
| monophosphate | CH₃ | H | O | 4-(N-mono-acetyl)cytosine | NHAC | Me |
| monophosphate | CH₃ | H | O | 4-(N,N-diacetyl)cytosine | NHAc | Me |
| monophosphate | CH₃ | H | O | Uracil | NH2 | Me |
| monophosphate | CH₃ | H | O | 5-Fluorouracil | NH2 | Me |
| monophosphate | CH₃ | H | S | 2,4-O-Diacetyluracil | NHAc | Me |
| monophosphate | CH₃ | H | S | Hypoxanthine | NH2 | Me |
| monophosphate | CH₃ | H | S | 2,4-O-Diacetylthymine | NHAc | Me |
| monophosphate | CH₃ | H | S | Thymine | NH2 | Me |
| monophosphate | CH₃ | H | S | Cytosine | NH2 | Me |
| monophosphate | CH₃ | H | S | 4-(N-mono-acetyl)cytosine | NHAc | Me |
| monophosphate | CH₃ | H | S | 4-(N,N-diacetyl)cytosine | NHAc | Me |
| monophosphate | CH₃ | H | S | Uracil | NH2 | Me |
| monophosphate | CH₃ | H | S | 5-Fluorouracil | NH2 | Me |
| diphosphate | CH₃ | H | O | 2,4-O-Diacetyluracil | NHAc | Me |
| diphosphate | CH₃ | H | O | Hypoxanthine | NH2 | Me |
| diphosphate | CH₃ | H | O | 2,4-O-Diacetylthymine | NH2 | Me |
| diphosphate | CH₃ | H | O | Thymine | NH2 | Me |
| diphosphate | CH₃ | H | O | Cytosine | NH2 | Me |
| diphosphate | CH₃ | H | O | 4-(N-mono-acetyl)cytosine | NHAc | Me |
| diphosphate | CH₃ | H | O | 4-(N,N-diacetyl)cytos | NHAc | Me |
| diphosphate | CH₃ | H | O | Uracil | NH2 | Me |
| diphosphate | CH₃ | H | O | 5-Fluorouracil | NH2 | Me |
| diphosphate | CH₃ | H | S | 2,4-O-Diacetyluracil | NH2 | Me |
| diphosphate | CH₃ | H | S | Hypoxanthine | NH2 | Me |
| diphosphate | CH₃ | H | S | 2,4-O-Diacetylthymine | NHAc | Me |
| diphosphate | CH₃ | H | S | Thymine | NH2 | Me |
| diphosphate | CH₃ | H | S | Cytosine | NH2 | Me |
| triphosphate | CH₃ | H | O | 2,4-O-Diacetyluracil | NHAc | Me |
| triphosphate | CH₃ | H | O | Hypoxanthine | NHAc | Me |
| triphosphate | CH₃ | H | O | 2,4-O-Diacetylthymine | NHAc | Me |
| triphosphate | CH₃ | H | O | Thymine | NH2 | Me |
| triphosphate | CH₃ | H | O | Cytosine | NH2 | Me |
| triphosphate | CH₃ | H | O | 4-(N-mono-acetyl)cytosine | NHAc | Me |
| triphosphate | CH₃ | H | O | 4-(N,N-diacetyl)cytosine | NH2 | Me |
| triphosphate | CH₃ | H | O | Uracil | NH2 | Me |
| triphosphate | CH₃ | H | O | 5-Fluorouracil | NH2 | Me |
| triphosphate | CH₃ | H | S | 2,4-O-Diacetyluracil | NH2 | Me |
| triphosphate | CH₃ | H | S | Hypoxanthine | NH2 | Me |
| triphosphate | CH₃ | H | S | 2,4-O-Diacetylthymine | NH2 | Me |
| triphosphate | CH₃ | H | S | Thymine | NH2 | Me |
| triphosphate | CH₃ | H | S | Cytosine | NH2 | Me |
| monophosphate | CF₃ | H | O | 2,4-O-Diacetyluracil | NH2 | Me |
| monophosphate | CF₃ | H | O | Hypoxanthine | NH2 | Me |
| monophosphate | CF₃ | H | O | 2,4-O-Diacetylthymine | NH2 | Me |
| monophosphate | CF₃ | H | O | Thymine | NH2 | Me |
| monophosphate | CF₃ | H | O | Cytosine | NH2 | Me |
| monophosphate | CF₃ | H | O | 4-(N-mono-acetyl)cytosine | NH2 | Me |
| monophosphate | CF₃ | H | O | 4-(N,N-diacetyl)cytosine | NH2 | Me |
| monophosphate | CF₃ | H | O | Uracil | NH2 | Me |
| monophosphate | CF₃ | H | O | 5-Fluorouracil | NH2 | Me |
| monophosphate | CF₃ | H | S | 2,4-O-Diacetyluracil | NH2 | Me |
| monophosphate | CF₃ | H | S | Hypoxanthine | NH2 | Me |
| monophosphate | CF₃ | H | S | 2,4-O-Diacetylthymine | NH2 | Me |
| monophosphate | CF₃ | H | S | Thymine | NH2 | Me |
| monophosphate | CF₃ | H | S | Cytosine | NH2 | Me |
| monophosphate | CF₃ | H | S | 4-(N-mono-acetyl)cytosine | NH2 | Me |
| monophosphate | CF₃ | H | S | 4-(N,N-diacetyl)cytosine | NH2 | Me |
| monophosphate | CF₃ | H | S | Uracil | NH2 | Me |
| monophosphate | CF₃ | H | S | 5-Fluorouracil | NH2 | Me |
| acetyl | CH₃ | H | O | 4-(N,N-diacetyl)cytosine | H | Br |
| acetyl | CH₃ | H | S | 4-(N,N-diacetyl)cytosine | H | Br |
| acetyl | CH₃ | OH | O | 4-(N,N-diacetyl)cytosine | H | Br |
| acetyl | CH₃ | OH | S | 4-(N,N-diacetyl)cytosine | H | Br |

Example 3: Preparation of 3'-C-methylriboadenine

The title compound can be prepared according to a published procedure (R. F. Nutt, M. J. Dickinson, F. W. Holly, and E. Walton, "Branched-chain sugar nucleosides. III. 3'-C-methyladenine", *J. Org. Chem.* 1968, 33, 1789-1795) (Scheme 9).

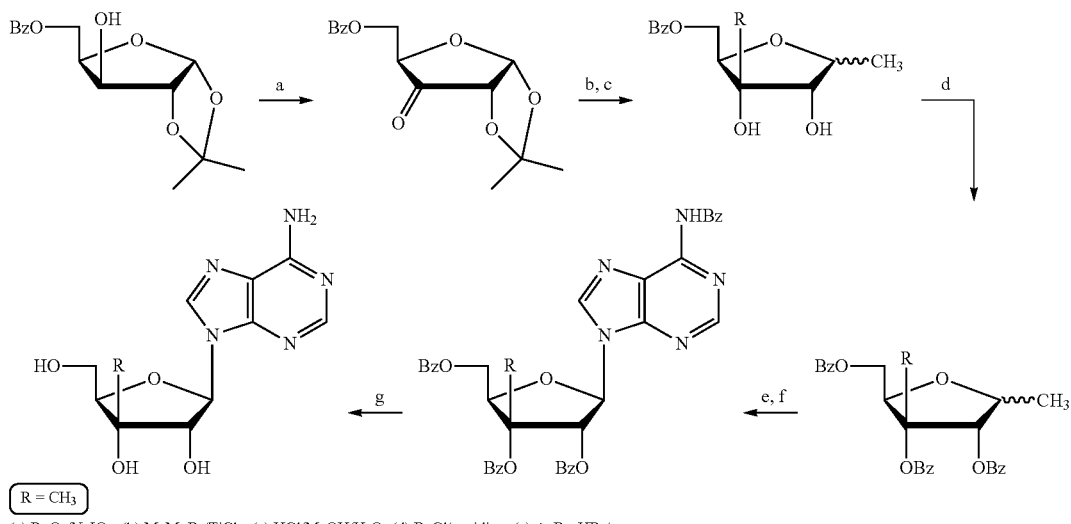

(a) RuO₂/NaIO₄; (b) MeMgBr/TiCl₄; (c) HCl/MeOH/H₂O; (d) BzCl/pyridine; (e) AcBr, HBr/AcOH; (f) chloromercuri-6-benzamidopurine; (g) NH₃/MeOH.

In a similar manner, but using the appropriate sugar and pyrimidine or purine bases, the following nucleosides of Formula III are prepared.

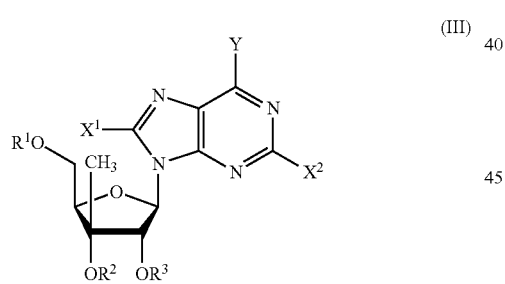

(III)

wherein:

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |

-continued

| R¹ | R² | R³ | X¹ | X² | Y |
|---|---|---|---|---|---|
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | NH₂ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | NH₂ |
| H | H | H | F | H | NH-cyclopropyl |
| H | H | H | F | H | OH |

-continued

| R¹ | R² | R³ | X¹ | X² | Y |
|---|---|---|---|---|---|
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |
| H | H | H | Br | H | F |
| H | H | H | Br | H | Cl |
| H | H | H | $NH_2$ | H | $NH_2$ |
| H | H | H | $NH_2$ | H | NH-cyclopropyl |
| H | H | H | $NH_2$ | H | OH |
| H | H | H | $NH_2$ | H | F |
| H | H | H | $NH_2$ | H | Cl |
| H | H | H | SH | H | $NH_2$ |
| H | H | H | SH | H | NH-cyclopropyl |
| H | H | H | SH | H | OH |
| H | H | H | SH | H | F |
| H | H | H | SH | H | Cl |
| acetyl | H | H | H | H | $NH_2$ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | $NH_2$ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | $NH_2$ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | $NH_2$ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | $NH_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | $NH_2$ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | $NH_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | $NH_2$ | H |
| H | H | H | H | $NH_2$ | $NH_2$ |
| H | H | H | H | $NH_2$ | NH-cyclopropyl |
| H | H | H | H | $NH_2$ | NH-methyl |
| H | H | H | H | $NH_2$ | NH-ethyl |
| H | H | H | H | $NH_2$ | NH-acetyl |
| H | H | H | H | $NH_2$ | OH |
| H | H | H | H | $NH_2$ | OMe |
| H | H | H | H | $NH_2$ | OEt |
| H | H | H | H | $NH_2$ | O-cyclopropyl |
| H | H | H | H | $NH_2$ | O-acetyl |
| H | H | H | H | $NH_2$ | SH |
| H | H | H | H | $NH_2$ | SMe |
| H | H | H | H | $NH_2$ | SEt |
| H | H | H | H | $NH_2$ | S-cyclopropyl |
| H | H | H | H | $NH_2$ | F |
| H | H | H | H | $NH_2$ | Cl |
| H | H | H | H | $NH_2$ | Br |
| H | H | H | H | $NH_2$ | I |
| monophosphate | H | H | H | $NH_2$ | $NH_2$ |

-continued

| R¹ | R² | R³ | X¹ | X² | Y |
|---|---|---|---|---|---|
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |

-continued

| R¹ | R² | R³ | X¹ | X² | Y |
|---|---|---|---|---|---|
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |

-continued

| R¹ | R² | R³ | X¹ | X² | Y |
|---|---|---|---|---|---|
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | $NH_2$ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | $NH_2$ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | $NH_2$ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | $NH_2$ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | $NH_2$ |
| triphosphate | triphosphate | triphosphate | H | Cl | NH-cyclopropyl |
| triphosphate | triphosphate | triphosphate | H | Cl | OH |
| H | H | H | F | Cl | $NH_2$ |
| H | H | H | F | Cl | NH-cyclopropyl |
| H | H | H | F | Cl | OH |
| H | H | H | Cl | Cl | $NH_2$ |
| H | H | H | Cl | Cl | NH-cyclopropyl |
| H | H | H | Cl | Cl | OH |
| H | H | H | Br | Cl | $NH_2$ |
| H | H | H | Br | Cl | NH-cyclopropyl |
| H | H | H | Br | Cl | OH |
| H | H | H | $NH_2$ | Cl | $NH_2$ |
| H | H | H | $NH_2$ | Cl | NH-cyclopropyl |
| H | H | H | $NH_2$ | Cl | OH |
| H | H | H | SH | Cl | $NH_2$ |
| H | H | H | SH | Cl | NH-cyclopropyl |
| H | H | H | SH | Cl | OH |
| acetyl | H | H | H | Cl | $NH_2$ |
| acetyl | H | H | H | Cl | NH-cyclopropyl |
| acetyl | H | H | H | Cl | OH |
| acetyl | H | H | F | Cl | $NH_2$ |
| acetyl | H | H | F | Cl | NH-cyclopropyl |
| acetyl | H | H | F | Cl | OH |
| H | acetyl | acetyl | H | Cl | $NH_2$ |
| H | acetyl | acetyl | H | Cl | NH-cyclopropyl |
| H | acetyl | acetyl | H | Cl | OH |
| acetyl | acetyl | acetyl | H | Cl | $NH_2$ |
| acetyl | acetyl | acetyl | H | Cl | NH-cyclopropyl |
| acetyl | acetyl | acetyl | H | Cl | OH |
| monophosphate | acetyl | acetyl | H | Cl | $NH_2$ |
| monophosphate | acetyl | acetyl | H | Cl | NH-cyclopropyl |
| monophosphate | acetyl | acetyl | H | Cl | OH |
| diphosphate | acetyl | acetyl | H | Cl | $NH_2$ |
| diphosphate | acetyl | acetyl | H | Cl | NH-cyclopropyl |
| diphosphate | acetyl | acetyl | H | Cl | OH |
| triphosphate | acetyl | acetyl | H | Cl | $NH_2$ |
| triphosphate | acetyl | acetyl | H | Cl | NH-cyclopropyl |
| triphosphate | acetyl | acetyl | H | Cl | OH |

-continued

| R¹ | R² | R³ | X¹ | X² | Y |
|---|---|---|---|---|---|
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula VI are prepared, using the appropriate sugar and pyrimidine or purine bases.

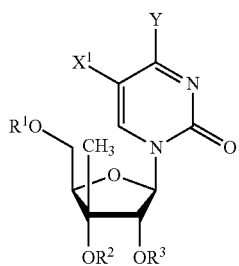

(VI)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | NH₂ |
| monophosphate | monophosphate | monophosphate | H | NH-cyclopropyl |
| monophosphate | monophosphate | monophosphate | H | OH |
| diphosphate | diphosphate | diphosphate | H | NH₂ |
| diphosphate | diphosphate | diphosphate | H | NH-cyclopropyl |
| diphosphate | diphosphate | diphosphate | H | OH |
| triphosphate | triphosphate | triphosphate | H | NH₂ |
| triphosphate | triphosphate | triphosphate | H | NH-cyclopropyl |
| triphosphate | triphosphate | triphosphate | H | OH |
| H | H | H | F | NH₂ |
| H | H | H | F | NH-cyclopropyl |
| H | H | H | F | OH |
| H | H | H | Cl | NH₂ |
| H | H | H | Cl | NH-cyclopropyl |
| H | H | H | Cl | OH |
| H | H | H | Br | NH₂ |
| H | H | H | Br | NH-cyclopropyl |
| H | H | H | Br | OH |
| H | H | H | NH₂ | NH₂ |
| H | H | H | NH₂ | NH-cyclopropyl |
| H | H | H | NH₂ | OH |
| H | H | H | SH | NH₂ |
| H | H | H | SH | NH-cyclopropyl |
| H | H | H | SH | OH |
| acetyl | H | H | H | NH₂ |
| acetyl | H | H | H | NH-cyclopropyl |
| acetyl | H | H | H | OH |
| acetyl | H | H | F | NH₂ |
| acetyl | H | H | F | NH-cyclopropyl |
| acetyl | H | H | F | OH |
| H | acetyl | acetyl | H | NH₂ |
| H | acetyl | acetyl | H | NH-cyclopropyl |
| H | acetyl | acetyl | H | OH |
| acetyl | acetyl | acetyl | H | NH₂ |

-continued

| R¹ | R² | R³ | X¹ | Y |
|---|---|---|---|---|
| acetyl | acetyl | acetyl | H | NH-cyclopropyl |
| acetyl | acetyl | acetyl | H | OH |
| monophosphate | acetyl | acetyl | H | NH₂ |
| monophosphate | acetyl | acetyl | H | NH-cyclopropyl |
| monophosphate | acetyl | acetyl | H | OH |
| diphosphate | acetyl | acetyl | H | NH₂ |
| diphosphate | acetyl | acetyl | H | NH-cyclopropyl |
| diphosphate | acetyl | acetyl | H | OH |
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula XIII are prepared, using the appropriate sugar and pyrimidine or purine bases.

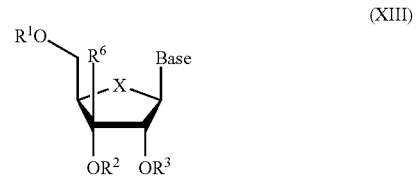

(XIII)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |

-continued

| R¹ | R² | R³ | R⁶ | X | Base |
|---|---|---|---|---|---|
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |

-continued

| R¹ | R² | R³ | R⁶ | X | Base |
|---|---|---|---|---|---|
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |

-continued

| R¹ | R² | R³ | R⁶ | X | Base |
|---|---|---|---|---|---|
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoro-adenine |
| monophosphate | monophosphate | monophosphate | CF₃ | O | adenine |
| monophosphate | monophosphate | monophosphate | CF₃ | S | 2-(N,N-diacetyl)-guanine |
| monophosphate | monophosphate | monophosphate | CF₃ | S | 6-O-acetyl guanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)-adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoro-adenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula XIV are prepared, using the appropriate sugar and pyrimidine or purine bases.

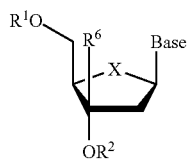

(XIV)

wherein:

| R¹ | R² | R⁶ | X | Base |
|---|---|---|---|---|
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |

-continued

| R¹ | R² | R⁶ | X | Base |
|---|---|---|---|---|
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosin |
| H | H | CH₃ | S | 4-(N,N-diacetyl)cytosine |
| H | H | CH₃ | S | Uracil |
| H | H | CH₃ | S | 5-Fluorouracil |
| monophosphate | H | CH₃ | O | 2,4-O-Diacetyluracil |
| monophosphate | H | CH₃ | O | Hypoxanthine |
| monophosphate | H | CH₃ | O | 2,4-O-Diacetylthym |
| monophosphate | H | CH₃ | O | Thymine |
| monophosphate | H | CH₃ | O | Cytosine |
| monophosphate | H | CH₃ | O | 4-(N-mono-acetyl)cytosine |
| monophosphate | H | CH₃ | O | 4-(N,N-diacetyl)cytos |
| monophosphate | H | CH₃ | O | Uracil |
| monophosphate | H | CH₃ | O | 5-Fluorouracil |
| monophosphate | H | CH₃ | S | 2,4-O-Diacetyluracil |
| monophosphate | H | CH₃ | S | Hypoxanthine |
| monophosphate | H | CH₃ | S | 2,4-O-Diacetylthym |
| monophosphate | H | CH₃ | S | Thymine |
| monophosphate | H | CH₃ | S | Cytosine |

-continued

| R¹ | R² | R⁶ | X | Base |
|---|---|---|---|---|
| monophosphate | H | CH₃ | S | 4-(N-mono-acetyl)cytosine |
| monophosphate | H | CH₃ | S | 4-(N,N-diacetyl)cytosine |
| monophosphate | H | CH₃ | S | Uracil |
| monophosphate | H | CH₃ | S | 5-Fluorouracil |
| diphosphate | H | CH₃ | O | 2,4-O-Diacetyluracil |
| diphosphate | H | CH₃ | O | Hypoxanthine |
| diphosphate | H | CH₃ | O | 2,4-O-Diacetylthymine |
| diphosphate | H | CH₃ | O | Thymine |
| diphosphate | H | CH₃ | O | Cytosine |
| diphosphate | H | CH₃ | O | 4-(N-mono-acetyl)cytosine |
| diphosphate | H | CH₃ | O | 4-(N,N-diacetyl)cytosine |
| diphosphate | H | CH₃ | O | Uracil |
| diphosphate | H | CH₃ | O | 5-Fluorouracil |
| diphosphate | H | CH₃ | S | 2,4-O-Diacetyluracil |
| diphosphate | H | CH₃ | S | Hypoxanthine |
| diphosphate | H | CH₃ | S | 2,4-O-Diacetylthymine |
| diphosphate | H | CH₃ | S | Thymine |
| diphosphate | H | CH₃ | S | Cytosine |
| triphosphate | H | CH₃ | O | 2,4-O-Diacetyluracil |
| triphosphate | H | CH₃ | O | Hypoxanthine |
| triphosphate | H | CH₃ | O | 2,4-O-Diacetylthymine |
| triphosphate | H | CH₃ | O | Thymine |
| triphosphate | H | CH₃ | O | Cytosine |
| triphosphate | H | CH₃ | O | 4-(N-mono-acetyl)cytosine |
| triphosphate | H | CH₃ | O | 4-(N,N-diacetyl)cytosine |
| triphosphate | H | CH₃ | O | Uracil |
| triphosphate | H | CH₃ | O | 5-Fluorouracil |
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |

Alternatively, the following nucleosides of Formula XV are prepared, using the appropriate sugar and pyrimidine or purine bases.

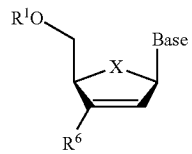

(XV)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytosine |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphosphate | CH₃ | S | 2,4-O-Diacetylthymine |
| triphosphate | CH₃ | S | Thymine |
| triphosphate | CH₃ | S | Cytosine |
| monophosphate | CF₃ | O | 2,4-O-Diacetyluracil |

-continued

| R¹ | R⁶ | X | Base |
|---|---|---|---|
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVIII are prepared, using the appropriate sugar and pyrimidine or purine bases.

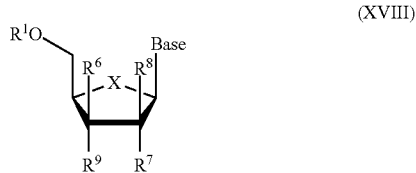

(XVIII)

wherein:

| R¹ | R⁶ | R⁷ | X | Base | R⁸ | R⁹ |
|---|---|---|---|---|---|---|
| H | CH₃ | OH | O | 2,4-O-Diacetyluracil | H | Me |
| H | CH₃ | OH | O | Hypoxanthine | H | Me |
| H | CH₃ | OH | O | 2,4-O-Diacetylthymine | H | Me |
| H | CH₃ | OH | O | Thymine | H | Me |
| H | CH₃ | OH | O | Cytosine | H | Me |
| H | CH₃ | OH | O | 4-(N-mono-acetyl)cytosine | H | Me |
| H | CH₃ | OH | O | 4-(N,N-diacetyl)cytosine | H | Me |
| H | CH₃ | OH | O | Uracil | H | Me |
| H | CH₃ | OH | O | 5-Fluorouracil | H | Me |
| H | CH₃ | OH | S | 2,4-O-Diacetyluracil | H | Me |
| H | CH₃ | OH | S | Hypoxanthine | H | Me |
| H | CH₃ | OH | S | 2,4-O-Diacetylthymine | H | Me |
| H | CH₃ | OH | S | Thymine | H | Me |
| H | CH₃ | OH | S | Cytosine | H | Me |
| H | CH₃ | OH | S | 4-(N-mono-acetyl)cytosine | H | Me |
| H | CH₃ | OH | S | 4-(N,N-diacetyl)cytosine | H | Me |
| H | CH₃ | OH | S | Uracil | H | Me |
| H | CH₃ | OH | S | 5-Fluorouracil | H | Me |
| monophosphate | CH₃ | OH | O | 2,4-O-Diacetyluracil | H | Me |
| monophosphate | CH₃ | OH | O | Hypoxanthine | H | Me |
| monophosphate | CH₃ | OH | O | 2,4-O-Diacetylthymine | H | Me |
| monophosphate | CH₃ | OH | O | Thymine | H | Me |
| monophosphate | CH₃ | OH | O | Cytosine | H | Me |
| monophosphate | CH₃ | OH | O | 4-(N-mono-acetyl)cytosine | H | Me |
| monophosphate | CH₃ | OH | O | 4-(N,N-diacetyl)cytosine | H | Me |
| monophosphate | CH₃ | OH | O | Uracil | H | Me |
| monophosphate | CH₃ | OH | O | 5-Fluorouracil | H | Me |
| monophosphate | CH₃ | OH | S | 2,4-O-Diacetyluracil | H | Me |
| monophosphate | CH₃ | OH | S | Hypoxanthine | H | Me |
| monophosphate | CH₃ | OH | S | 2,4-O-Diacetylthymine | H | Me |
| monophosphate | CH₃ | OH | S | Thymine | H | Me |
| monophosphate | CH₃ | OH | S | Cytosine | H | Me |
| monophosphate | CH₃ | OH | S | 4-(N-mono-acetyl)cytosine | H | Me |
| monophosphate | CH₃ | OH | S | 4-(N,N-diacetyl)cytosine | H | Me |
| monophosphate | CH₃ | OH | S | Uracil | H | Me |
| monophosphate | CH₃ | OH | S | 5-Fluorouracil | H | Me |
| diphosphate | CH₃ | OH | O | 2,4-O-Diacetyluracil | H | Me |
| diphosphate | CH₃ | OH | O | Hypoxanthine | H | Me |
| diphosphate | CH₃ | OH | O | 2,4-O-Diacetylthymine | H | Me |
| diphosphate | CH₃ | OH | O | Thymine | H | Me |
| diphosphate | CH₃ | OH | O | Cytosine | H | Me |
| diphosphate | CH₃ | OH | O | 4-(N-mono-acetyl)cytosine | H | Me |
| diphosphate | CH₃ | OH | O | 4-(N,N-diacetyl)cytosine | H | Me |
| diphosphate | CH₃ | OH | O | Uracil | H | Me |
| diphosphate | CH₃ | OH | O | 5-Fluorouracil | H | Me |
| diphosphate | CH₃ | OH | S | 2,4-O-Diacetyluracil | H | Me |
| diphosphate | CH₃ | OH | S | Hypoxanthine | H | Me |
| diphosphate | CH₃ | OH | S | 2,4-O-Diacetylthymine | H | Me |
| diphosphate | CH₃ | OH | S | Thymine | H | Me |
| diphosphate | CH₃ | OH | S | Cytosine | H | Me |
| triphosphate | CH₃ | OH | O | 2,4-O-Diacetyluracil | H | Me |
| triphosphate | CH₃ | OH | O | Hypoxanthine | H | Me |
| triphosphate | CH₃ | OH | O | 2,4-O-Diacetylthymine | H | Me |
| triphosphate | CH₃ | OH | O | Thymine | H | Me |
| triphosphate | CH₃ | OH | O | Cytosine | H | Me |
| triphosphate | CH₃ | OH | O | 4-(N-mono-acetyl)cytosine | H | Me |
| triphosphate | CH₃ | OH | O | 4-(N,N-diacetyl)cytosine | H | Me |
| triphosphate | CH₃ | OH | O | Uracil | H | Me |
| triphosphate | CH₃ | OH | O | 5-Fluorouracil | H | Me |
| triphosphate | CH₃ | OH | S | 2,4-O-Diacetyluracil | H | Me |
| triphosphate | CH₃ | OH | S | Hypoxanthine | H | Me |
| triphosphate | CH₃ | OH | S | 2,4-O-Diacetylthymine | H | Me |
| triphosphate | CH₃ | OH | S | Thymine | H | Me |
| triphosphate | CH₃ | OH | S | Cytosine | H | Me |
| monophosphate | CF₃ | OH | O | 2,4-O-Diacetyluracil | H | Me |
| monophosphate | CF₃ | OH | O | Hypoxanthine | H | Me |
| monophosphate | CF₃ | OH | O | 2,4-O-Diacetylthymine | H | Me |
| monophosphate | CF₃ | OH | O | Thymine | H | Me |
| monophosphate | CF₃ | OH | O | Cytosine | H | Me |
| monophosphate | CF₃ | OH | O | 4-(N-mono-acetyl)cytosine | H | Me |
| monophosphate | CF₃ | OH | O | 4-(N,N-diacetyl)cytosine | H | Me |
| monophosphate | CF₃ | OH | O | Uracil | H | Me |
| monophosphate | CF₃ | OH | O | 5-Fluorouracil | H | Me |
| monophosphate | CF₃ | OH | S | 2,4-O-Diacetyluracil | H | Me |
| monophosphate | CF₃ | OH | S | Hypoxanthine | H | Me |
| monophosphate | CF₃ | OH | S | 2,4-O-Diacetylthymine | H | Me |
| monophosphate | CF₃ | OH | S | Thymine | H | Me |
| monophosphate | CF₃ | OH | S | Cytosine | H | Me |
| monophosphate | CF₃ | OH | S | 4-(N-mono-acetyl)cytosine | H | Me |
| monophosphate | CF₃ | OH | S | 4-(N,N-diacetyl)cytosine | H | Me |
| monophosphate | CF₃ | OH | S | Uracil | H | Me |
| monophosphate | CF₃ | OH | S | 5-Fluorouracil | H | Me |
| acetyl | CH₃ | OH | O | 4-(N,N-diacetyl)cytosine | H | Br |
| acetyl | CH₃ | OH | S | 4-(N,N-diacetyl)cytosine | H | Br |

VII. Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al., *Jnl. of Vir.*, 73:1649-1654, 1999; Ishii et al., *Hepatology*, 29:1227-1235,1999; Lohmann et al., *Jnl. of Bio. Chem.*, 274:10807-10815, 1999; and Yamashita et al, *Jnl. of Bio. Chem.*, 273:15479-15486, 1998.

WO 97/12033, filed on Sep. 27, 1996, by Emory University, listing C. Hagedorn and A. Reinoldus as inventors, and which claims priority to U.S. Ser. No. 60/004,383, filed on September 1995, describes an HCV polymerase assay that can be used to evaluate the activity of the compounds described herein. Another HCV polymerase assay has been reported by Bartholomeusz, et al., Hepatitis C virus (HCV)

RNA polymerase assay using cloned HCV non-structural proteins; Antiviral Therapy 1996:1(Supp 4) 18-24.

Screens that measure reductions in kinase activity from HCV drugs are disclosed in U.S. Pat. No. 6,030,785, to Katze et al., U.S. Pat. No. 6,010,848 to Delvecchio et al, and U.S. Pat. No. 5,759,795 to Jubin et al. Screens that measure the protease inhibiting activity of proposed HCV drugs are disclosed in U.S. Pat. No. 5,861,267 to Su et al, U.S. Pat. No. 5,739,002 to De Francesco et al, and U.S. Pat. No. 5,597,691 to Houghton et al.

Example 4: Phosphorylation Assay of Nucleoside to Active Triphosphate

To determine the cellular metabolism of the compounds, HepG2 cells were obtained from the American Type Culture Collection (Rockville, Md.), and were grown in 225 cm$^2$ tissue culture flasks in minimal essential medium supplemented with non-essential amino acids, 1% penicillin-streptomycin. The medium was renewed every three days, and the cells were subcultured once a week. After detachment of the adherent monolayer with a 10 minute exposure to 30 mL of trypsin-EDTA and three consecutive washes with medium, confluent HepG2 cells were seeded at a density of 2.5×10$^6$ cells per well in a 6-well plate and exposed to 10 μM of [$^3$H] labeled active compound (500 dpm/pmol) for the specified time periods. The cells were maintained at 37° C. under a 5% CO$_2$ atmosphere. At the selected time points, the cells were washed three times with ice-cold phosphate-buffered saline (PBS). Intracellular active compound and its respective metabolites were extracted by incubating the cell pellet overnight at −20° C. with 60% methanol followed by extraction with an additional 20 μL of cold methanol for one hour in an ice bath. The extracts were then combined, dried under gentle filtered air flow and stored at −20° C. until HPLC analysis. The preliminary results of the HPLC analysis are tabulated in Table 1.

TABLE 1

| | [pmol/million cells] | | | |
|---|---|---|---|---|
| Time (h) | β-D-2'-CH$_3$-riboA-TP | β-D-2'-CH$_3$-riboU-TP | β-D-2'-CH$_3$-riboC-TP | β-D-2'-CH$_3$-riboG-TP |
| 2 | 33.1 | 0.40 | 2.24 | ND |
| 4 | 67.7 | 1.21 | 3.99 | ND |
| 8 | 147 | 1.57 | 9.76 | 2.85 |
| 24 | 427 | 6.39 | 34.9 | 0.91 |
| 30 | 456 | 7.18 | 36.2 | 3.22 |
| 48 | 288 | 9.42 | 56.4 | 6.26 |

Example 5: Bioavailability Assay in Cynomolgus Monkeys

Figure 2:
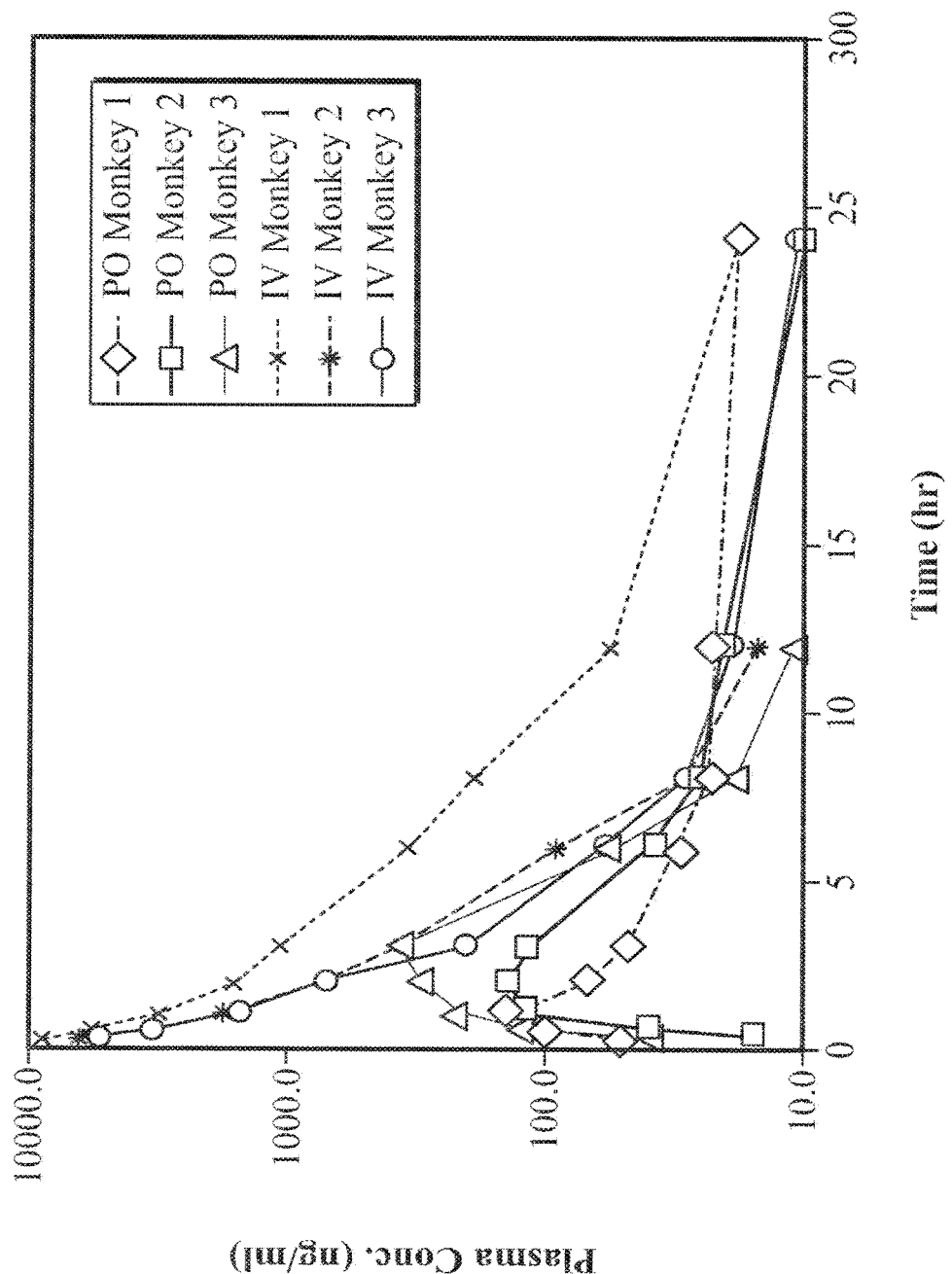
FIG. 2 is a line graph of the pharmacokinetics (plasma concentrations) of β-D-2'-CH$_3$-riboG administered to six Cynomolgus Monkeys over time after administration.
Figure 3A:
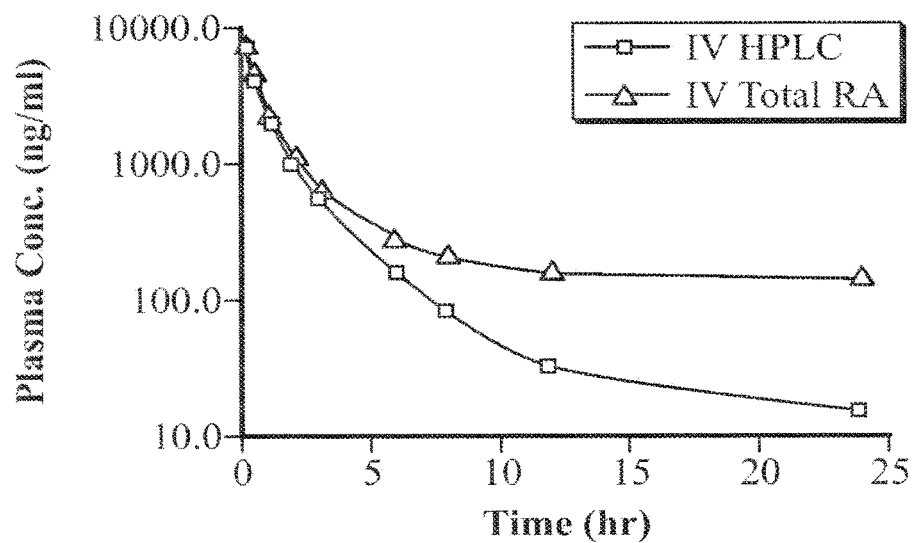
FIGS. 3a and 3b are line graphs of the pharmacokinetics (plasma concentrations) of β-D-2'-CH$_3$-riboG administered to Cynomolgus Monkeys either intravenously (3a) or orally (3b) over time after administration.
Figure 3B:
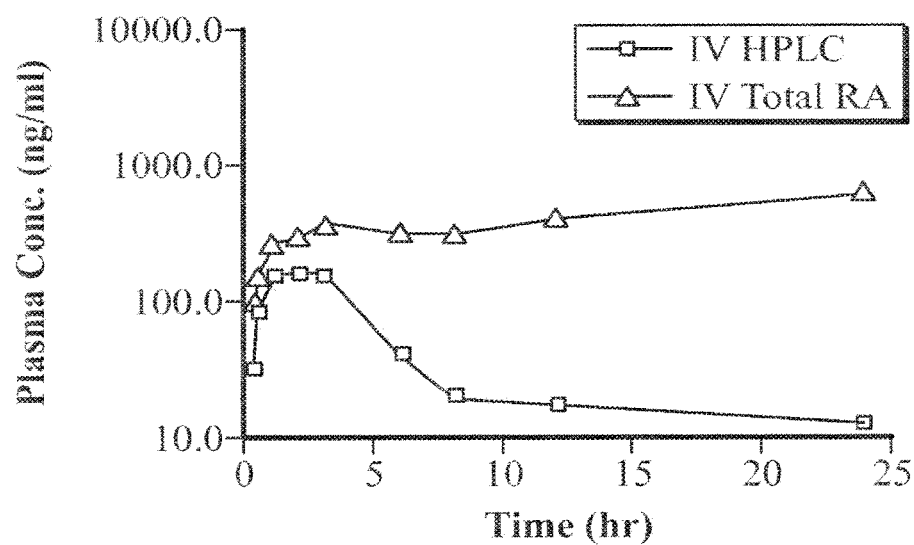

Within 1 week prior to the study initiation, the cynomolgus monkey was surgically implanted with a chronic venous catheter and subcutaneous venous access port (VAP) to facilitate blood collection and underwent a physical examination including hematology and serum chemistry evaluations and the body weight was recorded. Each monkey (six total), received approximately 250 uCi of $^3$H activity with each dose of active compound, namely β-D-2'-CH$_3$-riboG at a dose level of 10 mg/kg at a dose concentration of 5 mg/mL, either via an intravenous bolus (3 monkeys, IV), or via oral gavage (3 monkeys, PO). Each dosing syringe was weighed before dosing to gravimetrically determine the quantity of formulation administered. Urine samples were collected via pan catch at the designated intervals (approximately 18-0 hours pre-dose, 0-4, 4-8 and 8-12 hours post-dosage) and processed. Blood samples were collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples were analyzed for the maximum concentration ($C_{max}$), time when the maximum concentration was achieved ($T_{max}$), area under the curve (AUC), half life of the dosage concentration ($T_{1/2}$), clearance (CL), steady state volume and distribution ($V_{ss}$) and bioavailability (F), which are tabulated in Tables 2 and 3, and graphically illustrated in FIGS. 2 and 3, respectively.

TABLE 2

Oral Bioavailability in Monkeys

| | Dose (mg) | AUC (ng/mL × h) | Norm AUC (ng/mL × h/mg) | Mean Norm AUC (ng/mL × h/mg) | F (%) |
|---|---|---|---|---|---|
| IV Monkey 1 | 46.44 | 13614 | 293.2 | | |
| IV Monkey 2 | 24.53 | 6581 | 268.3 | | |
| IV Monkey 3 | 20.72 | 6079 | 293.4 | 284.9 | |
| PO Monkey 1 | 29.04 | 758 | 26.1 | | |
| PO Monkey 2 | 30.93 | 898 | 29.0 | | |
| PO Monkey 3 | 30.04 | 1842 | 61.3 | 38.8 | 13.6 |

TABLE 3

Experimental Pharmacokinetics of β-D-2'-CH$_3$-riboG in Cynomolgus Monkeys

| | IV | PO |
|---|---|---|
| Dose/Route (mg/kg) | 10 | 10 |
| $C_{max}$ (ng/mL) | 6945.6 ± 1886.0 | 217.7 ± 132.1 |
| $T_{max}$ (hr) | 0.25 ± 0.00 | 2.00 ± 1.00 |
| AUC (ng/mL × hr) | 8758.0 ± 4212.9 | 1166.0 ± 589.6 |
| $T_{1/2}$ (hr) | 7.9 ± 5.4 | 10.3 ± 4.1 |
| CL (L/hr/kg) | 1.28 ± 0.48 | |
| $V_{ss}$ (L/kg) | 2.09 ± 0.54 | |
| F (%) | | 13.8 |

Example 6: Bone Marrow Toxicity Assay

Human bone marrow cells were collected from normal healthy volunteers and the mononuclear population was separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921-1925. The culture assays for CFU-GM and BFU-E were performed using a bilayer soft agar or methylcellulose method. Drugs were diluted in tissue culture medium and filtered. After 14 to 18 days at 37° C. in a humidified atmosphere of 5% $CO_2$ in air, colonies of greater than 50 cells were counted using an inverted microscope. The results in Table 4 are presented as the percent inhibition of colony formation in the presence of drug compared to solvent control cultures.

TABLE 4

Human Bone Marrow Toxicity CFU-GM and BFU-E Clonogenic Assays

| Treatment | $IC_{50}$ in µM | |
| --- | --- | --- |
| | CFU-GM | BFU-E |
| ribavirin | ~5 | ~1 |
| β-D-2'-$CH_3$-riboA | >100 | >100 |
| β-D-2'-$CH_3$-riboU | >100 | >100 |
| β-D-2'-$CH_3$-riboC | >10 | >10 |
| β-D-2'-$CH_3$-riboG | >10 | >100 |

Example 7: Mitochondria Toxicity Assay

HepG2 cells were cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob Agents Chemother 2000; 44:496-503. Lactic acid levels in the culture medium after 4 day drug exposure was measured using a Boehringer lactic acid assay kit. Lactic acid levels were normalized by cell number as measured by hemocytometer count. The preliminary results from this assay are tabulated in Table 5.

TABLE 5

Mitochondrial Toxicity Study (L-lactic acid assay)

| | Conc. (µM) | lactate (mg/$10^6$ cell) | % of Control |
| --- | --- | --- | --- |
| Control | | 2.18 | |
| FIAU | 10 | 3.73 | 170.4 |
| β-D-2'-$CH_3$-riboC | 1 | 2.52 | 115.3 |
| | 10 | 2.36 | 107.9 |
| | 50 | 2.26 | 103.4 |
| | 100 | 2.21 | 101.2 |

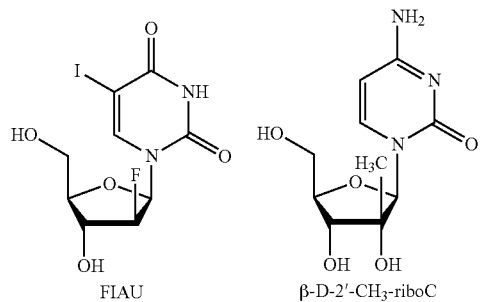

This invention has been described with reference to its preferred embodiments. Variations and modifications of the invention, will be obvious to those skilled in the art from the foregoing detailed description of the invention.

What is claimed is:

1. A method for the treatment of a hepatitis C virus infection in a host, comprising administering to the host an antivirally effective amount of a compound of Formula I:

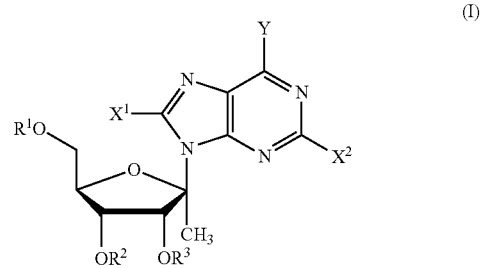

(I)

or a pharmaceutically acceptable salt or ester thereof, wherein:

$R^1$, $R^2$ and $R^3$ are independently hydrogen; monophosphate, diphosphate, triphosphate, or a stabilized phosphate prodrug; acyl; alkyl; sulfonate ester; a lipid; an amino acid; a carbohydrate; a peptide; a cholesterol; or other pharmaceutically acceptable leaving group which when administered in vivo is capable of providing a compound wherein $R^1$, $R^2$ or $R^3$ is independently hydrogen or phosphate; and Y is hydrogen, bromo, chloro, fluoro, iodo, $OR^4$, $NR^4R^5$ or $SR^4$;

$X^1$ and $X^2$ are independently hydrogen, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl, or alkyl.

2. A method for the treatment of a hepatitis C virus infection in a host, comprising administering to the host an antivirally effective amount of a compound of Formula III:

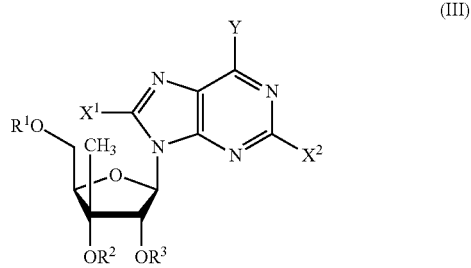

(III)

or a pharmaceutically acceptable salt or ester thereof, wherein:

$R^1$, $R^2$ and $R^3$ are independently hydrogen; monophosphate, diphosphate, triphosphate, or a stabilized phosphate prodrug; acyl; alkyl; sulfonate ester, a lipid; an amino acid; a carbohydrate; a peptide; a cholesterol; or other pharmaceutically acceptable leaving group which when administered in vivo is capable of providing a compound wherein $R^1$, $R^2$ or $R^3$ is independently hydrogen or phosphate; and Y is hydrogen, bromo, chloro, fluoro, iodo, $OR^4$, $NR^4R^5$ or $SR^4$;

$X^1$ and $X^2$ are independently hydrogen, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl, or alkyl.

3. A method for the treatment of a hepatitis C virus infection in a host, comprising administering to the host an antivirally effective amount of a compound of Formula IV:

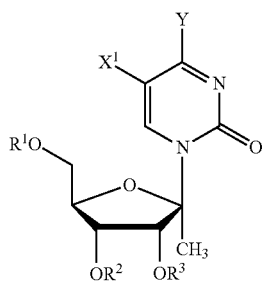

(IV)

or a pharmaceutically acceptable salt or ester thereof, wherein:

$R^1$, $R^2$ and $R^3$ are independently hydrogen, monophosphate, diphosphate, triphosphate, or a stabilized phosphate prodrug; acyl; alkyl; sulfonate ester; a lipid; an amino acid; a carbohydrate; a peptide; a cholesterol; or other pharmaceutically acceptable leaving group which when administered in vivo is capable of providing a compound wherein $R^1$, $R^2$ or $R^3$ is independently hydrogen or phosphate;

Y is hydrogen, bromo, chloro, fluoro, iodo, $OR^4$, $NR^4R^5$ or $SR^4$;

$X^1$ is hydrogen, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl, or alkyl.

4. The method of claim 1, wherein:

$R^1$, $R^2$ and $R^3$ are each independently hydrogen or phosphate;

$X^1$ is hydrogen;

$X^2$ is hydrogen or $NH_2$; and

Y is hydrogen, bromo, chloro, fluoro, iodo, $NH_2$ or OH.

5. The method of claim 2, wherein:

$R^1$, $R^2$ and $R^3$ are each independently hydrogen or phosphate;

$X^1$ is hydrogen;

$X^2$ is hydrogen or $NH_2$; and

Y is hydrogen, bromo, chloro, fluoro, iodo, $NH_2$ or OH.

6. The method of claim 3, wherein:

$R^1$, $R^2$ and $R^3$ are each independently hydrogen or phosphate;

$X^1$ is hydrogen or $CH_3$; and

Y is hydrogen, bromo, chloro, fluoro, iodo, $NH_2$ or OH.

7. The method of claim 1, wherein the compound has the formula:

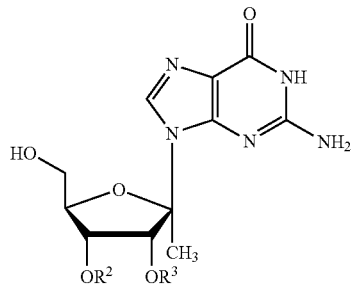

or a pharmaceutically acceptable salt or ester thereof.

8. The method of claim 1, wherein the compound has the formula:

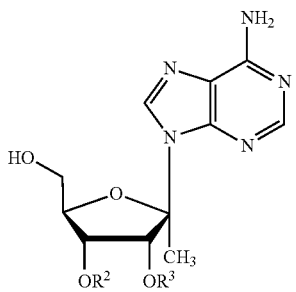

or a pharmaceutically acceptable salt or ester thereof.

9. The method of claim 1, wherein the compound has the formula:

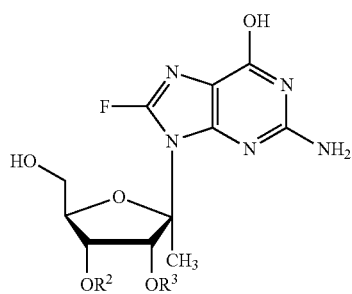

or a pharmaceutically acceptable salt or ester thereof.

10. The method of claim 1, wherein the compound has the formula:

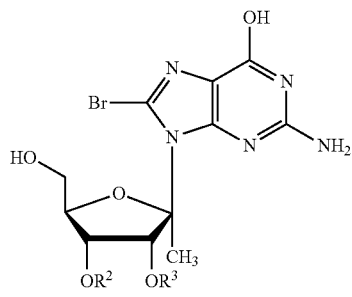

or a pharmaceutically acceptable salt or ester thereof.

11. The method of claim 2, wherein the compound has the formula:

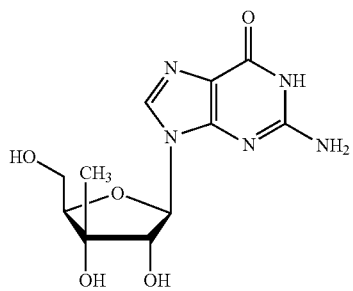

or a pharmaceutically acceptable salt or ester thereof.

12. The method of claim 2, wherein the compound has the formula:

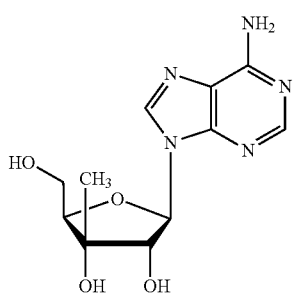

or a pharmaceutically acceptable salt or ester thereof.

13. The method of claim 2, wherein the compound has the formula:

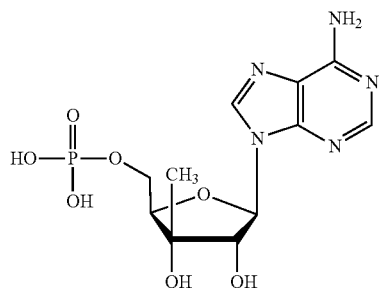

or a pharmaceutically acceptable salt or ester thereof.

14. The method of claim 3, wherein the compound has the formula:

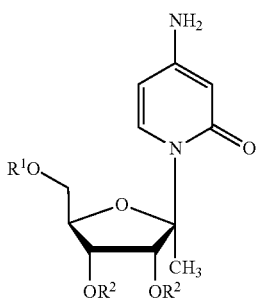

or a pharmaceutically acceptable salt or ester thereof.

15. The method of claim 3, wherein the compound has the formula:

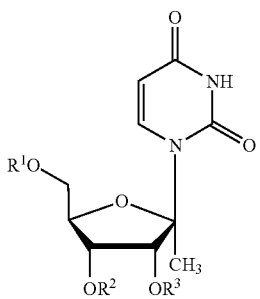

or a pharmaceutically acceptable salt or ester thereof.

16. The method of claim 3, wherein the compound has the formula:

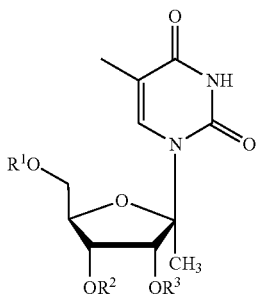

or a pharmaceutically acceptable salt or ester thereof.

17. The method of claim 1, wherein the compound of formula I is administered in combination or alternation with one or more antiviral agents.

18. The method of claim 2, wherein the compound of formula III is administered in combination or alternation with one or more antiviral agents.

19. The method of claim 3, wherein the compound of formula IV is administered in combination or alternation with one or more antiviral agents.

* * * * *